United States Patent
Goldshleger et al.

(10) Patent No.: US 11,135,052 B2
(45) Date of Patent: Oct. 5, 2021

(54) METHOD OF ADJUSTING A BLENDED EXTENDED DEPTH OF FOCUS LIGHT ADJUSTABLE LENS WITH LATERALLY OFFSET AXES

(71) Applicant: RxSight, Inc., Aliso Viejo, CA (US)

(72) Inventors: Ilya Goldshleger, Ladera Ranch, CA (US); John Kondis, Irvine, CA (US); Matt Haller, Costa Mesa, CA (US); Christian A. Sandstedt, Pasadena, CA (US); Pablo Artal, Murcia (ES); Eloy Angel Villegas, Alicante (ES)

(73) Assignee: RxSight, Inc.

( * ) Notice: Subject to any disclaimer, the term of this patent is extended or adjusted under 35 U.S.C. 154(b) by 71 days.

(21) Appl. No.: 16/236,659

(22) Filed: Dec. 31, 2018

(65) Prior Publication Data

US 2019/0142576 A1 May 16, 2019

Related U.S. Application Data

(63) Continuation-in-part of application No. 13/488,099, filed on Jun. 12, 2012.

(Continued)

(51) Int. Cl.
*A61F 2/16* (2006.01)
*A61L 27/18* (2006.01)

(52) U.S. Cl.
CPC .......... *A61F 2/1624* (2013.01); *A61F 2/164* (2015.04); *A61L 27/18* (2013.01); *A61F 2002/1683* (2013.01)

(58) Field of Classification Search
CPC ........ A61F 2/1627; A61F 2/16; A61F 2/1648; A61F 2/14; A61F 2002/1683; A61F 2002/16965; A61F 2/164

See application file for complete search history.

(56) References Cited

U.S. PATENT DOCUMENTS

| 4,260,725 A | 4/1981 | Keogh et al. |
| 4,457,590 A * | 7/1984 | Moore ............. G02B 9/02 359/654 |

(Continued)

FOREIGN PATENT DOCUMENTS

| CN | 1346251 | 4/2002 |
| CN | 1618030 | 5/2005 |

(Continued)

OTHER PUBLICATIONS

Reiley et al., (2009) "Ophthalmic applications of the digital micromirror device," Proceedings of SPIE. 721003-1: 721003-11.

(Continued)

*Primary Examiner* — Michael A Salvitti

(57) ABSTRACT

A Light Adjustable Lens (LAL) comprises a central region, centered on a central axis, having a position-dependent central optical power, and a peripheral annulus, centered on an annulus axis and surrounding the central region, having a position-dependent peripheral optical power; wherein the central optical power is at least 0.5 diopters different from an average of the peripheral optical power, and the central axis is laterally shifted relative to the annulus axis. A method of adjusting the LAL comprises implanting a LAL; applying a first illumination to the LAL with a first illumination pattern to induce a position-dependent peripheral optical power in at least a peripheral annulus, centered on an annulus axis; determining a central region and a corresponding central axis of the LAL; and applying a second illumination to the LAL with a second illumination pattern to induce a position-dependent central optical power in the central region of the LAL.

20 Claims, 42 Drawing Sheets

Related U.S. Application Data

(60) Provisional application No. 61/535,793, filed on Sep. 16, 2011.

(56) References Cited

U.S. PATENT DOCUMENTS

| | | | |
|---|---|---|---|
| 5,225,858 | A | 7/1993 | Portney |
| 5,236,970 | A | 8/1993 | Christ et al. |
| 5,278,258 | A * | 1/1994 | Gerace .................. C08L 83/04 |
| | | | 525/478 |
| 5,376,694 | A | 12/1994 | Christ et al. |
| 5,444,106 | A | 8/1995 | Zhou et al. |
| 6,145,987 | A | 11/2000 | Baude et al. |
| 7,281,795 | B2 | 10/2007 | Sandstedt et al. |
| 7,287,852 | B2 | 10/2007 | Fiala |
| 7,350,916 | B2 | 4/2008 | Hong et al. |
| 7,478,907 | B2 | 1/2009 | Somani et al. |
| 7,648,238 | B2 | 1/2010 | Dai et al. |
| 7,950,398 | B2 | 5/2011 | Schroeder et al. |
| 8,066,369 | B2 * | 11/2011 | Dreher .................. B24B 13/00 |
| | | | 351/159.02 |
| 8,109,999 | B2 | 2/2012 | Hampp |
| 8,142,499 | B2 | 3/2012 | Somani et al. |
| 8,307,832 | B2 | 11/2012 | Schroeder et al. |
| 8,529,559 | B2 | 9/2013 | Liang |
| 8,858,541 | B2 | 10/2014 | Liang |
| 10,010,406 | B2 | 7/2018 | Sandstedt et al. |
| 2002/0100990 | A1 * | 8/2002 | Platt ....................... A61F 9/008 |
| | | | 264/1.38 |
| 2002/0122153 | A1 * | 9/2002 | Piers ..................... A61F 2/1637 |
| | | | 351/212 |
| 2003/0151831 | A1 * | 8/2003 | Sandstedt ............ A61F 2/1635 |
| | | | 359/721 |
| 2004/0257676 | A1 * | 12/2004 | Schauss ............. G02B 27/0025 |
| | | | 359/760 |
| 2005/0043794 | A1 | 2/2005 | Geraghty et al. |
| 2005/0099597 | A1 * | 5/2005 | Sandstedt ............ A61F 2/1613 |
| | | | 351/159.4 |
| 2005/0187622 | A1 * | 8/2005 | Sandstedt ............ A61F 2/1624 |
| | | | 623/6.22 |
| 2006/0030938 | A1 * | 2/2006 | Altmann ............... A61F 2/1648 |
| | | | 623/6.37 |
| 2006/0244904 | A1 * | 11/2006 | Hong ....................... G02C 7/02 |
| | | | 351/159.01 |
| 2006/0244906 | A1 * | 11/2006 | Piers ..................... A61F 2/1654 |
| | | | 351/159.05 |
| 2006/0244916 | A1 * | 11/2006 | Guillon .................. G02C 7/041 |
| | | | 351/159.75 |
| 2006/0273479 | A1 * | 12/2006 | Brait ....................... B05D 5/06 |
| | | | 264/1.32 |
| 2007/0260311 | A1 * | 11/2007 | Jethmalani ........... A61F 2/1627 |
| | | | 351/159.02 |
| 2007/0279585 | A1 * | 12/2007 | Bartoli .................. A61F 2/1613 |
| | | | 351/159.01 |
| 2008/0027537 | A1 * | 1/2008 | Gerlach ................... A61L 27/50 |
| | | | 623/6.22 |
| 2008/0086207 | A1 | 4/2008 | Sandstedt et al. |
| 2008/0231810 | A1 * | 9/2008 | Catania ................... A61B 3/028 |
| | | | 351/247 |
| 2009/0157178 | A1 * | 6/2009 | Hampp ................ A61F 2/1624 |
| | | | 623/6.11 |
| 2010/0076554 | A1 * | 3/2010 | Sandstedt ............ A61F 2/1627 |
| | | | 623/6.24 |
| 2010/0057202 | A1 | 4/2010 | Bogaert |
| 2010/0165821 | A1 | 7/2010 | Kim et al. |
| 2010/0274234 | A1 * | 10/2010 | Liang ..................... A61F 9/00808 |
| | | | 606/5 |
| 2011/0082542 | A1 * | 4/2011 | Norrby ................ A61B 3/1035 |
| | | | 623/6.12 |
| 2011/0228217 | A1 | 9/2011 | Schroeder et al. |
| 2012/0123534 | A1 | 5/2012 | Yoon et al. |
| 2012/0130486 | A1 | 5/2012 | Yoon |
| 2013/0050840 | A1 * | 2/2013 | Oskotsky ............... G02B 13/18 |
| | | | 359/663 |
| 2013/0072591 | A1 * | 3/2013 | Sandstedt ............... B29C 35/00 |
| | | | 522/148 |
| 2013/0289153 | A1 * | 10/2013 | Sandstedt ............ A61F 2/1635 |
| | | | 522/148 |
| 2016/0324629 | A1 * | 11/2016 | Sandstedt ............ A61F 2/1637 |
| 2016/0339657 | A1 * | 11/2016 | Grubbs ................ A61F 2/1627 |
| 2018/0338827 | A1 * | 11/2018 | Goldshleger ........ A61F 2/1659 |
| 2019/0133755 | A1 | 5/2019 | Goldshleger et al. |
| 2019/0142576 | A1 | 5/2019 | Goldshleger et al. |

FOREIGN PATENT DOCUMENTS

| | | |
|---|---|---|
| CN | 1873476 | 12/2006 |
| CN | 101793984 | 8/2010 |
| EP | 2202544 | 6/2010 |
| WO | WO 00/41650 | 7/2000 |
| WO | WO 03/058296 | 7/2003 |
| WO | WO 2006/056847 A1 | 6/2006 |

OTHER PUBLICATIONS

Camellin and Calossi, (2006) "A new formula for intraocular lens power calculation after refractive corneal surgery," J. Refract. Surg. 22(2): 187-199.

Chokshi et al., (2007) "Intraocular lens calculations after hyperopic refractive surgery," Ophthalmology. 104(11): 2044-2049.

Fernandez et al., (2002) "Adaptive Optics Visual Simulator," J. Refract. Surg. 18: S634-S638.

Ellingson, (1990) "Explanation of 3M Diffractive Intraocular Lenses," J. Cataract and Refractive Surgery. 16: 697-701.

Fam and Lim, (2008) "A comparative analysis of intraocular lens power calculation methods after myopic excimer laser surgery" J. Refract. Surg. 24: 355-360.

Feiz et al., (2005) "Nomogram-based intraocular lens power adjustment after myopic photorefractive keratectomy and LASIK", Ophthalmology. 112: 1381-1387.

Hansen, et al., (1990) "New Multifocal Intraocular Lens Design," Cataract and Refractive Surgery. 16: 38-41.

Jin, et al., (2007) "Intraocular lens exchange due to incorrect lens power," Ophthalmology. 114: 417-424.

Latkany, et al., (2005) "Intraocular lens calculations after refractive surgery," J. Cataract and Refractive Surgery. 31: 562-570.

Mackool, et al., (2006) "Intraocular lens power calculation after laser in situ keratomileusis: aphakic refraction technique," J. Cataract and Refractive Surgery. 32: 435-437.

Mamalis et al, 2008 "Complications of foldable intraocular lenses requiring explantation or secondary intervention—2007 survey update,"J. Cataract & Refract Surg 34:1584-1591.

Murphy, et al., (2002) "Refractive error and visual outcome after cataract extraction," J. Cataract and Refractive Surgery. 28: 62-66.

Narvaez, et al., 2006 "Accuracy of intraocular lens power prediction using the Hoffer Q, Holladay 1, Holladay 2, and SRK/T formulas," J. Cataract & Refract Surg 32: 2050-2053.

Olsen, (1992) "Sources of error in intraocular-lens power calculation," J. Cataract and Refractive Surgery. 18: 125-129.

Packer, et al., (2004) "Intraocular lens power calculation after incisional and thermal keratorefractive surgery," J. Cataract and Refractive Surgery. 30: 1430-1434.

Packer, et al., (2002) "Refractive Lens Exchange with the Array Multifocal Intraocular Lens," J. Cataract and Refractive Surgery. 28: 421-424.

Preussner, et al., (2004) "Predicting postoperative intraocular lens position and refraction," J. Cataract and Refractive Surgery. 30: 2077-2083.

Steinert et al, 1999 "A Prospective Comparative Study of the AMO Array zonal-progressive multifocal silicone intraocular lens and a monofocal . . . ," Ophthalmology 106: 1243-1255.

Sun, et al., (2000) "Toric intraocular lenses for correcting astigmatism in 130 eyes," Ophthalmology. 107(9): pp. 1776-1781.

Thibos, et al., (2004) "Accuracy and Precision of Objective Refraction from Wavefront Aberrations," Journal of Vision. 4: 329-351.

(56) References Cited

OTHER PUBLICATIONS

Wang, et al., (2004) "Comparison of intraocular lens power calculation methods in eyes that have undergone LASIK," Ophthalmology 111: 1825-1831.
Bara, et al "Estimating the eye aberration coefficients in resized pupils: Is it better to refit or to rescale?" J. Opt Soc. Am. A, vol. 31, No. 1, Jan. 2014, pp. 114-123.
Piers, et al., "Adaptive Optics Simulation of Intraocular Lenses with Modified Spherical Aberration," IOVS, Dec. 2004, vol. 45, No. 12, pp. 4601-4610.
Charles E. Campbell, "Analysis of wavefront-guided corrections to see if they fully correct ocular aberrations," J. Opt Soc. Am. A, Jul. 2006, vol. 23, No. 7, pp. 1559-1565.
Pepose, et at, "Comparison of contrast sensitivity, depth of field and ocular wavefront aberrations . . . ," Graefes Arch Clin Exp Ophthahnol (2009) 247:965-973.
Cochener, et al., "Comparison of outcomes with multifocal intraocular lenses: a meta-analysis," Clinical Ophthalmology (2011) 5:45-56.
Salmon, et al., "Comparison of the eye's wave-front aberration measured psychophysically and with the . . . ," J. Opt. Soc. Am. A, Sep. 1998, vol. 15, No. 9, pp. 2457-2465.
A. Guirao and P. Artal, "Corneal wave aberration from videokeratography: accuracy and limitations of the Shack . . . ," J. Opt. Soc. Am. A, vol. 17, No. 6, Jun. 2000, pp. 955-965.
Legras, et al., "Effect of coma and spherical aberration on depth-of-focus measured using adaptive optics and . . . ," J Cataract Retract Surg, Mar. 2012, vol. 38, pp. 458-469.
Smith et al., "Effect of defocus on on-axis wave aberration of a centered optical system," J. Opt. Soc. Am. A, Nov. 2006, vol. 23, No. 11, pp. 2686-2689.
G. J. Burton and N. D. Haig, "Effects of the Seidel aberrations on visual target discrimination," J. Opt. Soc. Am. A, Apr. 1984, vol. 1, No. 4, pp. 373-385.
Gross et al., "Human eye," Handbook of Optical Systems: vol. 4 Survey of Optical Instruments. Edited by Herbert Gross, Mar. 2008, pp. 1-87.
K. Shinomori and J. S. Werner, "Impulse response of an S-cone pathway in the aging visual system," J. Opt. Soc. Am. A, Jul. 2006, vol. 23, No. 7, pp. 1570-1577.
Pulaski et al., "Measurement of aberrations in microlenses using a Shack-Hartmann wavefront sensor," Proc. SPIE 4767, Oct. 2002, pp. 1-9.
Valdemar Portney, "New Bi-Sign Aspheric IOL and Its Application," Optometry and Vision Science, vol. 89, No. 1, Jan. 2012, pp. 1-10.
Young et al., "Not all aberrations are equal: Reading impairment depends on aberration type and magnitude," Journal of Vision, Nov. 2011, 11(13):20, pp. 1-19.
Barbero et al, "Optical aberrations of intraocular lenses measured in vivo and in vitro," J. Opt. Soc. Am. A, vol. 20, No. 10, Oct. 2003, pp. 1841-1851.
Wang et al., "Optical aberrations of the human anterior cornea," J Cataract Refract Surg, vol. 29, Aug. 2003, pp. 1514-1521.
Werner et al., "Spherical aberration yielding optimum visual performance: Evaluation of intraocular lenses . . . ," J Cataract Refract Surg, vol. 35, Jul. 2009, pp. 1229-1233.
D. A. Atchison and H. Guo, "Subjective Blur Limits for Higher Order Aberrations," Optometry and Vision Science, vol. 87, No. 11, Nov. 2010. pp. E890-E898.
G. Smith and D. A. Atchison, "The gradient index and spherical aberration of the lens of the human eye," Ophthal. Physiol. Opt., vol. 21, No. 4, Jul. 2001, pp. 317-326.
Applegate et al., "Visual Acuity as a Function of Zernike Mode and Level of Root Mean Square Error," Optometry and Vision Science, vol. 80, No. 2, Feb. 2003, pp. 97-105.
Holladay et al., "A New Intraocular Lens Design to Reduce Spherical Aberration of Pseudophakic Eyes," Journal of Refractive Surgery, vol. 18, Nov./Dec. 2002, pp. 683-692.
Montes-Mico et al., "Analysis of the possible benefits of aspheric intraocular lenses: Review—of the literature," J Cataract Refract Surg, vol. 35, Jan. 2009, pp. 172-181.
H.-L. Liou and N. A. Brennan, "Anatomically accurate, finite model eye for optical modeling," J. Opt. Soc. Am. A, vol. 14, No. 8, Aug. 1997, pp. 1684-1695.
J. C. Wyant and K. Creath, "Basic Wavefront Aberration Theory for Optical Metrology," Applied Optics and Optical Engineering, vol. XI, 1992, pp. 1-12.
D. D. Koch and L. Wang, "Custom Optimization of Intraocular Lens Asphericity," Trans Am Ophthalmol Soc, vol. 105, 2007, pp. 36-42.
Buckhurst et al., "Development of a questionnaire to assess the relative subjective benefits of presbyopia correction," J Cataract Refract Surg, vol. 38, Jan. 2012, pp. 74-79.
Kay et al., "Extended depth of field by colored apodization," Optics Letters, vol. 36, No. 23, Dec. 1, 2011, pp. 4614-4616.
Zheleznyak et al., "Impact of corneal aberrations on through-focus image quality of presbyopia-correcting . . . ," J Cataract Refract Surg, vol. 38, Oct. 2012, pp. 1724-1733.
Applegate et al., "Interaction between aberrations to improve or reduce visual performance," J Cataract Refract Surg, vol. 29, Aug. 2003, pp. 1487-1495.
Atchison et al., "Limits of spherical blur determined with an adaptive optics mirror," Ophtha. Physio. Opt., vol. 29, No. 3, 2009, pp. 300-311.
Norrby et al., "Model eyes for evaluation of intraocular lenses," Applied Optics, vol. 46, No. 26, Sep. 2007, pp. 6595-6605.
Liang et al., "Objective measurement of wave aberrations of the human eye with the use of a Hartmann-Shack . . . ," J. Opt. Soc. Am. A, vol. 11, No. 7, Jul. 1994, pp. 1949-1957.
Iskander et al., "Objective refraction from monochromatic wavefront aberrations via Zernike power polynomials," Ophthal. Physiol. Opt., vol. 27, 2007, pp. 245-255.
Guirao et al., "Optical aberrations of the human cornea as a function of age," J. Opt. Soc. Am. A, vol. 17, No. 10, Oct. 2000, pp. 1697-1702.
Schwiegerling et al., "Representation of videokeratoscopic height data with Zernike polynomials," J. Opt. Soc. Am. A, vol. 12, No. 10, Oct. 1995, pp. 2105-2113.
Sicam et al., "Spherical aberration of the anterior and posterior surfaces of the human cornea," J. Opt. Soc. Am. A, vol. 23, No. 3, Mar. 2006, pp. 544-549.
Zhao et al., "Spherical Aberrations of Human Astigmatic Corneas," Journal of Refractive Surgery, vol. 27, No. 11, 2011, pp. 846-848.
Thibos et al., "Standards for Reporting the Optical Aberrations of Eyes," OSA TOPS, vol. 35 Vision Science and Its Applications, 2000, pp. 232-244.
Thibos et al., "Statistical variation of aberration structure and image quality in a normal," J. Opt. Soc. Am. A, vol. 19, No. 12, Dec. 2002, pp. 2329-2348.
Kollbaum, et al., "Validation of an Off-Eye Contact Lens Shack-Hartmann Wavefront Aberrometer," Optometry and Vision Science, vol. 85, No. 9, Sep. 2008, pp. E817-E828.
Cheng et al., "Visual Impact of Zernike and Seidel Forms of Monochromatic Aberrations," Optometry and Vision Science, vol. 87, No. 5, May 2010, pp. 301-312.
Villegas, et al., "Extended Depth of Focus With induced Spherical Aberration in Light-Adjustable Intraocular Lenses," American Journal of Ophthalmology, Jan. 2014, pp. 142-149.
A. J. Del Aguila-Carrasco, et al., "Optical quality of rotationally symmetrical contact lenses derived from their power profiles," Contact Lens & Anterior Eye, 2017, pp. 1-5.
Edward S. Bennett, "Contact lens correction of presbyopia," Clin Exp Optom 2008: 91: 3: 265-278.
A. K. S. Vogt, et al., "Using Power Profiles to Evaluate Aspheric Lenses," Contact Lens Spectrum, Issue: Jan. 2011.

\* cited by examiner

METHOD OF ADJUSTING A BLENDED EXTENDED DEPTH OF FOCUS LIGHT ADJUSTABLE LENS WITH LATERALLY OFFSET AXES

CROSS-REFERENCE TO RELATED APPLICATIONS

This patent application is a Continuation-In-Part of U.S. patent application Ser. No. 13/488,099, entitled "Using the light adjustable lens (LAL) to increase the depth of focus by inducing targeted amounts of asphericity", by C. A. Sandstedt, P. Artal, and E. Angel Villegas, filed on Jun. 4, 2012, that claims priority from and benefit of provisional application 61/535,793, filed on Sep. 16, 2011, the entire content of both applications hereby incorporated by reference in their entirety.

TECHNICAL FIELD

The field of the invention includes at least medical and surgical instruments; treatment devices; surgery and surgical supplies; and, medicine. In general, the field of subject matter of the invention includes ophthalmology. More specifically, the disclosure relates to optical elements, which can be modified post-manufacture such that different versions of the element will have different optical properties. In particular, the disclosure relates to lenses, such as intraocular lenses, which can be converted into aspheric lenses post-fabrication. This invention relates to light adjustable lenses with a depth of focus, and more specifically to blended extended depth of focus light adjustable lenses and to the methods of adjusting these lenses by illumination.

BACKGROUND

An intraocular lens (IOL) is a surgically implanted, polymeric lens designed to replace the natural crystalline lens in the human eye, typically in patients who have developed visually significant cataracts. Since their inception in the late 1940's, IOLs have provided improved uncorrected visual acuity (UCVA) compared to that of the cataractous or aphakic state; however, problems in predictably achieving emmetropia persist as most post-cataract surgery patients rely on spectacles or contact lenses for optimal distance vision. Compounding the issues related to achieving optimum distance vision, patients undergoing cataract surgery lose their ability to accommodate, i.e. the ability to see objects at both near and distance.

The determination of IOL power required for a particular post-operative refraction is dependent on the axial length of the eye, the optical power of the cornea, and the predicted location of the IOL within the eye. Accurate calculation of IOL power is difficult because the determination of axial length, corneal curvature, and the predicted position of the IOL in the eye is inherently inaccurate. (Narvaez el al., 2006; Olsen, 1992; Preussner el al., 2004; Murphy el al., 2002). Surgically induced cylinder and variable lens position following implantation will create refractive errors, even if preoperative measurements were completely accurate. (Olsen, 1992) Currently, the options for IOL patients with less than optimal uncorrected vision consist of post-operative correction with spectacles, contact lenses or refractive surgical procedures. Because IOL exchange procedures carry significant risk, secondary surgery to remove the IOL and replace the first IOL with a different power IOL is generally limited to severe post-operative refractive errors.

With current methods of IOL power determination, the vast majority of patients achieve a UCVA of 20/40 or better. A much smaller percentage achieves optimal vision without spectacle correction. Nearly all patients are within two diopters (D) of emmetropia.

In a study of 1,676 patients, 1,569 (93.6%) patients were within two diopters of the intended refractive outcome. (Murphy et al., 2002). In 1,320 cataract extractions on patients without ocular co-morbidity, Murphy and co-workers found that 858 (65%) had uncorrected visual acuity greater than 20/40. (Murphy el al., 2002). A 2007 survey of cataract surgeons reported that incorrect IOL power remains a primary indication for foldable IOL explantation or exchange. (Mamalis el al., 2008; and Jin el al., 2007)

In addition to imprecise IOL power determinations, post-operative uncorrected visual acuity is most often limited by pre-existing astigmatism. Staar Surgical (Monrovia, Calif.) and Alcon Laboratories (Ft. Worth, Tex.) both market a toric IOL that corrects pre-existing astigmatic errors. These IOLs are available in only two to three toric powers (2.0, 3.5 D and 1.50, 2.25 and 3.0 D, respectively at the IOL plane) and the axis must be precisely aligned at surgery. Other than surgical repositioning, there is no option to adjust the IOL's axis which may shift post-operatively. (Sun et al., 2000) Furthermore; individualized correction of astigmatism is limited by the unavailability of multiple toric powers.

An additional problem associated with using pre-implantation corneal astigmatic errors to gauge the required axis and power of a toric IOL is the unpredictable effect of surgical wound healing on the final refractive error. After the refractive effect of the cataract wound stabilizes, there is often a shift in both magnitude and axis of astigmatism which off-sets the corrective effect of a toric IOL. Therefore, a means to post-operatively adjust (correct) astigmatic refractive errors after lens implantation and surgical wound healing is very desirable. While limbal relaxing incision is a widely accepted technique for treating corneal astigmatism, the procedure is typically performed during cataract surgery; therefore, the procedure does not address the effect of post-implantation wound healing.

In the United States alone, approximately one million eyes undergo corneal refractive procedures which subsequently develop cataracts, thus, presenting a challenge with respect to IOL power determination. Corneal topographic alterations induced by refractive surgery reduce the accuracy of keratometric measurements, often leading to significant post-operative ametropia. (Feiz el al., 2005; Wang el al., 2004; Latkany el al., 2005; Mackool el al., 2006; Packer el al., 2004; Fam and Lim, 2008; Chokshi el al., 2007; Camellin and Calossi, 2006). Recent studies of patients who have had corneal refractive surgery (photorefractive keratectomy, laser in situ keratomileusis, radial keratotomy) and subsequently required cataract surgery frequently demonstrate refractive "surprises" post-operatively. As the refractive surgery population ages and develops cataracts, appropriate selection of IOL power for these patients has become an increasingly challenging clinical problem. The ability to address this problem with an adjustable IOL is valuable to patients seeking optimal distance vision after cataract surgery.

Accommodation, as it relates to the human visual system, refers to the ability of a person to use their unassisted ocular structure to view objects at both near (e.g. reading) and far (e.g. driving) distances. The mechanism whereby humans accommodate is by contraction and relaxation of the ciliary body, which connects onto the capsular bag surrounding the natural lens. Under the application of ciliary stress, the human lens will undergo a shape change effectively altering the radius of curvature of the lens. (Ciuffreda, 1998). This action produces a concomitant change in the power of the lens. However, as people grow older the ability for their eyes to accommodate reduces dramatically. This condition is known as presbyopia and currently affects more than 90 million people in the United States. The most widely accepted theory to explain the loss of accommodation was put forth by Helmholtz. According to Helmholtz, as the patient ages, the crystalline lens of the human eye becomes progressively stiffer prohibiting deformation under the applied action of the ciliary body. (Helmholtz, 1969). People who can see objects at a distance without the need for spectacle correction, but have lost the ability to see objects up close are usually prescribed a pair of reading glasses or magnifiers. For those patients who have required previous spectacle correction due to preexisting defocus and/or astigmatism, they are prescribed a pair of bifocals, trifocals, variable, or progressive focus lenses which allows the person to have both near and distance vision. Compounding this condition is the risk of cataract development as the patient ages.

To effectively treat both presbyopia and cataracts, the patient can be implanted with a multifocal IOL. The two most widely adopted multifocal IOLs currently sold in the United States are the ReZoom® (Abbott Medical Optics, Santa Ana, Calif.) and ReStor® (Alcon, Fort Worth, Tex.) lenses. The ReZoom® lens is comprised of five concentric, aspheric refractive zones. (U.S. Pat. No. 5,225,858). Each zone is a multifocal element and thus pupil size should play little or no role in determining final image quality. However, the pupil size must be greater than 2.5 mm to be able to experience the multifocal effect. Image contrast is sacrificed at the near and far distances, to achieve the intermediate and has an associated loss equivalent to one line of visual acuity. (Steiner el al., 1999). The ReStor® lenses, both the 3.0 and 4.0 versions, provide simultaneous near and distance vision by a series of concentric, apodized diffractive rings in the central, three millimeter diameter of the lenses. The mechanism of diffractive optics should minimize the problems associated with variable pupil sizes and small amounts of decentration. The acceptance and implantation of both of these lenses has been limited by the difficulty experienced with glares, rings, halos, monocular diplopia, and the contraindication for patients with an astigmatism of greater than or equal to 2.0 D. (Hansen el al., 1990; and, Ellingson, 1990). Again precise, preoperative measurements and accurate IOL power calculations are critical to the success of the refractive outcome, and neither the ReZoom nor the ReStor lenses provide an opportunity for secondary power adjustment post implantation. (Packer et al., 2002).

One of the newest concepts proposed to tackle the dual problems of cataracts and presbyopia are through the use of accommodating IOLs. Two companies, Bausch & Lomb (Rochester, N.Y.) and Human Optics AG (Erlangen, Germany) have developed IOLs that attempt to take advantage of the existing accommodative apparatus of the eye in post implantation patients to treat presbyopia. Bausch & Lomb's lens offers a plate haptic configured IOL with a flexible hinged optic (CrystaLens®). Human Optics's lens (AKKOMMODATIVE® ICU) is similar in design, but possesses four hinged haptics attached to the edge of the optic. The accommodative effect of these lenses is caused by the vaulting of the plate IOL by the contraction of the ciliary body. This vaulting may be a response of the ciliary body contraction directly or caused by the associated anterior displacement of the vitreous body. Initial reports of the efficacy of these two lenses in clinical trials was quite high with dynamic wavefront measurement data showing as much as 2 D to 3 D (measured at the exit pupil of the eye) of accommodation. However, the FDA Ophthalmic Devices' panel review of Bausch & Lomb's clinical results concluded that only a 1 D accommodative response (at the spectacle plane) was significantly achieved by their lens, which is nearly identical to the pseudo-accommodation values achieved for simple monofocal IOLs.

A need exists for an intraocular lens which is adjusted post operatively in-vivo to form a presbyopia correcting intraocular lens. This type of lens can be designed in-vivo to correct to an initial emmetropic state (light from infinity forming a perfect focus on the retina) and then the presbyopia correction is added during a second treatment. Such a lens would (1) remove the guess work involved in presurgical power selection, (2) overcome the wound healing response inherent to IOL implantation, and (3) allow the amount of near vision to be customized to correspond to the patient's requirements. Also, an intraocular lens which is adjusted post operatively in-vivo to form an aspheric optical element would result in the patient having an increased depth of focus (DOF), which allows the patient to see both distance and near (e.g. 40 cm) through the same lens.

The techniques of cataract surgery are progressing at an impressive pace. Generations of phacoemulsification platforms and more recently introduced surgical lasers keep increasing the precision of the placement of intraocular lenses (IOLs) and keep reducing unintended medical outcomes. Nevertheless, after the IOLs have been implanted, the postsurgical healing process can shift or tilt the IOLs in a notable fraction of the patients, leading to a diminished visual acuity, and a deviation from the planned surgical outcome.

A new technique has been developed recently to correct or mitigate such postsurgical IOL shift or tilt. This new technique is capable of adjusting the optical properties of the IOLs with a postsurgical procedure to compensate the shift or tilt of the IOL. As described elsewhere in this patent document and in commonly owned U.S. Pat. No. 6,905,641, to Platt et al, entitled: "Delivery system for post-operative power adjustment of adjustable lens", hereby incorporated by reference in its entirety, the IOLs can be fabricated from a photo-polymerizable material, henceforth making them Light Adjustable Lenses, or LALs. In the days after the surgery, the implanted LALs may shift and tilt, eventually settling into a postsurgical position different from what the surgeon planned. At this time, a Light Delivery System (LDD) can be used to illuminate the LALs with an illumination pattern that induces a change in the refractive properties of the LALs, such that their optical performance is modified to compensate the unintended postsurgical shift or tilt of the LAL.

Some existing IOLs have a radially varying optical power. Their optical performance is characterized by an extended depth of focus (EDOF), and thereby can be helpful to mitigate presbyopia in patients. Some of these EDOF IOLs are pre-formed before implantation. Alternatively, the radially varying optical power can be induced by applying a radially varying illumination pattern after the LAL was implanted and then settled, as described elsewhere in this document. While the medical benefit of the EDOF IOLs is substantial, the effective optical power of these EDOF IOLs varies with the radius of the pupil of the eye. Thus, as light conditions vary, such as when transitioning from an indoor environment to outdoors, as the pupil adapts to the transition, the optical performance of such EDOF IOLs/LALs changes, which can be challenging to adapt to for a notable fraction of patients. Also, since these EDOF IOLs/LALs have an extended focal region instead of a sharply defined focal point, the image they create on the retina is experienced by some patients as having some aberrations, being somewhat blurry.

Another class of presbyopia-mitigating IOLs has been described in the commonly owned U.S. Pat. No. 7,281,795, to Sandstedt et al., entitled: "Light adjustable multifocal lenses", hereby incorporated by reference in its entirety. This class of IOLs have a central region with a central optical power and corresponding central focal point, and a peripheral region with a peripheral optical power and corresponding peripheral focal point. Accordingly, these are sometimes referred to as multifocal IOLs. Typically, the central region is formed for near vision and the peripheral region for distance vision. Accordingly, the central optical power is typically 1-3 diopters stronger than the peripheral optical power. The central region is sometimes referred to as a "Central Near Add" (CNA) region. As with EDOF IOLs, multifocal IOLs can also be either pre-formed prior to the surgery, or can be formed post-surgically, by applying an appropriate illumination pattern to an implanted LAL.

These CNA, or multifocal IOLs have the potential to mitigate presbyopia similarly to multifocal contact lenses. One of the medical benefits of these multifocal lenses is that their focal points are well-defined. Therefore, the images they form at the focal points have only small aberrations. At the same time, one of the challenges of multifocal IOLs is that the visual acuity strongly depends on how precisely the CNA region is aligned with the visual axis of the eye. Even a small decentering of the small CNA region can induce various aberrations and astigmatism, most notably coma, and thus can cause a substantial deterioration of the visual acuity. Since the CNA region is typically quite small, and the implanted multifocal IOLs also tend to shift and tilt, the visual acuity of the pre-formed multifocal IOLs often deteriorates as they shift and de-center after implantation.

There are several possible sources of decentering. In cases, where the central region is formed prior to implantation, such as molded into an IOL, or into a LAL, the postsurgical shifts of the IOL/LAL can lead to a correspondingly decentered central region. In cases, where the central region is formed after the implantation by illuminating the LAL with a suitable illumination pattern, another issue can lead to the same problem. The LALs are illuminated after the iris of the eye is substantially dilated, in order to accommodate the entire illumination pattern. In some cases, the illumination pattern to form the CNA region can be centered on the geometric axis of the LAL. Less typically, the illumination pattern can be centered on the dilated iris. In either case, subsequently the iris often returns to its natural, non-dilated state non-symmetrically, thus shifting the visual axis of the eye. Thus, the CNA region that was centered either on the geometric LAL axis, or on the dilated iris, may end up being notably decentered from the visual axis of the eye, defined by the non-dilated iris.

The problematic visual acuity of the decentered central CNA region is probably one of the causes why existing CNA/multifocal IOLs achieved only limited market acceptance. It is mentioned that the Central Near Add concept has been also implemented in related ophthalmic technologies: as implanted small corneal inlays, and as CNA contact lenses. These technologies also suffer from the analogous problem of postsurgical shift and decentration.

For at least the above reasons, there is a pressing medical need for the following improvement in the field of presbyopia-mitigating IOLs/LALs. (1) A new class of IOLs/LALs that deliver the presbyopia-mitigating medical benefits of the EDOF and the CNA/multifocal designs, while limiting or minimizing the undesirable aspects of their optical performance. (2) LALs/IOLs, whose CNA region is aligned with the visual axis of the eye in the non-dilated state of the iris.

SUMMARY

General embodiments of the present invention provide a first optical element whose properties may be adjusted post-manufacture to produce a second optical element, wherein the second optical element is capable of providing an increased depth of focus to a patient. Specifically, the invention relates to a spherical intraocular lens that is capable of being transformed post-operatively into an aspheric optical element. Through this approach, the intraocular and/or focal zones of the aspheric optical element can be more precisely adjusted after the lens has been subjected to any post-operative migration. Also, the adjustment of the aspheric optical element can be based on input from the patient and/or the adjustment of the aspheric optical element can be accomplished through standard refraction techniques rather than making the adjustment through pre-operative estimation.

The alteration of the spherical IOL is accomplished via a modifying composition ("MC") dispersed throughout the spherical IOL. The MC is capable of polymerization when exposed to an external stimulus such as heat or light. The stimulus can be directed to one or more regions of the element causing polymerization of the MC only in the exposed regions. The polymerization of the MC causes changes in the optical properties of the element within the exposed regions. In some embodiments, the optical properties changed though the polymerization of the MC include a change in the radius of curvature and/or a change in the refractive index.

The method for providing an aspheric lens begins with the formation of the first polymer matrix in the presence of the modifying composition. The next step is the formation of a second polymer matrix comprising polymerized MC. The formation of this polymer network changes the optical properties of the element, namely the refractive index. In addition, when the MC is polymerized to form the second polymer matrix, a gradient or a difference in the chemical potential between the polymerized and unpolymerized regions is induced. This in turn causes the unpolymerized MC to diffuse within the element, which reestablishes a thermodynamic equilibrium within the optical element. If the optical element possesses sufficient elasticity, this migration of MC can cause swelling of the element in the area exposed to the stimulus. This, in turn, changes the shape of the element, causing changes in the optical properties (i.e., radius of curvature and/or refractive index). Whether the radius of curvature of the element and/or the refractive index of the element change depends upon (1) the nature of the optical element, (2) the MC incorporated into the element, (3) the duration that the element is exposed to a stimulus, and (4) the spatial intensity profile of the stimulus.

By controlling the radiant exposure (i.e., beam irradiance and duration), spatial irradiance profile, and target area, physical changes in the radius of curvature of the lens surface are achieved, thereby modifying the refractive power of an implanted lens (1) to correct spherical refractive errors, (2) to correct sphero-cylindrical refractive errors, (3) to induce a targeted amount of asphericity and/or a combination thereof. Once the appropriate refractive adjustment is achieved, the entire aspheric lens is irradiated to polymerize the remaining unreacted MC under conditions that prevent any additional change in lens power. By irradiating the entire lens, MC diffusion is prevented thus no change in lens power results. This second irradiation procedure is referred to as "lock-in".

In another aspect of the present invention, the optical elements are self-contained in that once fabricated, no material is either added or removed from the lens to obtain the desired optical properties.

The above described medical needs are further addressed by the following embodiments of Light Adjustable Lenses. Some embodiments of a Light Adjustable Lens (LAL) can comprise a central region, centered on a central axis, having a position-dependent central optical power, and; a peripheral annulus, centered on an annulus axis and surrounding the central region, having a position-dependent peripheral optical power, wherein an average of the central optical power is at least 0.5 diopters different from an average of the peripheral optical power, and the central axis is laterally shifted relative to the annulus axis.

In some embodiments, a Light Adjustable Lens (LAL) comprises a light-adjusted region, centered on an adjustment axis and having a position-dependent optical power; wherein the adjustment axis is laterally shifted relative to a LAL axis of the LAL.

In some embodiments, a method of adjusting a Light Adjustable Lens (LAL) comprises the steps of: implanting a LAL into an eye; applying a first illumination to the LAL with a first illumination pattern to induce a position-dependent peripheral optical power in at least a peripheral annulus, centered on an annulus axis; determining a central region and a corresponding central axis of the LAL; and applying a second illumination to the LAL with a second illumination pattern to induce a position-dependent central optical power in the central region of the LAL; wherein the central axis is laterally shifted relative to the annulus axis, and an average of the central optical power is at least 0.5 diopters different from than an average of the peripheral optical power.

In some embodiments, a method of adjusting a Light Adjustable Lens (LAL) comprises the steps of implanting a LAL into an eye, the LAL having a pre-molded position-dependent peripheral optical power in at least a peripheral annulus, centered on an annulus axis; determining a central region and a corresponding central axis of the LAL; and applying a central illumination to the LAL with a central illumination pattern to induce a position-dependent central optical power in the central region of the LAL; wherein the central axis is laterally shifted relative to the annulus axis, and an average of the central optical power is at least 0.5 diopters different from than an average of the peripheral optical power.

In some embodiments, a method of adjusting a Light Adjustable Lens (LAL) comprises the steps of: implanting a LAL, having a LAL axis, into an eye; and applying an illumination to the LAL with an illumination pattern to induce a position-dependent optical power in a light-adjusted region, centered on an adjustment axis; wherein the adjustment axis is laterally shifted relative to the LAL axis.

In some embodiments, a method of adjusting a Light Adjustable Lens (LAL) comprises the steps of: causing an LAL, implanted into an eye, to induce a first depth of focus of the ophthalmic optical system; determining a central region and a corresponding central axis of the LAL; and illuminating the LAL with an illumination pattern centered on the central axis to induce a second depth of focus of the ophthalmic optical system; wherein the central axis is laterally shifted relative to a LAL axis, and the second depth of focus is at least 0.5 diopters greater than the first depth of focus.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

DETAILED DESCRIPTION

Figure 1:
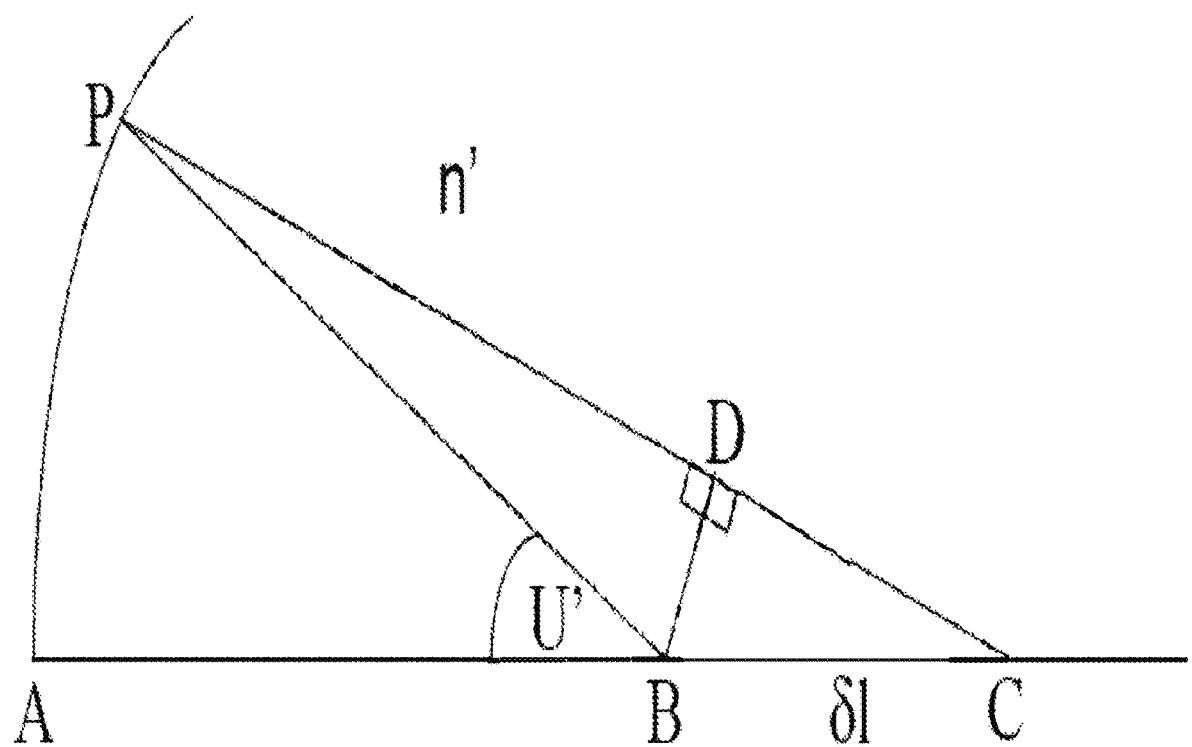
FIG. 1 shows a schematic representation of the depth of focus.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, as used herein, the terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

Throughout this application, the term "about" is used to indicate that a value includes the inherent variation of error for the device, the method being employed to determine the value, or the variation that exists among the experimental test articles.

Chemical Group Definitions

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "isocyanate" means —N=C=O; "azido" means —N$_3$; in a monovalent context "phosphate" means —OP(O)(OH)$_2$ or a deprotonated form thereof in a divalent context "phosphate" means —OP(O)(OH)O— or a deprotonated form thereof; "mercapto" means —SH; and "thio" means =S In the context of chemical formulas, the symbol "—" means a single bond, "=" means a double bond, and "≡" means triple bond. The symbol " ═══ " resents an optional bond, which if present is either single or double. The symbol " ___ " represents a single bond or a double bond. Thus, for example, the structure

includes the structures

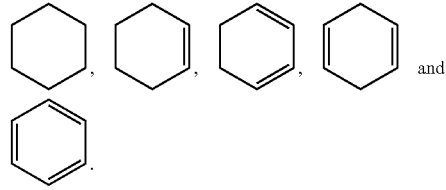

As will be understood by a person of skill in the art, no one such ring atom forms part of more than one double bond. The symbol " ⁓ ", when drawn perpendicularly across a bond indicates a point of attachment of the group. It is noted that the point of attachment is typically only identified in this manner for larger groups in order to assist the reader in rapidly and unambiguously identifying a point of attachment. The symbol " ▰ " means a single bond where the group attached to the thick end of the wedge is "out of the page." The symbol " ▮▮▮▮ " means a single bond where the group attached to the thick end of the wedge is "into the page". The symbol " ⁓ " means a single ⁓ bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

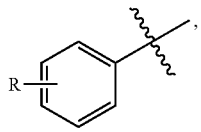

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

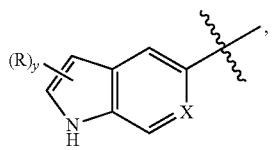

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms)). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —H$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$) (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

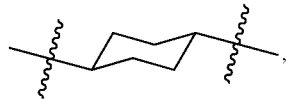 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH, —CH$_2$OC (O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH₂Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CH—C₆H₅. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH—CH—, —CH=C(CH₃)CH₂—, —CH=CHCH₂—, and

are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH)₂, —C(O)NH₂, —OC(O)CH₃, or —S(O)₂NH₂. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one carbon-carbon triple bond, and no atoms other than carbon and hydrogen. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH)₂, —C(O)NH₂, —OC(O)CH₃, or —S(O)₂NH₂. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

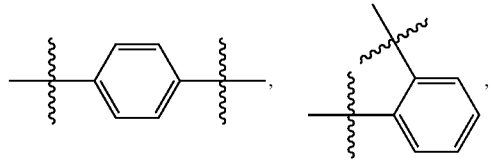

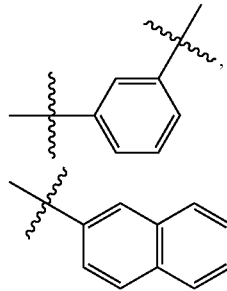 and

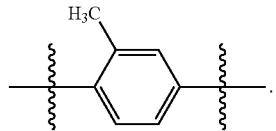

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CHs)₂, —C(O)NH₂, —OC(O)CH₃, or —S(O)₂NH₂. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —N—, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the group consists of no atoms other than carbon, hydrogen, aromatic nitrogen, aromatic oxygen and aromatic sulfur. As used herein, the term does not preclude the presence of one or more alkyl group (carbon number limitation permitting) attached to the aromatic ring or any additional aromatic ring present. Non-limiting examples of heteroaryl groups include furanyl, imidazolyl, indolyl; indazolyl (Im), methylpyridyl, oxazolyl, pyridyl, pyrrolyl, pyrimidyl, pyrazinyl, quinolyl, quinazolyl, quinoxalinyl, thienyl, and triazinyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of heteroarenediyl groups include:

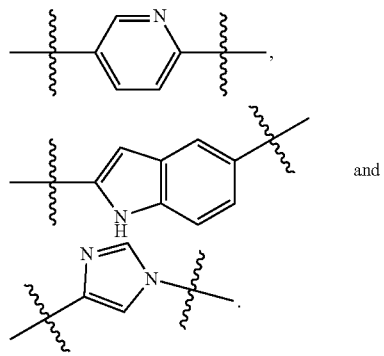

and

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CHI)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃, —OCH₂CH₃, —OCH₂CH₂CH₃, —OCH(CH₃)₂, —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. Similarly, the term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. When any of these terms is used with the "substituted"

modifier one or more hydrogen atom has been independently replaced by —OH, —F, —Cl, —Br, —I, —NH, —NO$_2$, —CO$_2$H, —CO$_2$CH$_3$, —CN, —SH, —OCHN, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OHXOR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe)$_2$, and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —N, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "effective," as that term is used in the specification and/or claims, means adequate to accomplish a desired, expected, or intended result. "Effective amount," or "Therapeutically effective amount" when used in the context of treating a patient or subject with a stimulus means that the amount of the stimulus which, when administered to a subject or patient for treating a condition, is sufficient to effect such treatment for the condition.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—CH$_2$CH$_2$—]$_n$—, the repeat unit is —CH$_2$CH$_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in, modified polymers, thermosetting polymers, etc.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Compositions of the Invention

Compositions of the present disclosure may be made using the methods described above and in Example 1 below. These methods can be further modified and optimized using the principles and techniques of organic chemistry and/or polymer chemistry as applied by a person skilled in the art. Such principles and techniques are taught, for example, in *March's Advanced Organic Chemistry: Reactions, Mechanisms, and Structure* (2007), and/or in RJ. Young & P. A. Lovell, *Introduction to Polymers*, (Chapman & Hall 1991), which are incorporated by reference herein.

Discussion of General Embodiments

From a pure optical standpoint, the depth of focus (DOF) for an optical system (e.g. the eye) is simply defined as the maximum movement away from the ideal image plane, which may be made without causing a serious deterioration of the image. According to the Rayleigh limit, there will be no appreciable deterioration of the image, i.e., no marked change from the Airy pattern, provided the maximum phase difference between disturbances arriving at the center of the pattern, does not exceed π/2. With reference to FIG. 1, this is mathematically stated as:

$$\delta l = \pm \frac{\lambda}{8n' \sin^2 \frac{U'}{2}}$$

where AP represents a spherical wave converging to the image point B, λ is the wavelength, n' is the refractive index in the image space, U' is the slope of the refracted ray, and δ1 is the DOF. Therefore, an optical system such as the human eye will have an inherent amount of depth of focus even for a perfectly imaging system.

Figure 2:
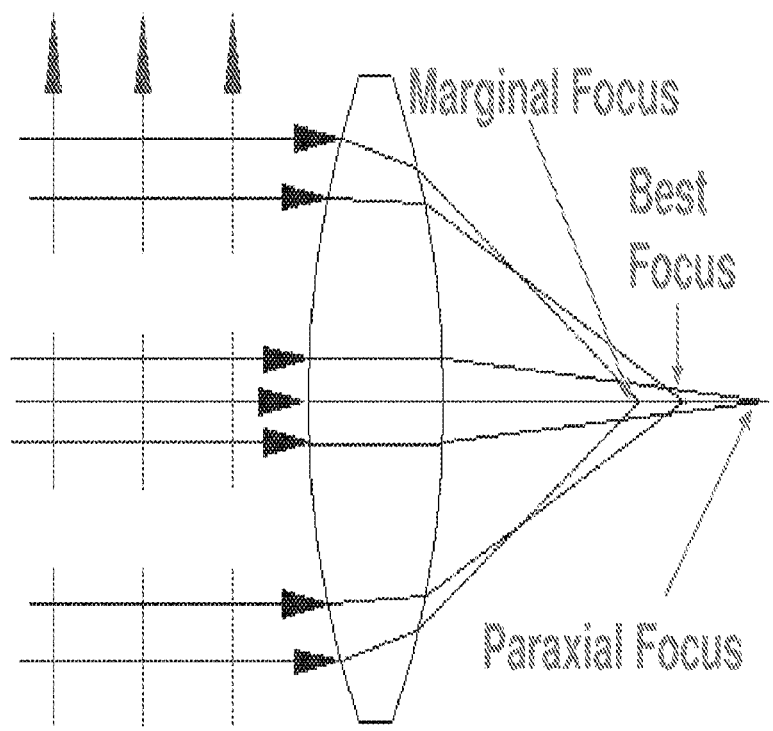
FIG. 2 shows a collimated beam of light being refracted by a spherical lens.

An additional property of optical systems that can be exploited to further increase the depth of focus, and therefore provide for both distance and near vision, is spherical aberration. In simple terms, spherical aberration is defined as the variation of focus with aperture. FIG. 2 graphically depicts a collimated beam of light being refracted by a spherical biconvex lens. Notice that the rays closest to the optical axis come to a focus close to the paraxial focus position. As the ray height at the lens increases, the position of the ray's intersection with the optical axis moves farther and farther away from the paraxial focus. The distance from the paraxial focus to the axial intersection of the ray is called longitudinal spherical aberration. The image of a point formed by a lens with spherical aberration is usually a bright dot surrounded by a halo of light. The effect of spherical aberration on an extended image is to soften the contrast of the image and blur its details. However, it should be possible to induce a specific spherical aberration that increases the depth of focus such that the softening of the focus and the image contrast is acceptable.

Figure 3:
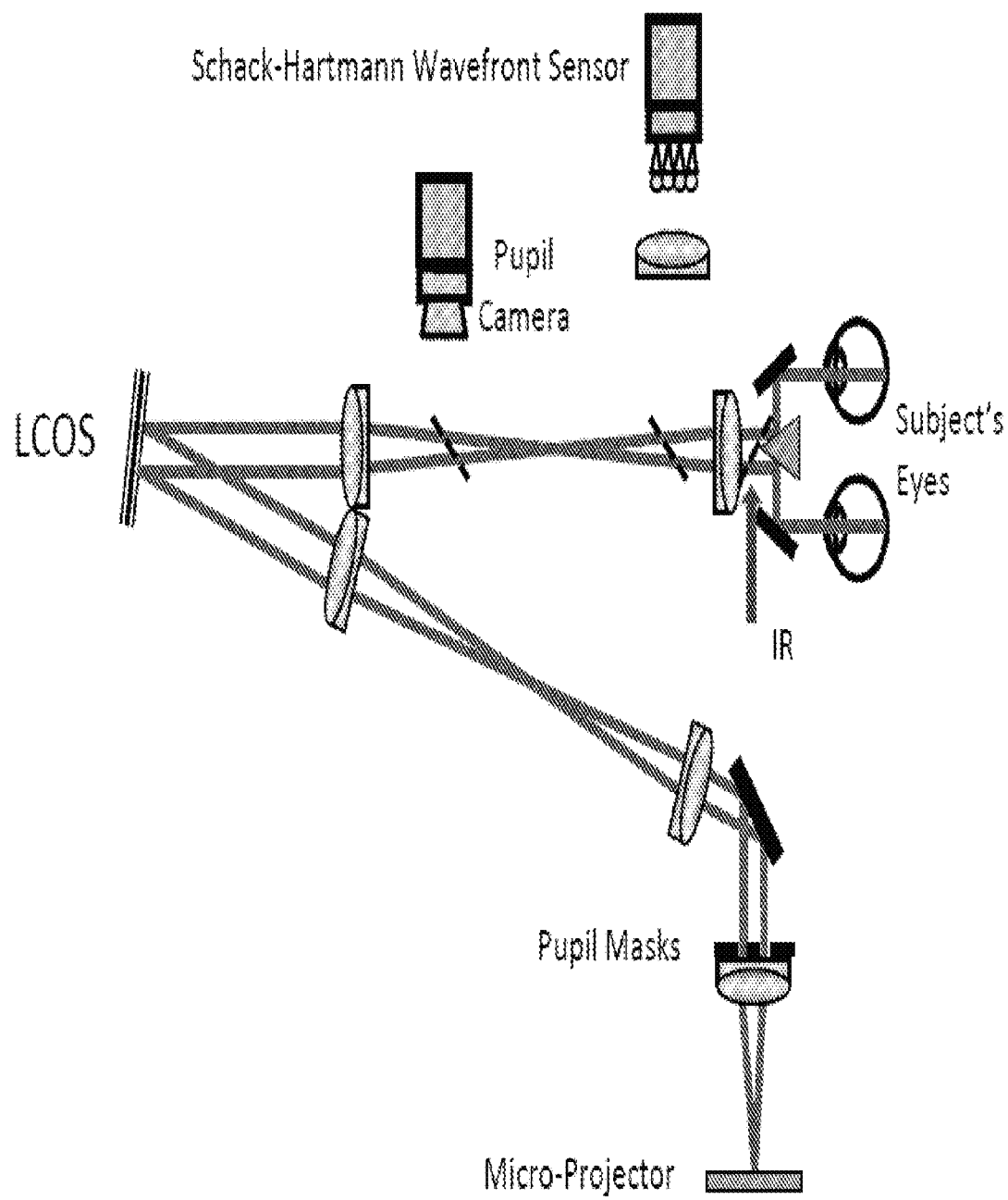
FIG. 3 shows a schematic of the adaptive optics simulator used to determine the optimized values for $4^{th}$ order spherical aberration and defocus.

The presence of spherical aberration increases the depth of focus in the eye. In combination with a residual refractive error (defocus), an induced spherical aberration can be used to provide patients with good contrast images both for distance and near objects. The key issue is to determine the required values of both $4^{th}$ order spherical aberration and defocus that provide good near vision without deteriorating the image quality for distance objects. An experimental approach that permits determination of the optimum values of spherical aberration and defocus is an adaptive optics visual simulator. (Fernandez el al., 2002). An example of this type of instrument is shown in FIG. 3. This instrument consists of a wavefront sensor (Shack-Hartmann wavefront sensor), a wavefront corrector (Liquid Crystal on Silicon (LCOS)), and an additional optical path to present letters, e.g., a tumbling E, to the subjects under test. The visual acuity of several subjects was measured using a similar setup as that shown in FIG. 3. The visual acuity of the subjects was measured through simulations that consisted of a number of different combinations of residual defocus and spherical aberration measurements for letter objects placed at distances from 30 cm to distance emmetropia. The results of these simulations indicate that the optimum values of negative spherical aberration and defocus to maintain good vision between 40 cm and distance emmetropia are −0.125 μm of $4^{th}$ order spherical aberration in combination with −1.0 D of defocus.

The spherical IOL of the present invention is capable of post-fabrication alteration of optical properties. The lens is self-contained and does not require the addition or removal of materials to change the optical properties. Instead, the optical properties of the lens arealtered by exposing a portion or portions of the lens to an external stimulus which induces polymerization of a MC within the lens. The polymerization of the MC, in turn, causes the change in optical properties.

In some examples, the optical element of the invention has dispersed within it a MC. The MC is capable of diffusion within the lens; can be readily polymerized by exposure to a suitable external stimulus; and is compatible with the materials used to make the first polymer matrix of the lens.

Figure 4:
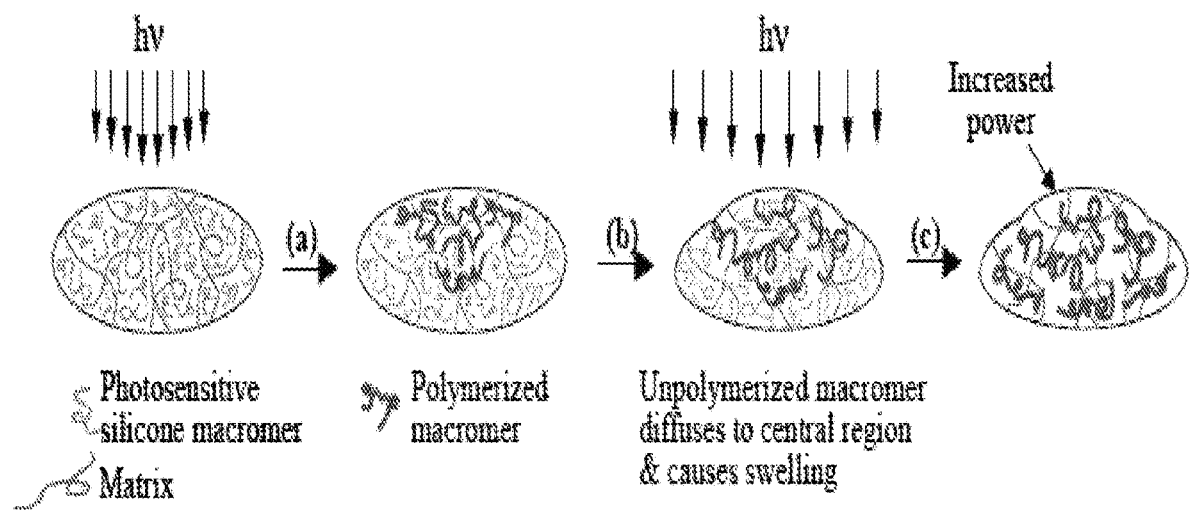
FIG. 4 shows a schematic of positive power adjustment mechanism; wherein (a) is a schematic representation of selective irradiation of the central zone of the lens in which the polymerization of the MC creates a difference in the chemical potential between the irradiated and non-irradiated regions, (b) to reestablish equilibrium, excess MC diffuses into the irradiated region causing swelling, and (c) irradiation of the entire lens "locks" the remaining MC and the shape change.

The method for providing an aspheric lens begins with the formation of the first polymer matrix. After the first polymer matrix is formed, the second polymer matrix is formed by exposing the first polymer matrix, which further comprises the MC, to an external stimulus. During this second polymerization, several changes occur within the optical element. The first change is the formation of a second polymer matrix comprising polymerized MC. The formation of the second polymer network can cause changes in the optical properties of the element, namely the refractive index. In addition, when the MC polymerizes, a difference in the chemical potential between the polymerized and unpolymerized region is induced. This in turn causes the unpolymerized MC to diffuse within the element, which reestablishes thermodynamic equilibrium of the optical element. If the optical element possesses sufficient elasticity, this migration of MC can cause swelling of the element in the area exposed to the stimulus. This, in turn, changes the shape of the element, causing changes in the optical properties. Whether the radius of curvature of the element and/or the refractive index of the element change depends upon (1) the nature of the optical element, (2) the MC incorporated into the element, (3) the duration that the element is exposed to the stimulus, and (4) the spatial intensity profile of the stimulus. A schematic depicting the process for increasing the power of the lens is displayed in FIG. 4.

The optical element is typically made of a first polymer matrix. Illustrative examples of a suitable first polymer matrix include: (1) polyacrylates such as polyalkyl acrylates and polyhydroxyalkyl acrylates; (2) polymethacrylates such as polymethyl methacrylate ("PMMA"), polyhydroxyethyl methacrylate ("PHEMA"), and polyhydroxypropyl methacrylate ("HPMA"); (3) polyvinyls such as polystyrene and polyvinylpyrrolidone ("PNVP"); (4) polysiloxanes such as polydimethylsiloxane; polyphosphazenes, and/or (5) copolymers thereof. U.S. Pat. No. 4,260,725 and patents and references cited therein (which are all incorporated herein by reference) provide more specific examples of suitable polymers that may be used to form the first polymer matrix.

In preferred embodiments, where flexibility is desired, the first polymer matrix generally possesses a relatively low glass transition temperature ("$T_g$") such that the resulting IOL tends to exhibit fluid-like and/or elastomeric behavior, and is typically formed by cross-linking one or more polymeric starting materials wherein each polymeric starting material includes at least one cross-linkable group. In the case of an intraocular lens, the $T_g$ should be less than 25° C. This allows the lens to be folded, facilitating implantation.

The crosslinking reaction of the polymeric starting material is accomplished via a hydrosilylation reaction. The general scheme for the hydrosilylation reaction is shown below.

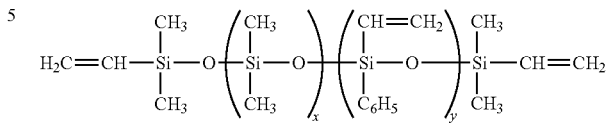

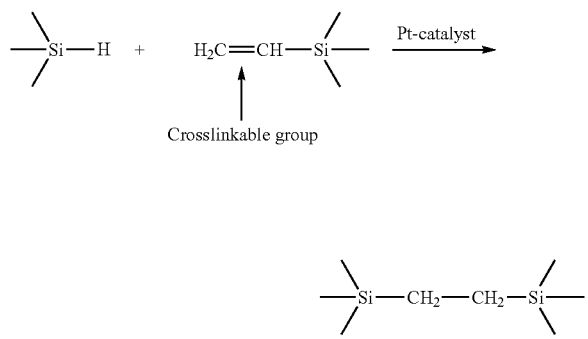

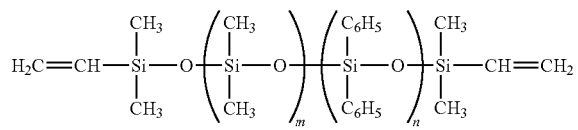

During this crosslinking step, a high molecular weight long vinyl-capped silicone polymer and multi-functional vinyl-capped silicone resin are crosslinked using multifunctional hydrosilane crosslinkers. This crosslinking step forms the first polymer matrix in the presence of MC and photoinitiator.

In some embodiments, the high molecular weight, long vinyl-capped silicone polymer has the following formula.

$$H_2C=CH-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_m\left(\underset{\underset{C_6H_5}{|}}{\overset{\overset{C_6H_5}{|}}{Si}}-O\right)_n\underset{\underset{CH_3}{|}}{\overset{\overset{CH_3}{|}}{Si}}-CH=CH_2$$

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some embodiments, multi-functional vinyl-capped silicone resin has the following formula.

$$H_2C=CH-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_x\left(\underset{\underset{C_6H_5}{|}}{\overset{\overset{CH=CH_2}{|}}{Si}}-O\right)_y\underset{\underset{CH_3}{|}}{\overset{\overset{CH_3}{|}}{Si}}-CH=CH_2$$

In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, y represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, y represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some embodiments, multi-functional hydrosilane crosslinker has the following formula.

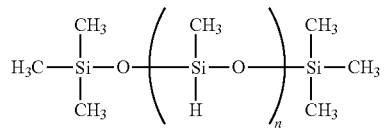

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

Illustrative examples of suitable cross-linkable groups include but are not limited to vinyl, hydride, acetoxy, alkoxy, amino, anhydride, aryloxy, carboxy, enoxy, epoxy, halide, isocyano, olefinic, and oxine. In more preferred embodiments, the polymeric starting material includes terminal monomers (also referred to as endcaps) that are either the same or different from the one or more monomers that comprise the polymeric starting material but include at least one cross-linkable group. In other words, the terminal monomers begin and end the polymeric starting material and include at least one cross-linkable group as part of its structure. Although it is not necessary for the practice of the present invention, the mechanism for cross-linking the polymeric starting material preferably is different than the mechanism for the stimulus-induced polymerization of the components that comprise the refraction modulating composition. For example, if the refraction modulating composition is polymerized by photoinduced polymerization, then it is preferred that the polymeric starting materials have cross-linkable groups that are polymerized by any mechanism other than photoinduced polymerization.

An especially preferred class of polymeric starting materials for the formation of the first polymer matrix is polysiloxanes (also known as "silicones") endcapped with a terminal monomer which includes a cross-linkable group selected from the group consisting of vinyl, acetoxy, amino, alkoxy, halide, hydroxy, and mercapto. Because silicone IOLs tend to be flexible and foldable, generally smaller incisions may be used during the IOL implantation procedure. An example of an especially preferred polymeric starting materials are vinyl endcapped dimethylsiloxane diphenylsiloxane copolymer, silicone resin, and silicone hydride crosslinker that are crosslinked via an addition polymerization by platinum catalyst to form the silicone matrix (see the above reaction scheme). Other such examples may be found in U.S. Pat. Nos. 5,236,970; 5,376,694; 5,278,258; 5,444,106; and, others similar to the described formulations. U.S. Pat. Nos. 5,236,970; 5,376,694; 5,278,258; and 5,444,106 are incorporated herein by reference in their entirety.

The MC that is used in fabricating IOLs is as described above except that it has the additional requirement of biocompatibility. The MC is capable of stimulus-induced polymerization and may be a single component or multiple components so long as: (1) it is compatible with the formation of the first polymer matrix; (2) it remains capable of stimulus-induced polymerization after the formation of the first polymer matrix; and (3) it is freely diffusible within the first polymer matrix. In general, the same type of monomers that are used to form the first polymer matrix may be used as components of the refraction modulating composition. However, because of the requirement that the MC macromer must be diffusible within the first polymer matrix, the MC macromers generally tend to be smaller (i.e., have lower molecular weights) than the starting polymeric materials used to form the first polymer matrix. In addition to the one or more monomers, the MC may include other components such as initiators and sensitizers that facilitate the formation of the second polymer network.

In preferred embodiments, the stimulus-induced polymerization is photopolymerization. In other words, the one or more monomers or macromers that comprise the refraction modulating composition each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the refraction modulating composition includes a photoinitiator (any compound used to generate free radicals) either alone or in the presence of a sensitizer. Examples of suitable photoinitiators include acetophenones (e.g., substituted haloacetophenones, and diethoxyacetophenone); 2,4-dichloromethyl-1,3,5-trazines; benzoin methyl ether, and o-benzoyl oximino ketone. Examples of suitable sensitizers include p-(dialkyiamino)aryl aldehyde; N-alkylindolylidene; and bis[p-(dialkylamino)benzylidene] ketone.

Because of the preference for flexible and foldable IOLs, an especially preferred class of MC monomers is polysiloxanes endcapped with a terminal siloxane moiety that includes a photopolymerizable group. Non-limiting examples of a suitable photopolymerizable group include, but are not limited to acrylate, allyloxy, cinnamoyl, methacrylate, stibenyl, and vinyl. An illustrative representation of such a monomer is:

wherein Y is a siloxane which may be a monomer, a homopolymer or a copolymer formed from any number of siloxane units, and X and $X^1$ may be the same or different and are each independently a terminal siloxane moiety that includes a photopolymerizable group. Non-limiting examples of a suitable photopolymerizable group include, but are not limited to acrylate, allyloxy, cinnamoyl, methacrylate, stibenyl, and vinyl. An illustrative example of Y includes:

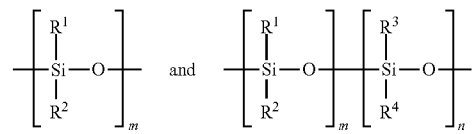

wherein m and n are independently each an integer; and, $R^1$, $R^2$, $R^3$, and $R^4$ are independently each hydrogen, alkyl (substituted, primary, secondary, tertiary, cycloalkyl), aryl, or heteroaryl. In preferred embodiments, $R^1$, $R^2$, $R^3$, and $R^4$ are independently $C_1$-$C_{10}$ alkyl or phenyl. Because MC monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, and $R^3$ are the same and are methyl, ethyl or propyl with the proviso that $R^4$ is phenyl.

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; i and 2,500; 1 and 2,000; 1 and 1,500; 1 and 1,000; 1 and 500 or any range found within any of the aforementioned ranges.

Illustrative examples of $X$ and $X^1$ (or $X^1$ and $X$ depending on how the MC polymer is depicted) are:

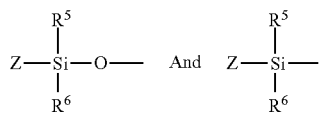

respectively wherein: $R^5$ and $R^6$ are independently each hydrogen, alkyl, aryl, or heteroaryl; and Z is a photopolymerizable group.

In preferred embodiments $R^5$ and $R^6$ are independently each $C_1$-$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ are methyl, ethyl, or propyl and Z is a photopolymerizable group that includes an acrylate or methacrylate moiety.

In some embodiments, a MC macromer has the following formula:

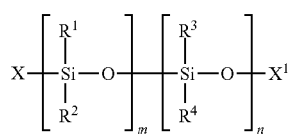

wherein X and $X^1$ are the same as defined above, and wherein $R^1$, $R^2$, $R^3$, and $R^4$ are the same as defined above. In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In general, a suitable modifying composition consists of a lower molecular weight polydimethyl-siloxane macromer containing polymerizable methacrylate functional end groups and a bezoin photoinitiator. In some embodiments, a suitable modifying composition has the following formula.

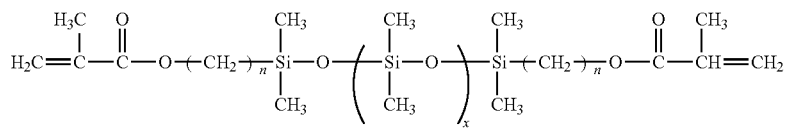

The above structure is a polydimethyl siloxane end-capped with photopolymerizable methacrylate functional groups. In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some embodiments, a suitable modifying composition has the following formula.

Additional illustrative examples of such MC monomers include dimethylsiloxane-diphenylsiloxane copolymer end-capped with a vinyl dimethylsilane group (see below);

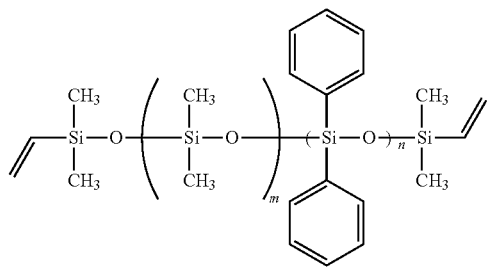

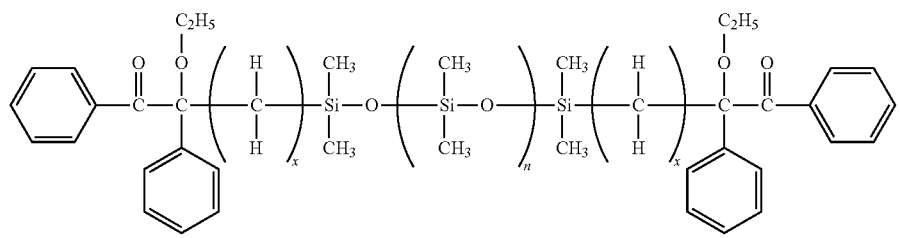

The above modifying composition has a structure comprising a polydimethyl siloxane end-capped with benzoin photoinitiator. In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

Another illustrative examples of such MC monomers includes dimethylsiloxane-methylphenylsiloxane copolymer endcapped with a methacryloxypropyl dimethylsilane group (see below);

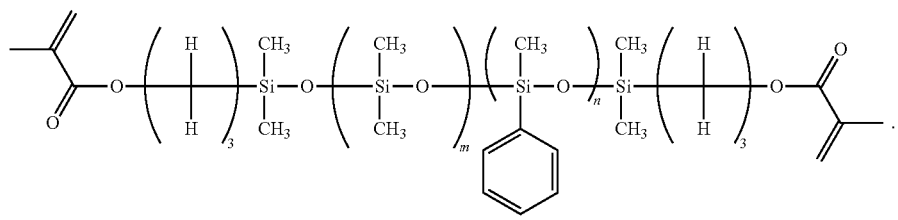

In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000, 1 and 1,500; 1 and 1,000; 1 and 500 or any range found within any of the aforementioned ranges.

Although any suitable method may be used, a ring-opening reaction of one or more cyclic siloxanes in the presence of triflic acid has been found to be a particularly efficient method of making a class of MC monomers. Briefly, the method comprises contacting a cyclic siloxane with a compound of the formula:

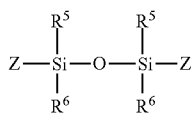

A preferred modifying composition is the dimethylsiloxane macromer endcapped with a methacryloxypropyldimethylsilane group (see below).

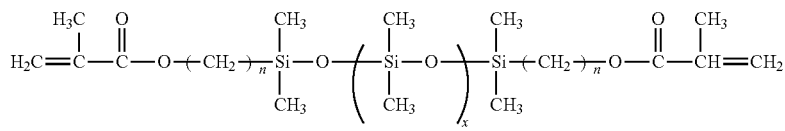

In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and in the presence of triflic acid wherein $R^5$ and $R^6$ are independently each hydrogen, alkyl, aryl, or heteroaryl; and Z is a photopolymerizable group. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxyl-propyl-dimethylsilane group, an especially preferred MC monomer, such as the MC monomer shown below.

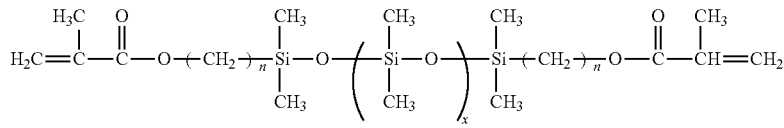

In some examples, x represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, x represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In addition to the silicone-based MCs described above, acrylate-based MC can also be used in the practice of the invention. The acrylate-based macromers of the invention have the general structure wherein X and $X^1$ may be the same or different and/or are each independently a terminal siloxane moiety that includes a photopolymerizable group. Non-limiting examples of a suitable photopolymerizable group include, but are not limited to, acrylate, allyloxy, cinnamoyl, methacrylate, stibenyl, and vinyl

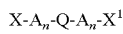

or

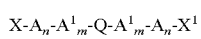

wherein Q is an acrylate moiety capable of acting as an initiator for Atom Transfer Radical Polymerization ("ATRP"), A and $A^1$ have the general structure:

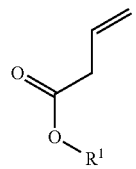

wherein $R^1$ is selected from the group comprising alkyls, halogenated alkyls, aryls and halogenated aryls and X and $X^1$ are groups containing photopolymerizable moieties and m and n are integers. In some examples, m represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, m represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In some examples, n represents an integer having a value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges. In some examples, n represents an integer having an average value between 1 and 10,000; 1 and 9,500; 1 and 9,000; 1 and 8,500; 1 and 8,000; 1 and 7,500; 1 and 7,000; 1 and 6,500; 1 and 6,000; 1 and 5,500; 1 and 5,000; 1 and 4,500; 1 and 4,000; 1 and 3,500; 1 and 3,000; 1 and 2,500; 1 and 2,000; 1 and 1,500; 1 and 1,000; 1 and 500 or any range found within any of the aforementioned ranges.

In one embodiment the acrylate based MC macromer has the formula:

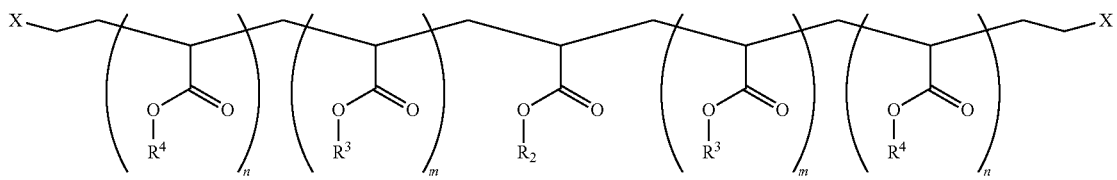

wherein $R^2$ is alkyl or halogenated alkyl; $R^3$ is alkyl, halogenated alkyl, aryl or halogenated aryls; $R^4$ is alkyl, halogenated alkyl, aryl or halogenated aryl; and, with the proviso that $R^3$ and $R^4$ are different. In some embodiments, the value of n is between 1 and 200; 1 and 190; 1 and 180; 1 and 170; 1 and 160; 1 and 150; 1 and 140; 1 and 130; 1 and 120; 1 and 110; 1 and 100; 1 and 90; 1 and 80; 1 and 70; 1 and 60; 1 and 50; 1 and 40; 1 and 30; 1 and 20; 1 and 10; or any range in between. For example, when the value of n is between 1 and 200, this also contemplates a value of n between 17 and 24. In some embodiments the value of m is between 1 and 200; 1 and 190; 1 and 180; 1 and 170; 1 and 160; 1 and 150; 1 and 140; 1 and 130; 1 and 120; 1 and 110; 1 and 100; 1 and 90; 1 and 80; 1 and 70; 1 and 60; 1 and 50; 1 and 40; 1 and 30; 1 and 20; 1 and 10; or any range in between. For example, when the value of m is between 1 and 200, this also contemplates a value of m between 17 and 24.

After the optical element is formed, it is then positioned in the area where the optical properties are to be modified. For an intraocular lens, this means implantation into the eye using known procedures. Once the element is in place and is allowed to adjust to its environment, it is then possible to modify the optical properties of the element through exposure to an external stimulus.

The nature of the external stimulus can vary but it must be capable of reducing polymerization of the MC without adversely affecting the properties of the optical element. Typical external stimuli that can be used in practice of the invention include heat and light, with light preferred. In the case of intraocular lenses, ultraviolet or infrared radiation is preferred with ultraviolet light most preferred.

When the element is exposed to the external stimulus, the MC polymerization forms a second polymer matrix, interspersed within the first polymer matrix. When the polymerization is localized or when only a portion of the MC is polymerized, there is a difference in the chemical potential between the reacted and unreacted regions of the lens. The MC then migrates within the element to reestablish the thermodynamic equilibrium within the optical element.

The formation of the second polymer matrix and the re-distribution of the MC can each affect the optical properties of the element. For example, the formation of the second polymer matrix can cause changes in the refractive index of the element. The migration of the modifying compound can alter the overall shape of the element, further affecting the optical properties by changing the radii of curvatures of the optical element.

Figure 5:
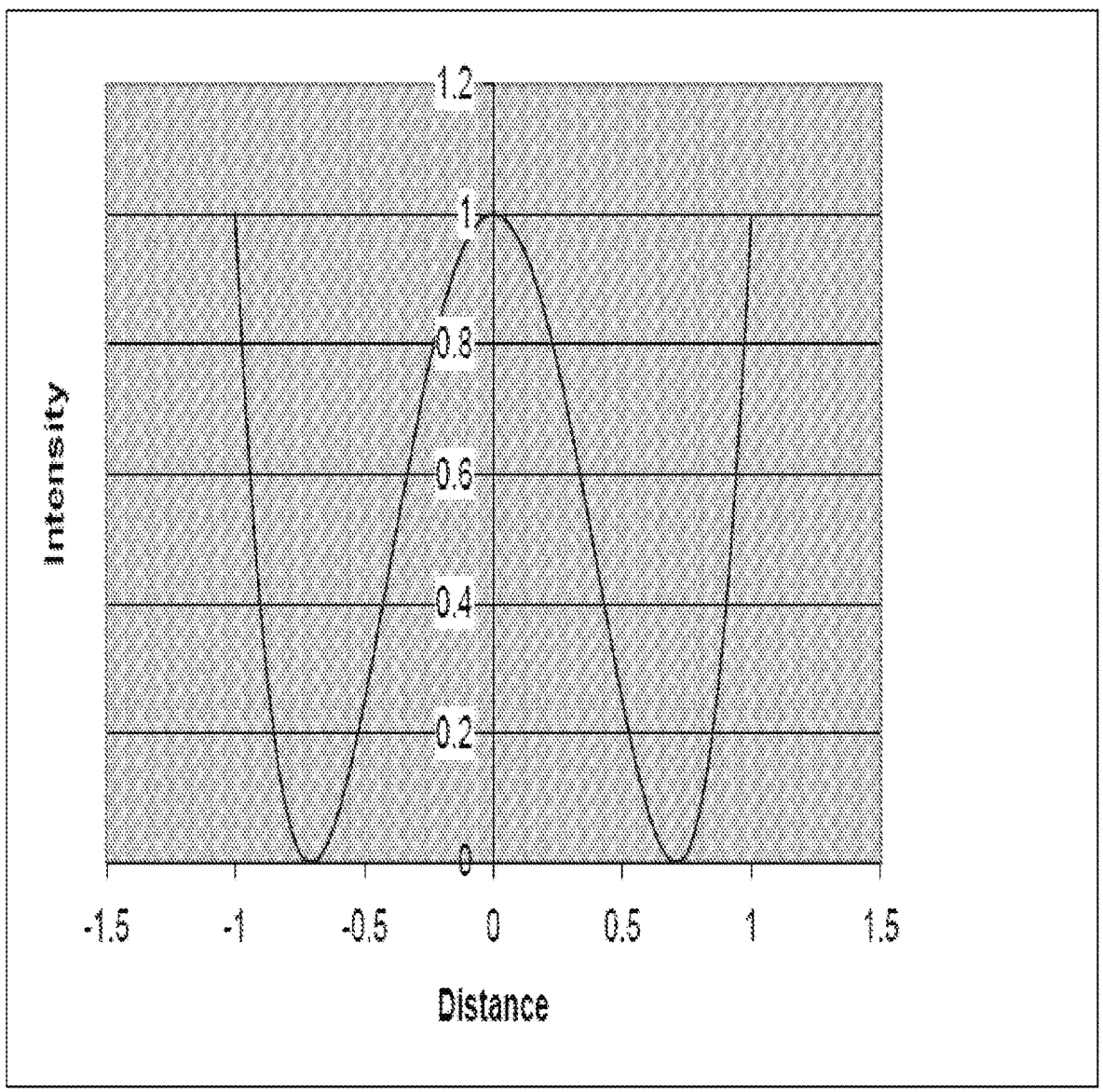
FIG. 5 shows a plot of the aspheric function described in Equation 1.

It is possible to expose the optical element to a spatially defined irradiance profile to create a lens with different optical properties. In one embodiment, it is possible to create an intraocular lens that can be converted into an aspheric lens after implantation. This is accomplished by exposing the lens to a mathematically defined spatial irradiance profile. An example of the type of profiles that can be used to induce asphericity in the lens are of the form $$Asph(\rho) = A\rho^4 - B\rho^2 + 1 \quad (1)$$

where A and B are coefficients and $\rho$ is a radial coordinate. A normalized plot of this function, where A=B=4, is displayed in FIG. 5.

Figure 6:
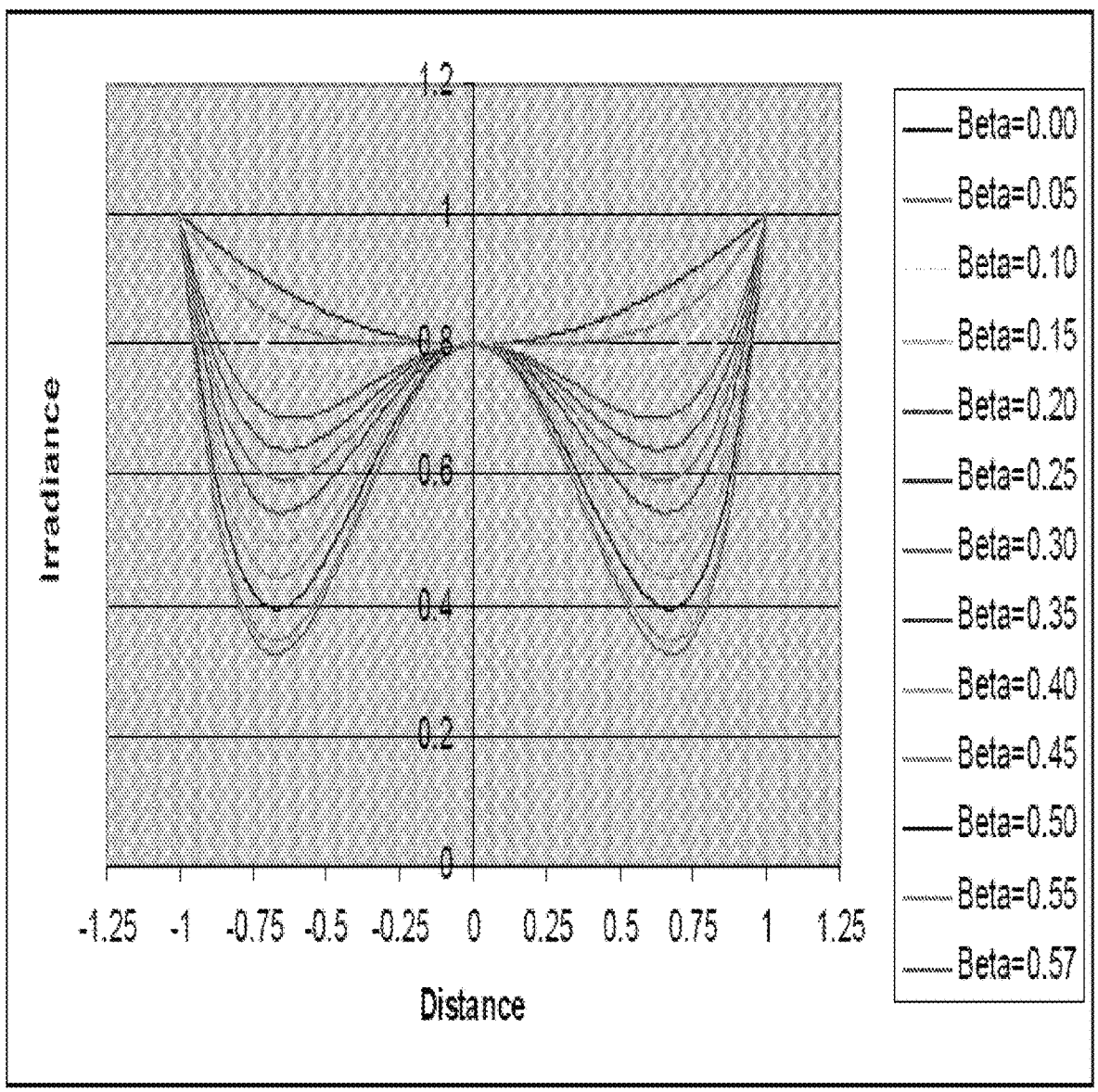
FIG. 6 shows cross-sectional plots of Equation 2 generated by combining a power neutral profile with weighted amounts ($\beta=0$ to $0.57$) of the aspheric profile.

Another approach is to linearly combine weighted amounts of the profile (Asph) displayed in equation 1 with spatial irradiance profiles that are currently used to correct for spherical refractive errors and spherocylindrical refractive errors as well as with Power Neutral Profiles, i.e., profiles that neither add or subtract refractive power from the LAL. This approach has the dual benefits of correcting the lower aberrations, e.g. sphere and cylinder, along with imparting the requisite amount of induced asphericity to provide increased depth of focus. This can be described mathematically as follows:

$$\text{Profile}(\rho) = SCN(\rho) + \beta Asph(\rho) \quad (2)$$

where $SCN(\rho)$ refers to either a spherical, spherocylindrical or power neutral spatial irradiance profile, $Asph(\rho)$ is the same as in equation 1, and $\beta$ is a weighting factor that can range from 0 to 1. As an example of this approach, consider the cross-sectional profiles shown in FIG. 6. These plots were generated by combining weighted amounts of the profile represented by equation 1 with a power neutral profile.

By way of a reaction sequence, the following example shows how the formation of the second polymer matrix and the re-distribution of the MC is accomplished. In the example provided below, the MC having the formula:

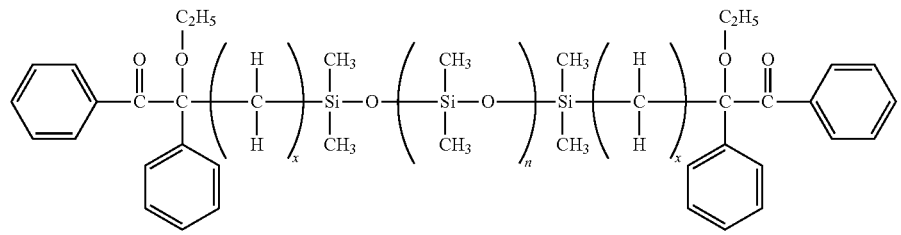

is exposed to UV light, thereby creating a radical species. This process is represented schematically in the reaction scheme below.

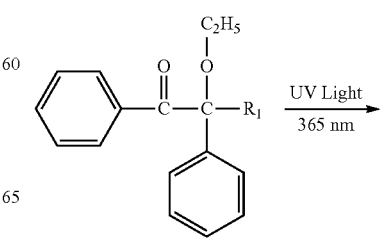

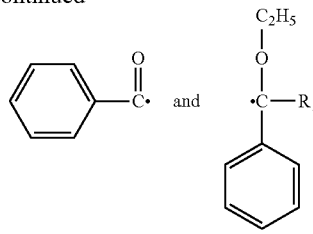 and 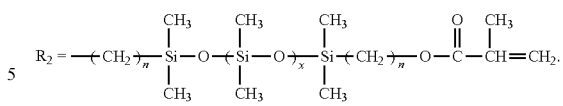

After exposing the MC to UV light, the resulting radical species are free to react with the first polymer matrix. In the example, below the first polymer matrix was formed using a polymer having the following structure:

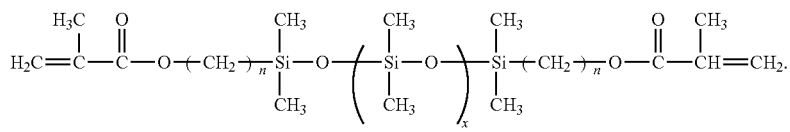

The radical species generated by exposing the MC to UV light then reacts with the first polymer matrix according to the reaction scheme below:

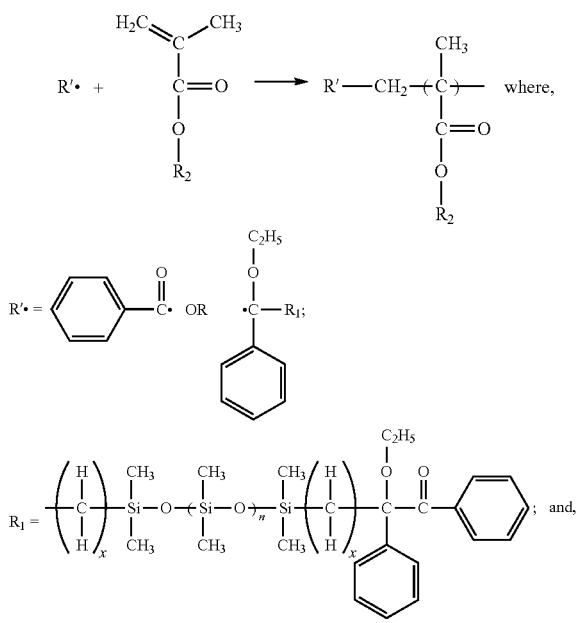

The reaction scheme for photopolymerization of photo-reactive MC in the presence of the first polymer lens matrix is the same for the adjustment and lock-in procedures. The difference between the adjustment procedure and lock-in procedure is the spatial irradiance profiles applied to each procedure.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 7:
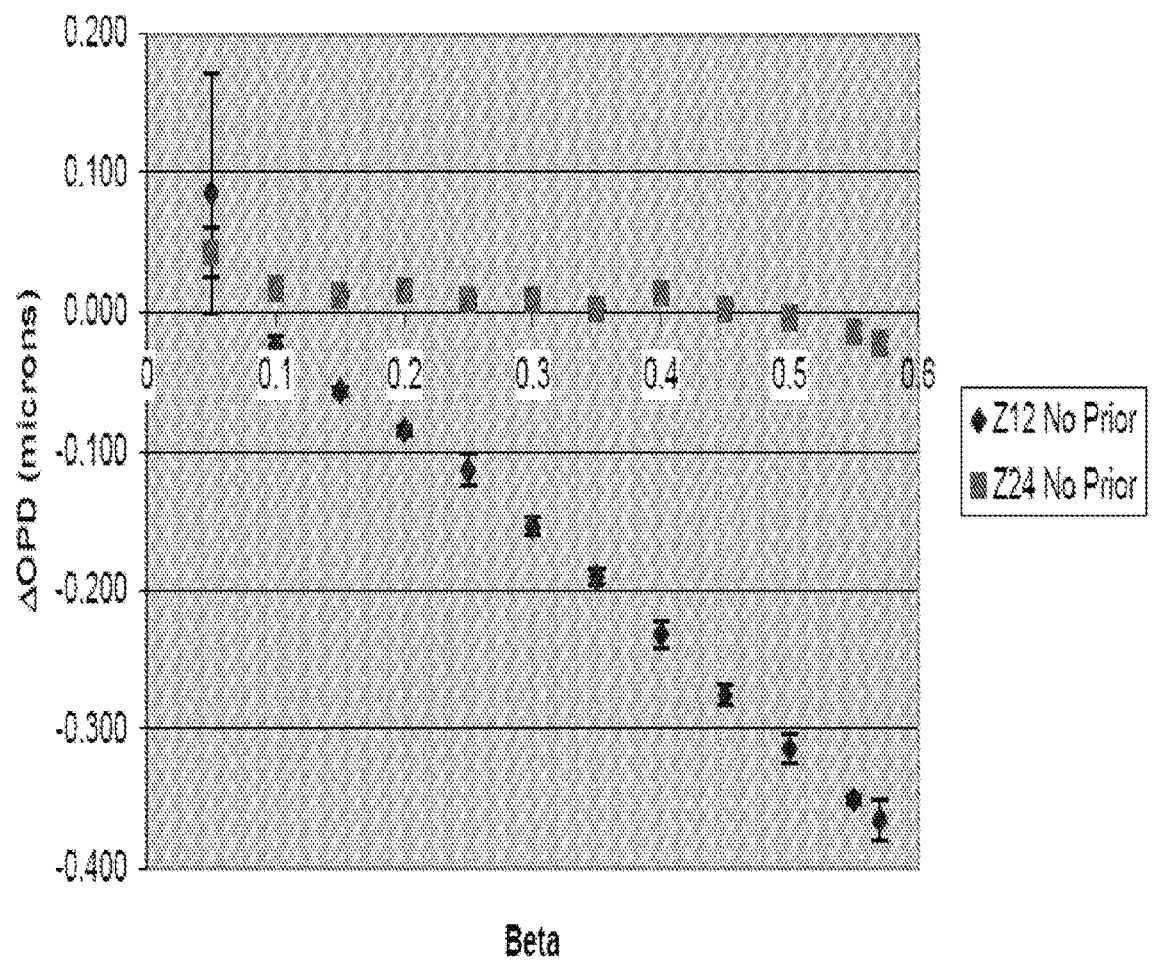
FIG. 7 shows a plot of induced $4^{th}$ and $6^{th}$ order spherical aberration as a function of increasing $\beta$ value. The measurement aperture was 4 mm and none of these LALs received any type of prior adjustment.

A series of light adjustable lenses containing a silicone-based MC were prepared using standard molding techniques known to those skilled in the art. The lens had a first polymer matrix prepared from a silicone hydride crosslinked vinyl endcapped diphenylsiloxane dimethylsiloxane. The first polymer matrix comprised about 70 weight % of the lens. The lens also comprised about 30 weight % of a MC (methacrylate endcapped polydimethylsiloxane), 1 weight % (based on MC) of a photoinitiator (benzoin-tetrasiloxane-benzoin), and 0.04 weight % (based on MC) UV absorber. The lenses had an initial nominal power of +20.0 diopters. Twelve groups, of four LALs each, were exposed to a spatial irradiance profile defined by Equation 2 with beta values ranging from 0.05 to 0.57. Table 1 summarizes the specific spatial irradiance profile, average irradiance, and time applied to each of the LAL groups. At 48 hours post irradiation, the wavefronts of each of the lenses was measured. The measured $4^{th}$ (Z12) and $6^{th}$ (Z24) order spherical aberration values for each of the 12 irradiation groups were averaged together and plotted as a function of increasing $\beta$ value as show in FIG. 7.

TABLE 1

Summary of treatment conditions and induced spherical aberration for those lenses that did not receive a prior adjustment. The measurement aperture was 4 mm for all spherical aberration measurements.

| Lens ID | Profile | Duration (sec) | Applied Power (mW) | Bm Size (mm) | Δ4th Order SA Δ Z12 (μm) | Δ 6th Order SA Δ Z24 (μm) |
|---|---|---|---|---|---|---|
| 6699 | In-vitro PN Profile + Beta = 0.05 | 90 | 4.130 | 5.30 | 0.194 | 0.016 |
| 6701 | In-vitro PN Profile + Beta = 0.05 | 90 | 4.130 | 5.30 | 0.115 | 0.050 |
| 6706 | In-vitro PN Profile + Beta = 0.05 | 90 | 4.130 | 5.30 | 0.003 | 0.054 |
| 6708 | In-vitro PN Profile + Beta = 0.05 | 90 | 4.130 | 5.30 | 0.029 | 0.053 |
| Average | | | | | 0.085 | 0.043 |
| St Dev | | | | | 0.087 | 0.018 |
| 189-26 | In-vitro PN Profile + Beta = 0.10 | 90 | 3.820 | 5.30 | −0.019 | 0.017 |
| 189-29 | In-vitro PN Profile + Beta = 0.10 | 90 | 3.820 | 5.30 | −0.024 | 0.017 |
| 189-31 | In-vitro PN Profile + Beta = 0.10 | 90 | 3.820 | 5.30 | −0.020 | 0.016 |
| 189-33 | In-vitro PN Profile + Beta = 0.10 | 90 | 3.820 | 5.30 | −0.036 | 0.013 |
| Average | | | | | −0.025 | 0.016 |
| St. Dev | | | | | 0.008 | 0.002 |
| 189-27 | In-vitro PN Profile + Beta = 0.15 | 90 | 3.670 | 5.30 | −0.056 | 0.013 |
| 189-30 | In-vitro PN Profile + Beta = 0.15 | 90 | 3.670 | 5.30 | −0.055 | 0.013 |
| 189-32 | In-vitro PN Profile + Beta = 0.15 | 90 | 3.670 | 5.30 | −0.054 | 0.012 |
| 189-34 | In-vitro PN Profile + Beta = 0.15 | 90 | 3.670 | 5.30 | −0.060 | 0.010 |
| Average | | | | | −0.056 | 0.012 |
| St. Dev | | | | | 0.003 | 0.001 |
| 189-35 | In-vitro PN Profile + Beta = 0.20 | 90 | 3.510 | 5.30 | −0.088 | 0.018 |
| 189-38 | In-vitro PN Profile + Beta = 0.20 | 90 | 3.510 | 5.30 | −0.088 | 0.013 |
| 189-40 | In-vitro PN Profile + Beta = 0.20 | 90 | 3.510 | 5.30 | −0.083 | 0.018 |
| 189-44 | In-vitro PN Profile + Beta = 0.20 | 90 | 3.510 | 5.30 | −0.081 | 0.013 |
| Average | | | | | −0.085 | 0.015 |
| St. Dev | | | | | 0.003 | 0.003 |
| 189-37 | In-vitro PN Profile + Beta = 0.25 | 90 | 3.360 | 5.30 | −0.107 | 0.013 |
| 189-39 | In-vitro PN Profile + Beta = 0.25 | 90 | 3.360 | 5.30 | −0.111 | 0.006 |
| 189-41 | In-vitro PN Profile + Beta = 0.25 | 90 | 3.360 | 5.30 | −0.106 | 0.009 |
| 189-45 | In-vitro PN Profile + Beta = 0.25 | 90 | 3.360 | 5.30 | −0.130 | 0.006 |
| Average | | | | | −0.113 | 0.009 |
| St. Dev | | | | | 0.011 | 0.003 |
| 185-3-2 | In-vitro PN Profile + Beta = 0.30 | 90 | 3.210 | 5.30 | −0.151 | 0.010 |
| 185-3-15 | In-vitro PN Profile + Beta = 0.30 | 90 | 3.210 | 5.30 | −0.156 | 0.008 |
| 188-2-18 | In-vitro PN Profile + Beta = 0.30 | 90 | 3.210 | 5.30 | −0.163 | 0.012 |
| 189-47 | In-vitro PN Profile + Beta = 0.30 | 90 | 3.210 | 5.30 | −0.148 | 0.007 |
| Average | | | | | −0.155 | 0.009 |
| St. Dev | | | | | 0.007 | 0.002 |
| 185-3-11 | In-vitro PN Profile + Beta = 0.35 | 90 | 3.060 | 5.30 | −0.193 | 0.005 |
| 188-2-16 | In-vitro PN Profile + Beta = 0.35 | 90 | 3.060 | 5.30 | −0.194 | 0.003 |
| 189-46 | In-vitro PN Profile + Beta = 0.35 | 90 | 3.060 | 5.30 | −0.192 | 0.002 |
| 189-48 | In-vitro PN Profile + Beta = 0.35 | 90 | 3.060 | 5.30 | −0.182 | 0.002 |
| Average | | | | | −0.190 | 0.003 |
| St. Dev | | | | | 0.006 | 0.002 |
| 6700 | In-vitro PN Profile + Beta = 0.40 | 90 | 2.900 | 5.30 | −0.240 | 0.013 |
| 6704 | In-vitro PN Profile + Beta = 0.40 | 90 | 2.900 | 5.30 | −0.241 | 0.011 |
| 6707 | In-vitro PN Profile + Beta = 0.40 | 90 | 2.900 | 5.30 | −0.222 | 0.011 |
| 6709 | In-vitro PN Profile + Beta = 0.40 | 90 | 2.900 | 5.30 | −0.224 | 0.017 |
| Average | | | | | −0.232 | 0.013 |
| St. Dev | | | | | 0.010 | 0.003 |
| 6710 | In-vitro PN Profile + Beta = 0.45 | 90 | 2.750 | 5.39 | −0.277 | 0.004 |
| 6712 | In-vitro PN Profile + Beta = 0.45 | 90 | 2.750 | 5.30 | −0.284 | 0.003 |
| 6715 | In-vitro PN Profile + Beta = 0.45 | 90 | 2.750 | 5.30 | −0.274 | 0.006 |
| 6717 | In-vitro PN Profile + Beta = 0.45 | 90 | 2.750 | 5.30 | −0.266 | −0.002 |
| Average | | | | | −0.275 | 0.003 |
| St. Dev | | | | | 0.007 | 0.003 |
| 6713 | In-vitro PN Profile + Beta = 0.50 | 90 | 2.600 | 5.30 | −0.303 | 0.001 |
| 6716 | In-vitro PN Profile + Beta = 0.50 | 90 | 2.600 | 5.30 | −0.322 | −0.002 |
| 6718 | In-vitro PN Profile + Beta = 0.50 | 90 | 2.600 | 5.30 | −0.318 | −0.009 |
| Average | | | | | −0.314 | −0.003 |
| St. Dev | | | | | 0.010 | 0.005 |
| 6719 | In-vitro PN Profile + Beta = 0.55 | 90 | 2.440 | 5.30 | −0.358 | −0.009 |
| 6723 | In-vitro PN Profile + Beta = 0.55 | 90 | 2.440 | 5.30 | −0.347 | −0.016 |
| 6727 | In-vitro PN Profile + Beta = 0.55 | 90 | 2.440 | 5.30 | −0.350 | −0.011 |
| 6729 | In-vitro PN Profile + Beta = 0.55 | 90 | 2.440 | 5.30 | −0.350 | −0.021 |
| Average | | | | | −0.351 | −0.014 |
| St. Dev | | | | | 0.004 | 0.006 |
| 6721 | In-vitro PN Profile + Beta = 0.57 | 90 | 2.380 | 5.30 | −0.368 | −0.015 |
| 6725 | In-vitro PN Profile + Beta = 0.57 | 90 | 2.380 | 5.30 | −0.350 | −0.026 |

TABLE 1-continued

Summary of treatment conditions and induced spherical aberration for those lenses that did not receive a prior adjustment. The measurement aperture was 4 mm for all spherical aberration measurements.

| Lens ID | Profile | Duration (sec) | Applied Power (mW) | Bm Size (mm) | Δ 4th Order SA Δ Z12 (μm) | Δ 6th Order SA Δ Z24 (μm) |
|---|---|---|---|---|---|---|
| 6728 | In-vitro PN Profile + Beta = 0.57 | 90 | 2.380 | 5.30 | −0.359 | −0.019 |
| 6730 | In-vitro PN Profile + Beta = 0.57 | 90 | 2.380 | 5.30 | −0.385 | −0.030 |
| Average | | | | | −0.366 | −0.022 |
| St. dev | | | | | 0.015 | 0.007 |

Inspection of the plot indicates several interesting features. The first is the nearly linearly increase in induced $4^{th}$ order spherical aberration as a function of increasing β value. The second feature is the nearly complete absence of any $6^{th}$ order spherical aberration induction, indicating that the induced spherical aberration is essentially pure $4^{th}$ order spherical aberration. This is important because it has been shown that the presence of $6^{th}$ order spherical aberration will have the affect of nulling out any induced depth of focus produced by the induction of negative $4^{th}$ order spherical aberration. (Thibos el al., 2004) The third feature to note is the small standard deviation in the average, induced $4^{th}$ order spherical aberration for a specific β value. This fact indicates that it is possible to adjust the amount of asphericity in the LAL by targeted, discrete values, which will allow true customization of patients' depth of focus. And finally, as written above, the targeted amount of total ocular $4^{th}$ order spherical aberration for optimizing visual acuity between 40 cm and distance emmetropia is −0.125 μm. Inspection of the data in Table 2 and FIG. 7 and assuming an average starting ocular spherical aberration at a 4 mm aperture of +0.10 μm, indicates that the profile with a beta value of 0.40 would be ideal for inducing the requisite amount of negative asphericity.

The above example involved irradiating LALs that had not received a prior adjustment. However, there will be instances where it is necessary to first adjust the spherical and/or spherocylindrical power of the LAL before the aspheric adjustment. The LAL is a closed thermodynamic system, i.e. we can't add or remove particles, MC, from the lens. As a consequence, each subsequent refractive adjustment consumes MC leaving less for subsequent adjustments. In addition, upon polymerization of MC during adjustment, the polymerized MC forms an interpenetrating matrix with the host matrix polymer. This action has the effect of increasing the stiffness of the lens. Because the refractive change, i.e. spherical, spherocylindrical, aspheric, etc., of the LAL is accomplished by a shape change, the amount of induced asphericity after an initial adjustment should be reduced for same treatment conditions as with the no prior adjustment cases summarized in FIG. 7.

Figure 8:
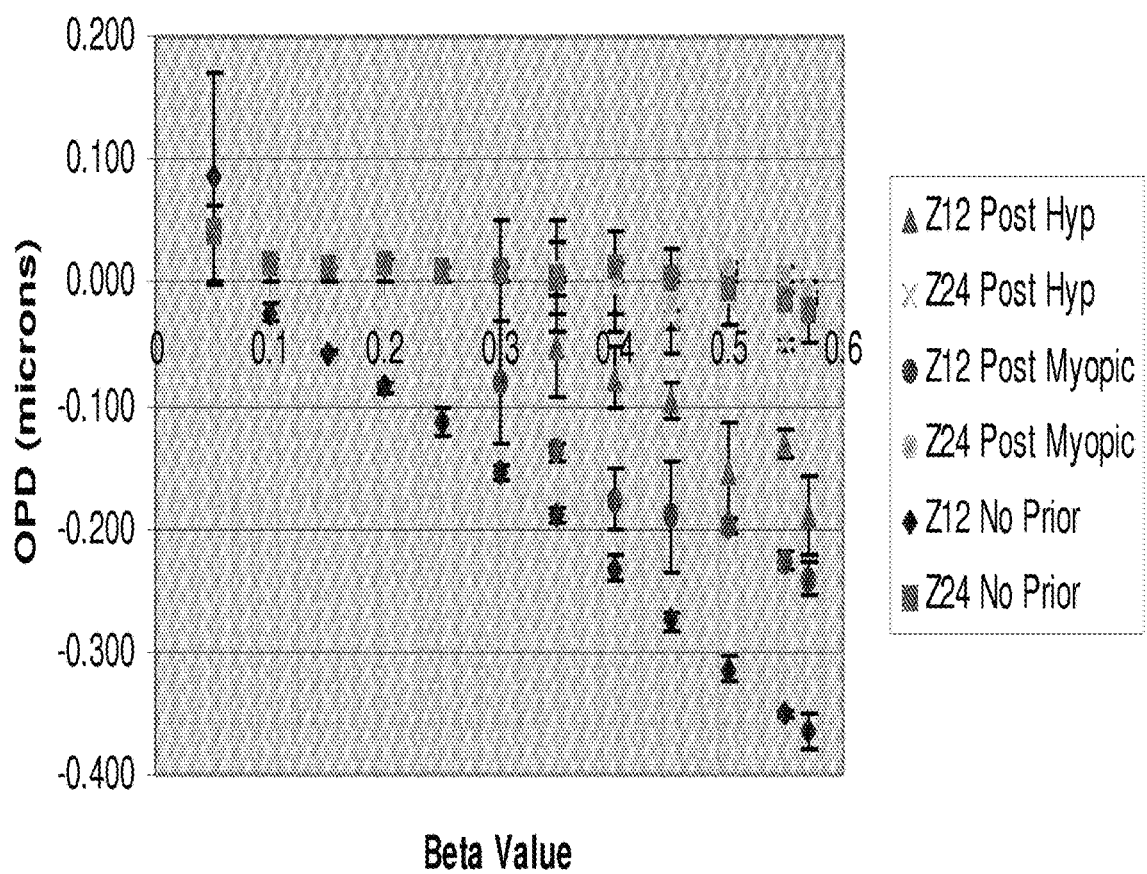
FIG. 8 shows a plot of induced $4^{th}$ and $6^{th}$ order spherical aberration as a function of increasing $\beta$ value for LALs receiving a hyperopic, myopic, and no prior adjustment. The measurement aperture for both the $4^{th}$ and $6^{th}$ order spherical aberration was 4 mm.

To investigate this, a series of LALs were initially given either a myopic or hyperopic primary adjustment followed by an aspheric treatment 48 hours post the initial, primary adjustment. FIG. 8 displays both the $4^{th}$ and $6^{th}$ order spherical aberration values for LALs that received either an initial hyperopic or myopic adjustment followed by an aspheric treatment with beta values ranging between 0.30 and 0.57. For comparison, the LALs that received the aspheric treatment as a primary adjustment are also plotted on the same graph.

Inspection and comparison of the data for the different treatment conditions indicate several interesting trends. The first overall theme is that, as expected, increasing the beta value, which effectively increases the amount of aspheric character of the treatment beam, has the effect of increasing the amount of induced $4^{th}$ order asphericity in the LAL. This is true whether the LAL initially received a primary adjustment or if the LAL has received no prior adjustment. The second thing to note is that for a given beta, mediated aspheric profile, the type of refractive adjustment preceding the aspheric treatment directly impacts how much $4^{th}$ order asphericity is induced in the lens. For example, consider the three different sets of LALs that were adjusted with the β=0.57 aspheric profile after a hyperopic adjustment, a myopic adjustment, and no adjustment. Inspection of the graph indicates that those lenses receiving no prior adjustment displayed the largest amount of induced $4^{th}$ order spherical aberration, followed by the LALs that initially received a myopic adjustment, with the LALs after a hyperopic adjustment showing the smallest amount of induced asphericity. The reasons for this general trend are twofold. The first, which was discussed above, is due to the simple fact that the LALs that received no prior adjustment obviously have more starting MC and the LAL matrix is not as stiff as compared to the other two sets of LALs and thus, for the same given aspheric dose, should show more $4^{th}$ order asphericity induction. The reasons why the LALs receiving an initial myopic adjustment display greater amounts of induced $4^{th}$ order spherical aberration as compared to those LALs receiving a hyperopic adjustment as their primary adjustment, even though the magnitude of the refractive change (−1.0 D vs+1.0 D) is the same, can be explained by the fact that the total energy underneath the spatial irradiance profile for the given myopic adjustment is less than that as compared to the hyperopic adjustment profile. Because of this fact, more macromer will be consumed during the initial hyperopic adjustment and a stronger, interpenetrating network will be formed, thus preventing more aspheric induction. Another important aspect of the data to note, is that regardless of prior adjustment, the application of the aspheric treatment does not induce any $6^{th}$ order spherical aberration.

Example 2

Figure 9:
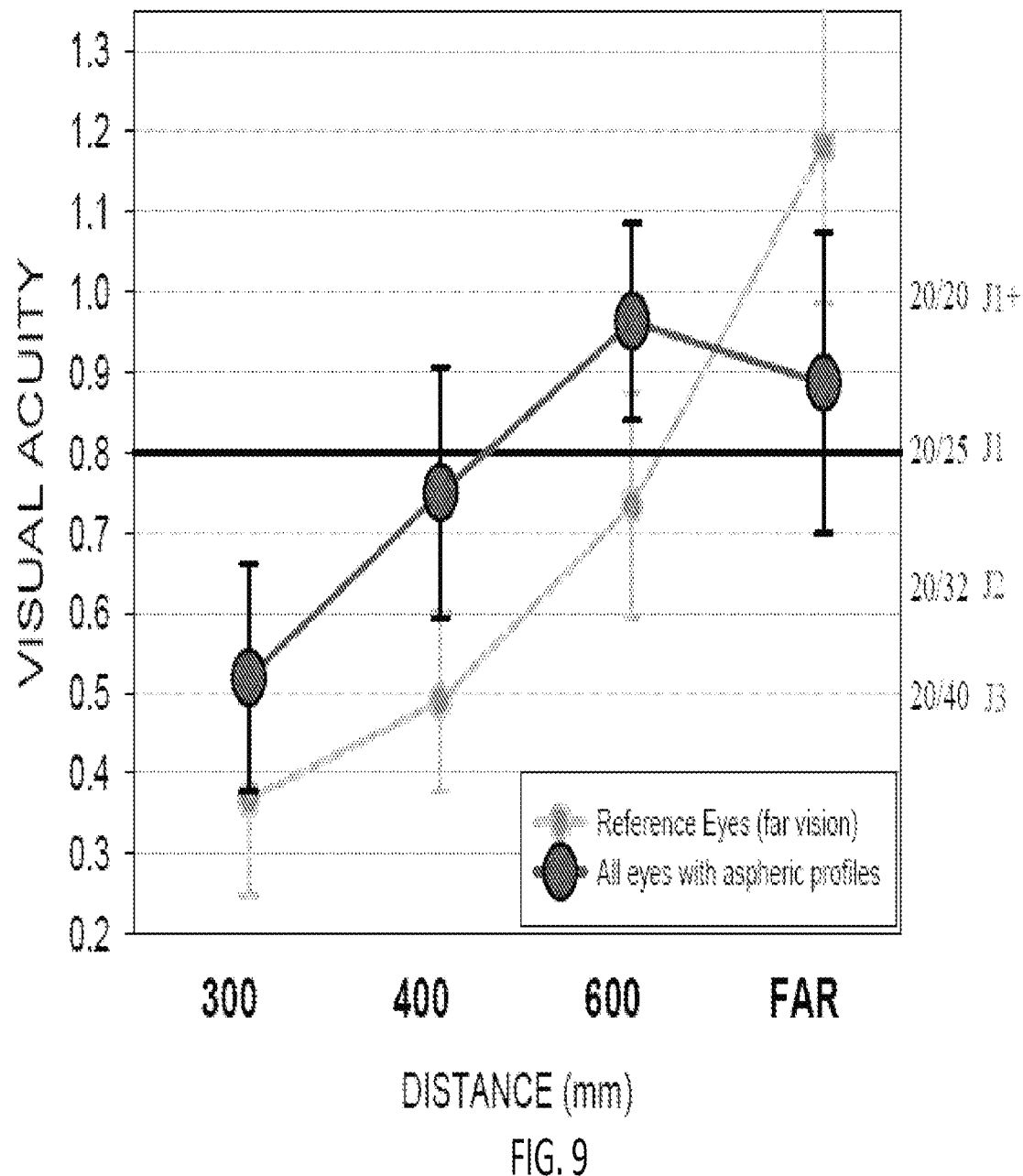
FIG. 9 shows the monocular visual acuity data for eyes receiving an initial refractive adjustment followed by an aspheric treatment (n=32) versus those eyes treated only for distance emmetropia (n=12).

To test the ability of the aspheric adjustment profiles to induce enough asphericity to provide patients with increased depth of focus, a series of subjects were implanted with the light adjustable lens after routine cataract surgery, given a prior treatment to correct for postoperative residual sphere and cylinder, and then given an aspheric adjustment using the corneal compensated versions of the profiles described in Example 1. FIG. 9 and Table 2 summarize the monocular visual acuity data for a series of 32 eyes adjusted with aspheric profiles possessing a beta value between 0.40 and 0.57. For comparison, the average uncorrected visual acuity values for 12 eyes implanted with a LAL and adjusted for distance emmetropia only, are displayed as well. All of the LALs received some type of primary adjustment before the application of the aspheric profile.

Inspection of the graph in FIG. 9 indicates several important features. The first is that, on average, from 40 cm to distance emmetropia, the patients adjusted with an aspheric treatment profile possessed uncorrected visual acuities between 20/20 and 20/32. In fact, as summarized in Table 2, 75% of the eyes treated with the aspheric profile treatment regimen, possess an uncorrected visual acuity of 20/32 or better from 40 cm to distance emmetropia. In contrast, inspection of the results for those eyes receiving treatment to correct for residual spherical and spherocylindrical refractive errors, only, show that while the distance, uncorrected visual acuity results are better than the aspheric cases (83%>20/20 and 100%>20/25 or better), these eyes, as expected, have essentially no near vision capability, i.e. 8% (1/12) see at least 20/32 at 40 cm. Therefore, this data indicates that the application of the aspheric profiles to implanted LALs has the ability to increase the depth of focus of a patients' eye.

TABLE 2

Monocular visual acuity (VA) results for those eyes receiving an aspheric treatment (n = 32).

| VA | FAR | 60 cm | 40 cm | Far BCVA |
|---|---|---|---|---|
| ≥20/20 | 9/32 (28%) | 17/32 (53%) | 2/32 (6%) | 21/32 (65%) |
| ≥20/25 | 23/32 (72%) | 27/32 (84%) | 11/32 (35%) | 31/32 (97%) |
| ≥20/32 | 28/32 (88%) | 32/32 (100%) | 24/32 (75%) | 32/32 (100%) |
| ≥20/40 | 32/32 (100%) | 32/32 (100%) | 31/32 (97%) | 32/32 (100%) |
| ≥20/60 | 32/32 (100%) | 32/32 (100%) | 32/32 (100%) | 32/32 (100%) |

TABLE 3

Monocular visual acuity (VA) results for those LAL eyes adjusted for distance visual acuity only (n = 12).

| VA | FAR | 60 cm | 40 cm | Far BCVA |
|---|---|---|---|---|
| ≥20/20 | 10/12 (83%) | 1/12 (8%) | 0/12 (0%) | 12/12 (100%) |
| ≥20/25 | 12/12 (100%) | 3/12 (25%) | 0/12 (0%) | 12/12 (100%) |
| ≥20/32 | 12/12 (100%) | 8/12 (67%) | 1/12 (8%) | 12/12 (100%) |
| ≥20/40 | 12/12 (100%) | 12/12 (100%) | 7/12 (58%) | 12/12 (100%) |
| ≥20/60 | 12/12 (100%) | 12/12 (100%) | 12/12 (100%) | 12/12 (100%) |

Figure 10:
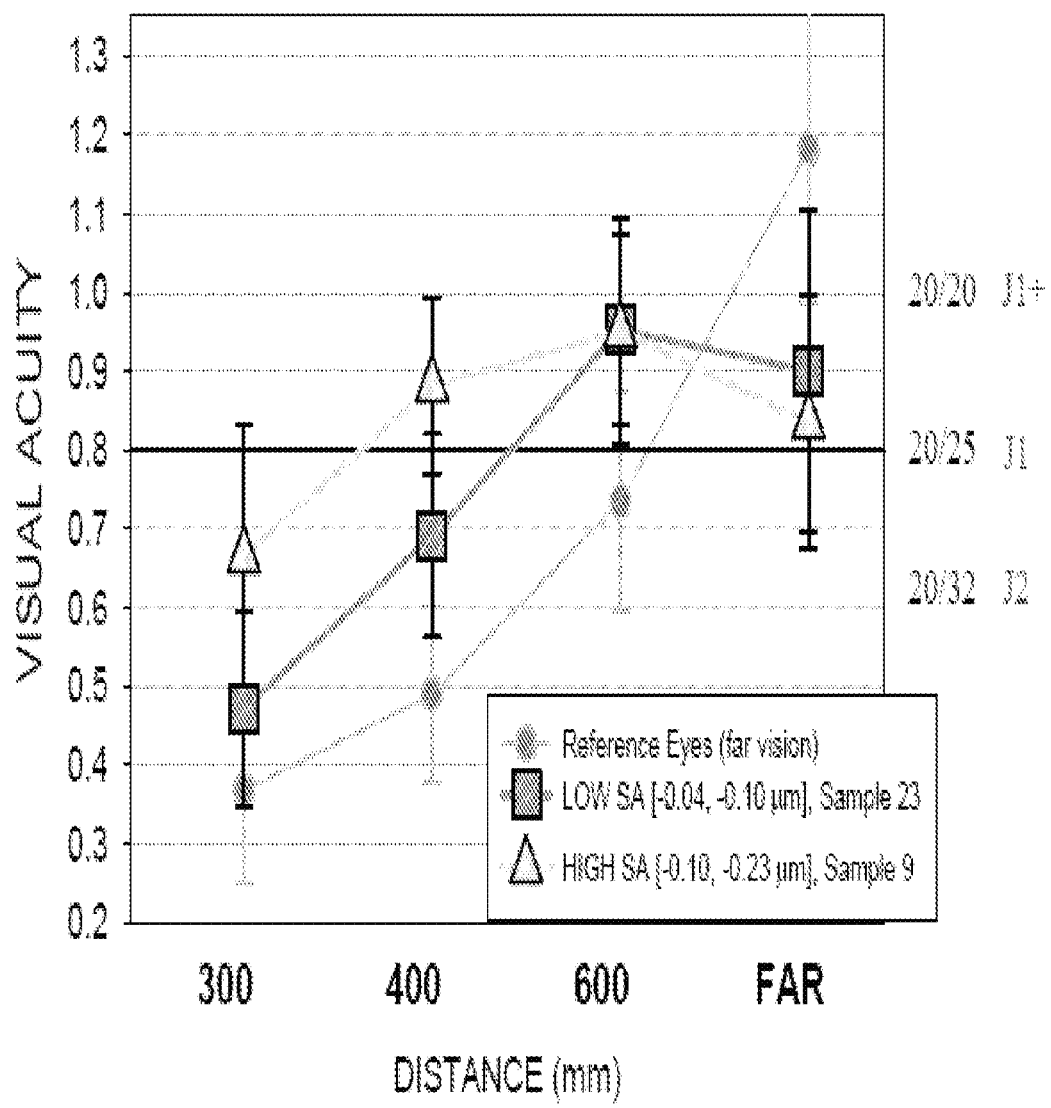
FIG. 10 shows the segregation of the monocular visual acuity data into high (n=9) and low (n=23) induced spherical aberration values. For comparison, those eyes (n=12) adjusted for distance emmetropia are also shown.

As indicated in FIG. 9, the total measured $4^{th}$ order spherical aberration over a 4 mm pupil in the 32 eyes ranged from −0.04 μm to −0.23 μm. As stated above, theoretical considerations indicate that the ideal amount of final $4^{th}$ order spherical aberration to provide optimal visual acuity between 40 cm and distance emmetropia is −0.125 μm. To consider the impact of this range of induced negative asphericity on the final Visual acuities at different object distances, FIG. 10 segregates the 32 eyes into two groups: High Spherical Aberration (−0.10 μm to −0.23 μm) and Low Spherical Aberration (−0.04 μm to −0.10 μm). As expected, those eyes with higher amounts of induced negative spherical aberration, on average, show better visual acuities at 40 cm (78% 7/9 patients ≥20/25 or J1) then those with lower spherical aberration (22%, 5/23 patients ≥20/25 or J1) with a slight decrease in their distance visual acuities (56% vs 78% at 20/25). However, inspection of the VA acuity curves from 40 cm to distance emmetropia in FIG. 10, indicate that, on average, the curve is quite flat and the majority of the eyes possess visual acuities of 20/25 or better. Comparison again with the 12 eyes adjusted for distance emmetropia only, indicates that from 40 cm to distance emmetropia, the eyes that received some type of aspheric induction achieve much greater range of vision, i.e. increased depth of focus.

TABLE 4

Monocular visual acuity (VA) results for those eyes with low amounts of final $4^{th}$ order spherical aberration, −0.04 to −0.10 μm (n = 23).

| VA | FAR | 60 cm | 40 cm | Far BCVA |
|---|---|---|---|---|
| ≥20/20 (J1+) | 7/23 (30%) | 12/23 (8%) | 0/23 (0%) | 15/23 (65%) |
| ≥20/25 (J1) | 15/23 (74%) | 19/23 (83%) | 5/23 (22%) | 22/23 (96%) |
| ≥20/32 (J2) | 20/23 (100%) | 23/23 (100%) | 15/23 (65%) | 12/12 (100%) |
| ≥20/40 (J3) | 23/23 (100%) | 23/23 (100%) | 23/23 (100%) | 12/12 (100%) |
| ≥20/60 | 23/23 (100%) | 23/23 (100%) | 23/23 (100%) | 12/12 (100%) |

TABLE 5

Monocular visual acuity (VA) results for those eyes with high amounts of final 4th order spherical aberration, −0.11 to −0.23 μm (n = 9).

| VA | FAR | 60 cm | 40 cm | Far BCVA |
|---|---|---|---|---|
| ≥20/20 (J1+) | 2/9 (22%) | 4/9 (8%) | 2/9 (22%) | 6/9 (67%) |
| ≥20/25 (J1) | 5/9 (56%) | 7/9 (78%) | 7/9 (78%) | 8/9 (89%) |
| ≥20/32 (J2) | 8/9 (89%) | 8/9 (89%) | 9/9 (100%) | 9/9 (100%) |
| ≥20/40 (J3) | 9/9 (100%) | 9/9 (100%) | 9/9 (100%) | 9/9 (100%) |
| ≥20/60 | 9/9 (100%) | 9/9 (100%) | 9/9 (100%) | 9/9 (100%) |

Figure 11:
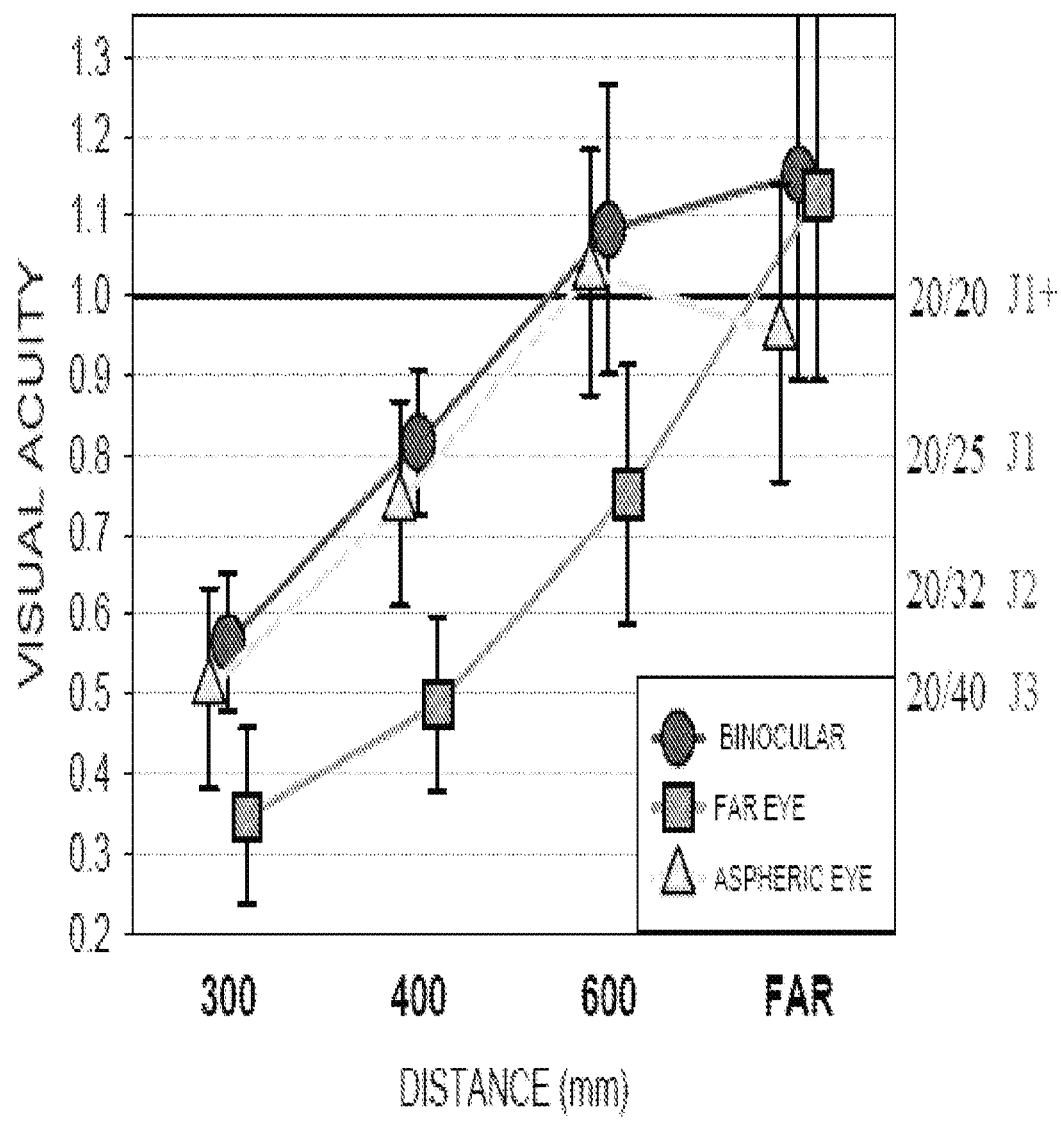
FIG. 11 shows a comparison of the monocular and the binocular visual acuities for a series of patients that were corrected for distance emmetropia in one eye and received an aspheric treatment in their fellow eye. The amount of induced asphericity ranged from −0.04 μm to −0.10 μm, referenced to a 4 mm pupil.
Figure 12:
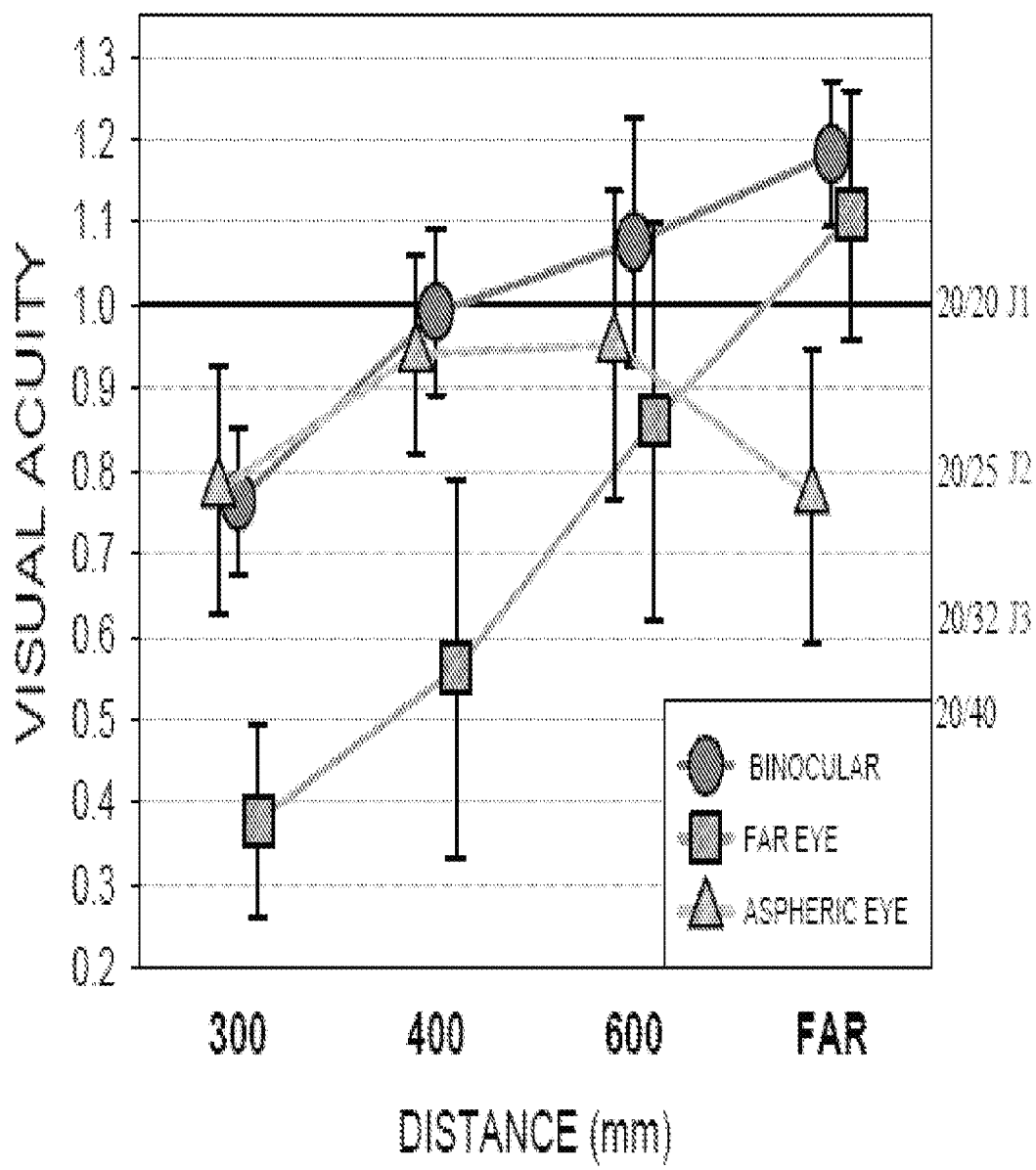
FIG. 12 shows a comparison of the monocular and binocular visual acuities for a series of patients that were corrected for distance emmetropia in one eye and received an aspheric treatment in their fellow eye. The amount of induced asphericity ranged from −0.11 μm to −0.23 μm, referenced to a 4 mm pupil.

The above discussion considered the monocular visual acuities of the treated eyes, only. However, one approach that will optimize post LAL implantation patients' vision at all distances is to correct one of the patients' eyes (usually the dominant eye) to distance emmetropia and then to adjust the other eye of the patient first to distance emmetropia followed by application of the aspheric treatment. As an example of this procedure, consider the data displayed in FIG. 11 and Table 6, which displays both the monocular and binocular visual acuities for a series of patients (n=10) that had a low (−0.04 μm to −0.10 μm) amount of spherical aberration induced in one eye and the other eye was implanted with a LAL and adjusted for distance emmetropia. For the distance dominant eye, the final refraction varied between piano and −0.50 D. Inspection of the monocular visual acuity results for the two eyes displays the same visual characteristics already discussed; namely, the eye corrected for distance emmetropia displays excellent distance visual acuity, but rather poor near vision and the aspheric eyes display improved depth of focus at the expense of some distance visual acuity. However, the binocular visual acuity data indicates that combining the two eyes provide outstanding visual acuities from 40 cm to distance emmetropia. In fact, 100% of the patients possessed a visual acuity of 20/25 or better from 40 cm to distance emmetropia.

TABLE 6

Binocular visual acuity (VA) results for those eyes with low amounts of final 4th order spherical aberration, −0.04 to −0.10 mm in their non-dominant eye and with their other eye adjusted for distance emmetropia. The refraction in the dominant eye ranged from +0.25 D to −0.25 D (n = 10).

| VA | FAR | 60 cm | 40 cm | 30 cm |
|---|---|---|---|---|
| ≥20/20 (J1+) | 6/10 (60%) | 8/10 (80%) | 1/10 (10%) | 0/10 (0%) |
| ≥20/25 (J1) | 10/10 (100%) | 10/10 (100%) | 4/10 (40%) | 0/10 (0%) |
| ≥20/32 (J2) | 10/10 (100%) | 10/10 (100%) | 10/10 (100%) | 3/10 (30%) |
| ≥20/40 (J3) | 10/10 (100%) | 10/10 (100%) | 10/10 (100%) | 8/10 (80%) |
| ≥20/60 | 10/10 (100%) | 10/10 (100%) | 10/10 (100%) | 10/10 (100%) |

Combining this binocular approach with those eyes having high amounts of induced asphericity (−0.11 μm to −0.23 μm), indicates that 100% (4/4) of the patients possessed an uncorrected visual of 20/25 or better from 40 cm to distance emmetropia.

TABLE 7

Binocular visual acuity (VA) results for those eyes with high amounts of final 4th order spherical aberration, −0.11 to −0.23 μm in their non-dominant eye and with their other eye adjusted for distance emmetropia. The refraction in the dominant eye ranged from +0.25 D to −0.25 D (n = 4).

| VA | FAR | 60 cm | 40 cm | 30 cm |
|---|---|---|---|---|
| ≥20/20 (J1+) | 4/4 (100%) | 3/4 (75%) | 1/10 (10%) | 0/4 (0%) |
| ≥20/25 (J1) | 4/4 (100%) | 4/4 (100%) | 4/4 (100%) | 1/4 (25%) |
| ≥20/32 (J2) | 4/4 (100%) | 4/4 (100%) | 4/4 (100%) | 4/4 (100%) |
| ≥20/40 (J3) | 4/4 (100%) | 4/4 (100%) | 4/4 (100%) | 4/4 (100%) |
| ≥20/60 | 4/4 (100%) | 4/4 (100%) | 4/4 (100%) | 4/4 (100%) |

Example 3

General examples disclosed herein include an optical element composed of matrix polymer and a modulating composition (MC) that can be polymerized by an external stimulus (e.g. heat, light, etc) to control the amount of induced asphericity.

In each of the aforementioned examples, the lens may include an optical element that is a lens. In additional examples, the optical element is an intraocular lens (IOL). Also, the amount of induced asphericity is controlled by the application of a specific spatial irradiance profile. In some examples, the amount of induced asphericity is induced monocularly to induce extended depth of focus.

In particular examples, the amount of induced asphericity is tailored to provide intermediate vision (60-80 cm) or near vision (30-40 cm). In specific embodiments, the amount of induced asphericity can be customized for specific individual values.

In certain embodiments, the amount of induced asphericity is induced binocularly to induce extended depth of focus. In particular examples, one eye is tailored for intermediate (60-80 cm) vision by the induction of a particular value of asphericity and the other eye is corrected for distance emmetropia. In alternate embodiments, one eye is tailored for near vision (30-40 cm) by the induction of a particular value of asphericity and the other eye is corrected for distance emmetropia. In further embodiments, both eyes are tailored for intermediate (60-80 cm) vision by the induction of particular value of asphericity. In yet another embodiment, both eyes are tailored for near (30-40 cm) vision by the induction of particular value of asphericity. In some embodiments, one eye is tailored for intermediate (60-80 cm) vision by the induction of negative asphericity and the other eye is tailored for intermediate vision (60-80 cm) vision by the induction of positive asphericity. In particular embodiments, one eye is tailored for near vision (30-40 cm) vision by the induction of negative asphericity and the other eye is tailored for near vision (30-40 cm) vision by the induction of positive asphericity.

In some examples, the amount of induced asphericity of the lens is tailored to compensate for the spherical aberration of the cornea. In other examples, the amount of induced asphericity of both lenses are tailored to compensate for the spherical aberration of their respective corneas. In alternate examples, one lens is adjusted to remove the spherical aberration of the entire eye and the other lens is adjusted to induce asphercity for intermediate vision (60-80 cm). In some examples, one lens is adjusted to remove the spherical aberration of the entire eye and the other lens is adjusted to induce asphercity for near vision (30-40 cm).

Additional Embodiments

Figure 13A:
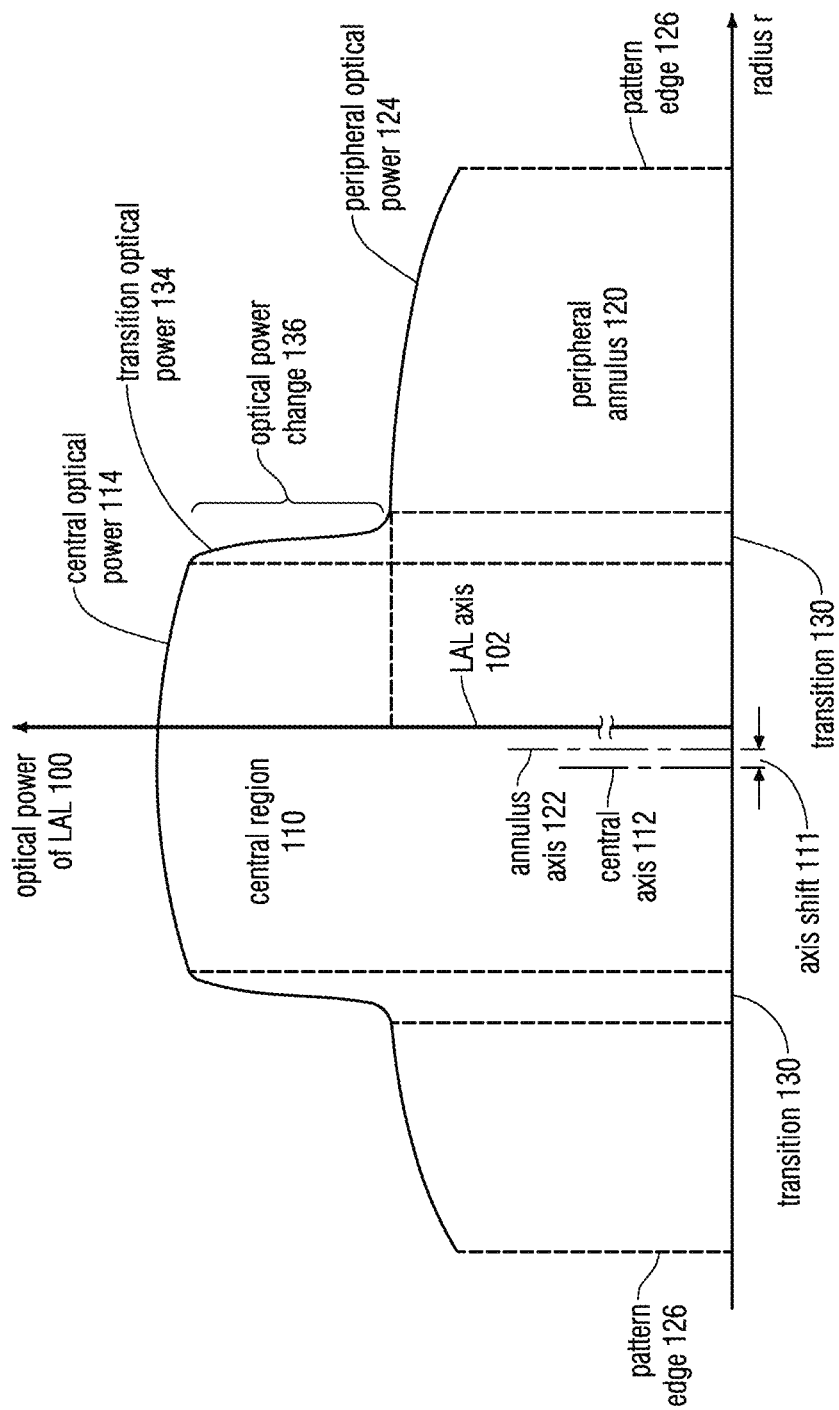
FIGS. 13A-D illustrate a Light Adjustable Lens with position-dependent optical power and shifted axes, and stages of an illumination of the Light Adjustable Lens.
Figure 13B:
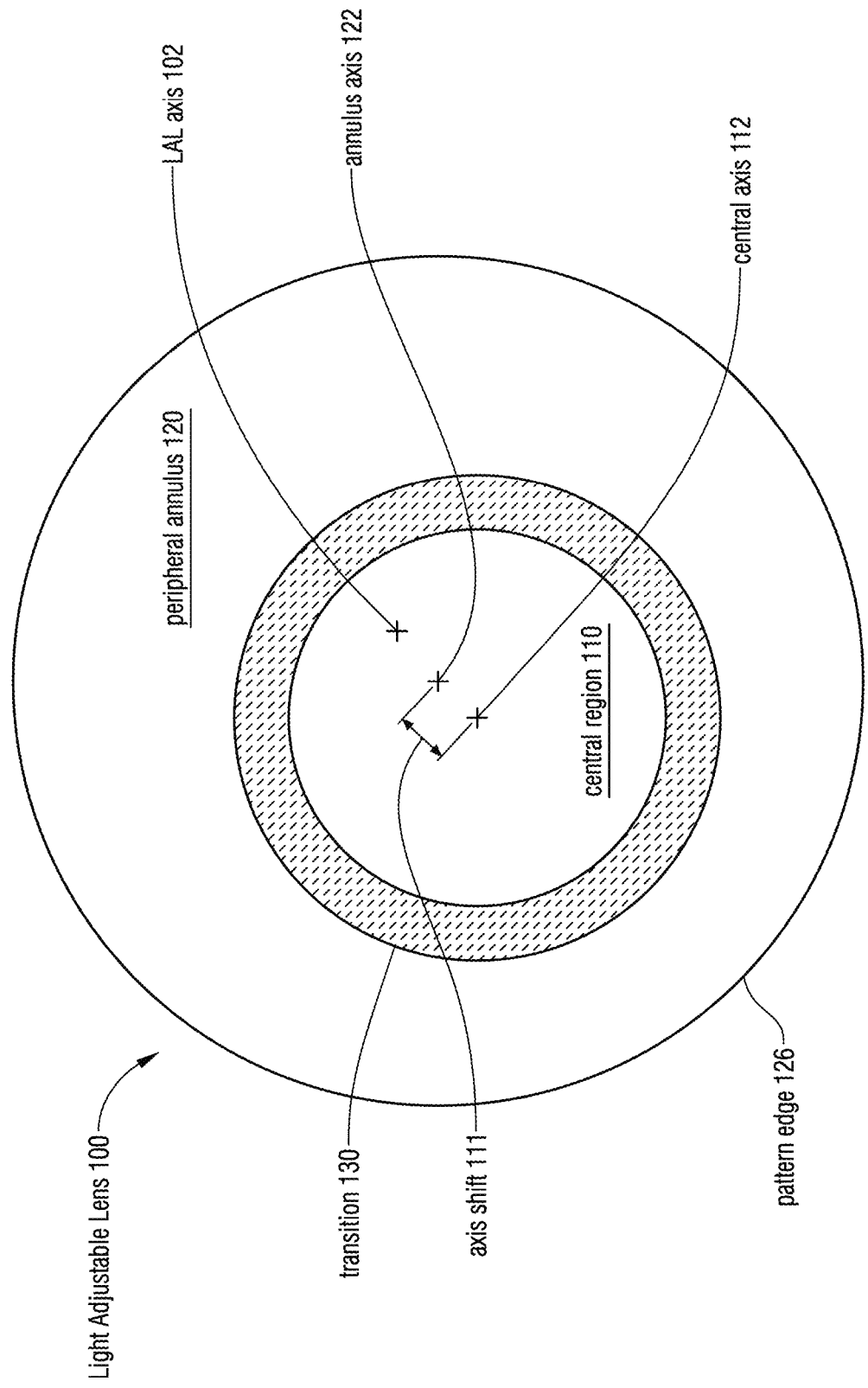

FIGS. 13A-B illustrate that, in order to address the above described needs, embodiments of a Light Adjustable Lens (LAL) 100 can comprise a central region 110, centered on a central axis 112, and a peripheral annulus 120, centered on an annulus axis 122 and surrounding the central region 110, wherein the central axis 112 is laterally shifted relative to the annulus axis 122 and the LAL axis 102.

Figure 13C:
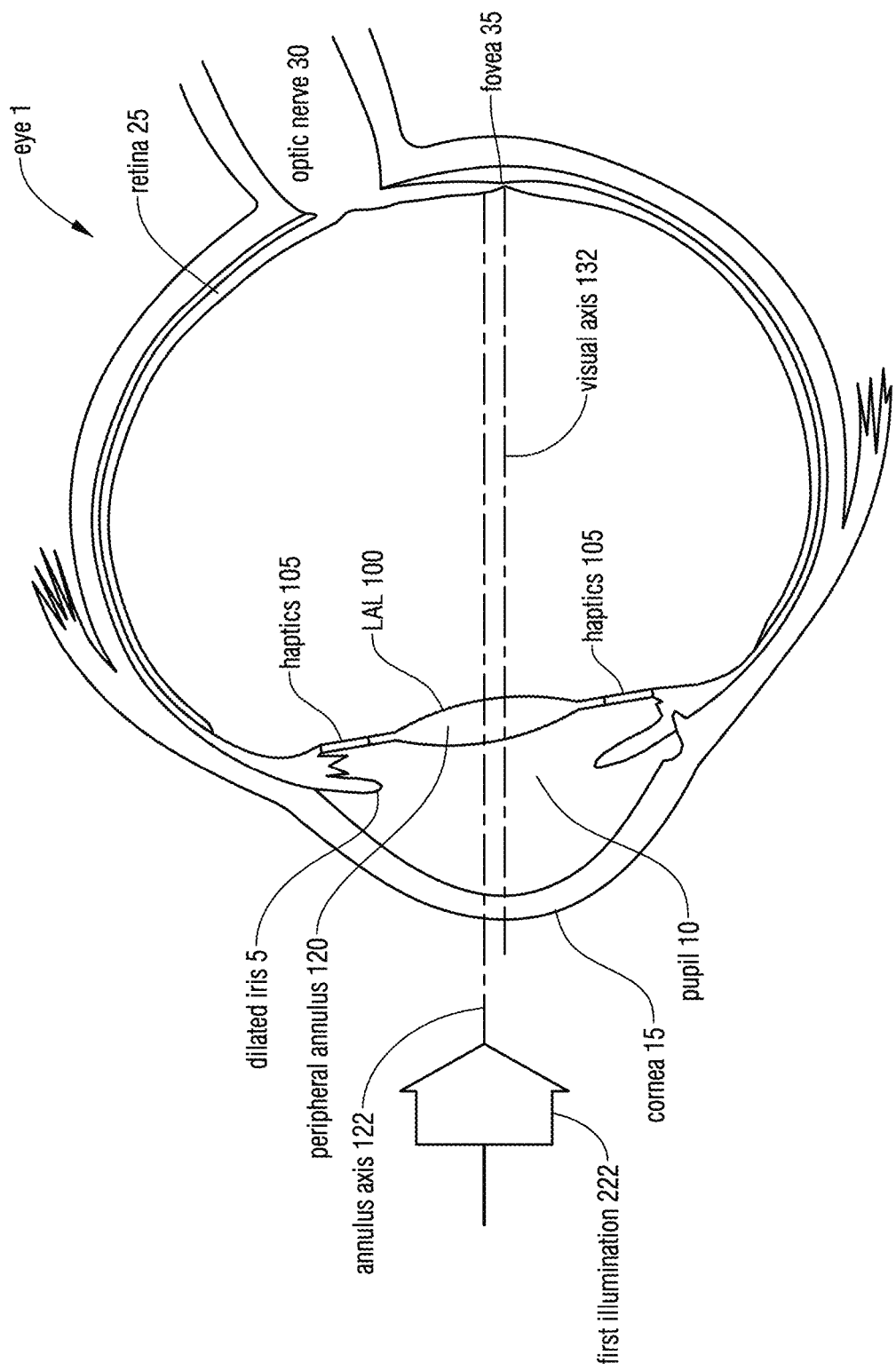
Figure 13D:
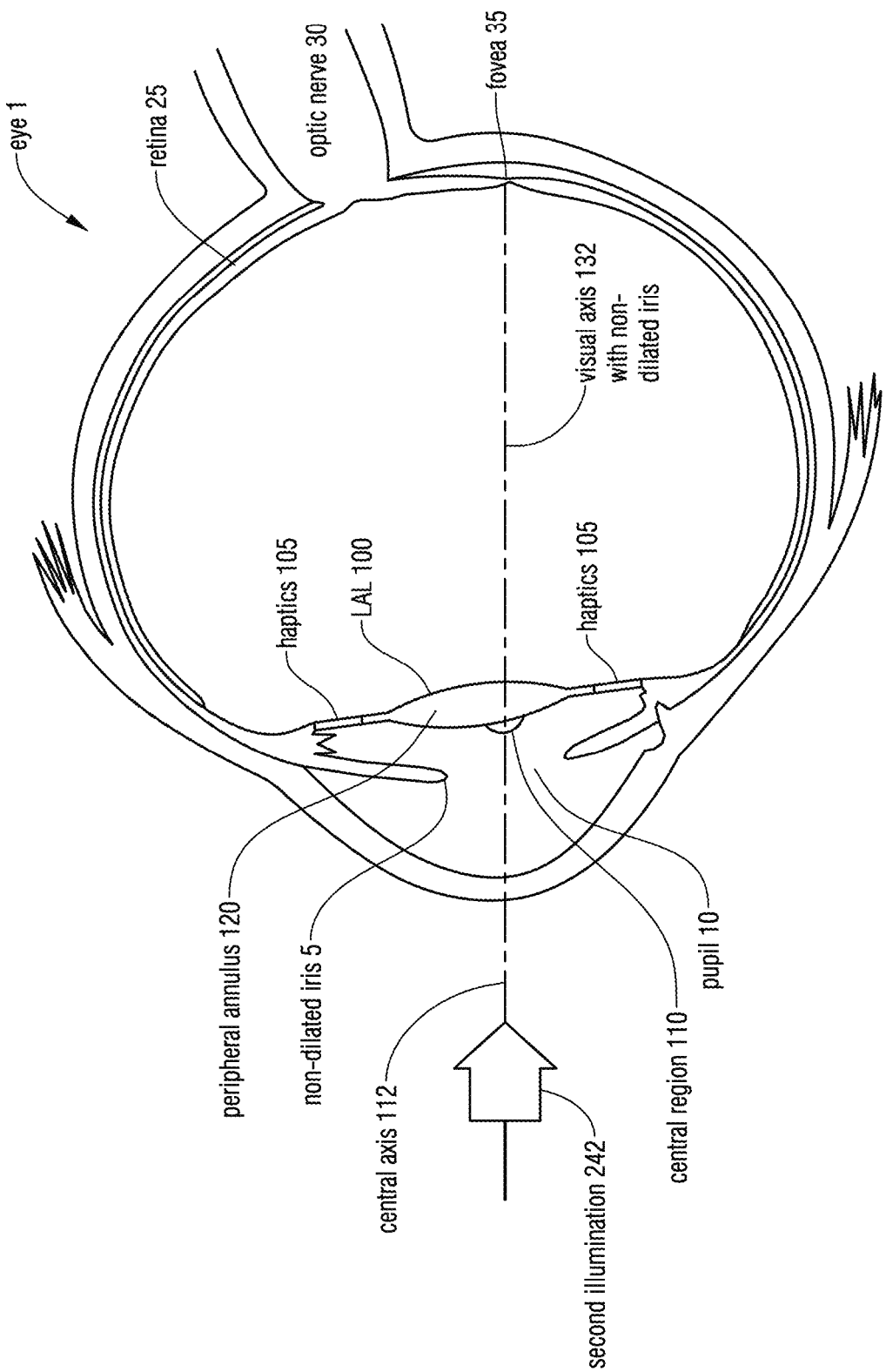

FIGS. 13C-D show steps of a light adjustment procedure that can be used to form the LAL 100 of FIGS. 13A-B. As shown in FIG. 13C, in typical embodiments the annulus axis 122 can be centered on the LAL axis 102, or on the center of the dilated iris 5. (The dilated/non-dilated status of the iris 5 is indicated in the Figures.) At this stage, a first illumination 222 can be applied to form the peripheral annulus 120, with a peripheral optical power 124, in the LAL 100, centered on the annulus axis 122. In some embodiments, the peripheral annulus 120 can be pre-molded into the LAL 100, instead of being formed after implantation. FIG. 13D shows that next, the central axis 112 can be centered on a visual axis 132 of the eye, e.g., after the iris 5 returned to its non-dilated state. Subsequently, a second illumination 242 can be applied to form the central region 110, with a central optical power 114, centered on this central axis 112, in order to optimize the optical performance of the LAL 100. In this procedure, the central axis 112 often ends up shifted relative to the annulus axis 122 and the LAL axis 102 for several reasons, including the following.

(1) First, during the surgical planning process, the doctor may have not selected the optimal, most centered position for the LAL 100.

(2) In other cases, the surgeon may have ended up implanting the LAL 100 in a position shifted from the presurgical planned position.

(3) In yet other cases, after the implantation, the LAL 100 may have shifted, or tilted away from its planned position, as shown in FIGS. 13C-D.

(4) Finally, the first illumination 222 is often applied with the iris 5 being dilated, to create the peripheral annulus 120 large enough to provide the desired optical performance even when the iris 5 is in its most dilated state. In contrast, the considerably smaller central region 110 is preferably formed with a non-dilated iris 5, in order to center it on the visual axis 132 with high precision. This is so because the optical performance of the small central region 110 deteriorates noticeably if it is not aligned with the visual axis 132 well. And finally, since the iris 5 often does not dilate in a uniform, concentric manner, the center of the relaxed, non-dilated iris 5 is often shifted relative to the center of the dilated iris 5, and therefore, the central axis 112 is often shifted relative to the annulus axis 122.

The shift of the central axis 112 relative to the annulus axis 122 will be sometimes abbreviated as axis shift 111. In embodiments of the LAL 100, the axis shift 111 can be captured in various ways. In absolute terms, the axis shift 111 can exceed 0.1 mm. In some embodiments, the axis shift 111 can exceed 0.2 mm. In yet other embodiments, the axis shift 111 can exceed 0.5 mm. In relative terms, the axis shift 111 can exceed 5% of the diameter of the central region 110. In some embodiments, the axis shift 111 can exceed 10% of the diameter of the central region 110. In yet others, it can exceed 20% of the diameter of the central region 110. Finally, in manufacturing terms, the axis shift 111 can exceed a manufacturing radius-tolerance of the LAL 100 by 20%. In other embodiments, the axis shift 111 can exceed the manufacturing radius-tolerance of the LAL 100 by 50%. This definition captures that the axis shift 111 is not an accidental, or tolerance-induced unintended shift of a pre-molded multifocal IOL, but an intended shift, exceeding the manufacturing tolerance.

FIG. 13A illustrates the optical power of the LAL 100 as a function of a radius r. The radius can be measured from a LAL axis 102. The central region 110 can have a position-dependent central optical power 114, the peripheral annulus 120 can have a position-dependent peripheral optical power 124. In embodiments, an average of the central optical power 114 can be at least 0.5 diopter different from an average of the peripheral optical power 124. In some embodiments, the average of the central optical power 114 can be at least 1.0 diopter different from the average of the peripheral optical power 124. Since the central axis 112 is shifted relative to the annulus axis 122, which itself may be shifted relative to the LAL axis 102, the central region 110 may be off a center of the LAL 100, as shown.

The embodiments of the LAL 100 blend various aspects of the EDOF and the CNA IOLs, since the LAL 100 has both a radially varying optical power, thus giving rise to an EDOF, as well as a central region 110, sometimes referred to as CNA region 110, and is thus shares some of the attributes of a multifocal lens. For this reason, embodiments of the LAL 100 will be interchangeably also referenced as a blended LAL 100.

FIG. 13B illustrates the same regions of the LAL 100, from a perspective along the LAL axis 102 of the LAL 100. In some embodiments, the LAL axis 102, the central axis 112, and the annulus axis 122 can all be different. In some typical embodiments, the LAL axis 102 and the annulus axis 122 can at least approximately coincide, and the central axis 112 can be shifted relative to both the LAL axis 102 and the annulus axis 122, as shown.

The position dependent optical power is typically induced by illuminating the LAL 100 by applying a suitable illumination pattern. The edge of the illumination pattern, a pattern edge 126 is also shown in FIGS. 13A-B, as a perimeter. Such blended LALs 100 can provide improvements for the above described medical problems at least as follows.

(1) After the LAL 100 is implanted and settles in the patient's eye, the central axis 112, and thus the central, or CNA region 110 can be centered with the visual axis 132 of the eye with the iris 5 being in a non-dilated state. It is recalled that the visual axis 132 of the eye with the iris 5 being in its non-dilated state often differs from either the geometrical LAL axis 102 of the LAL 100, and from the visual axis of the eye with the iris 5 in its dilated state. Therefore, a method that determines the eye visual axis 132 only after the LAL 100 has shifted and settled in the eye, and after the iris 5 returned to its approximately non-dilated state, and only then applies the second illumination 242 centered on the central axis 112 that is aligned with the eye visual axis 132, is an efficient method to center the CNA region 110 properly. In the resulting blended LAL 100, the central axis 112 often ends up laterally shifted relative to the annulus axis 122, as was described in relation to FIGS. 13A-B. Thus, the described embodiments of the blended LAL 100 are capable of overcoming the above-mentioned dc-centering challenge of pre-formed multifocal/CNA IOLs, and avoid the shift-induced aberrations, such as coma.

(2) Since the near vision capability of these blended LALs 100 is primarily delivered by the CNA/central region 110, the peripheral annulus 120 can be formed with a considerably smaller radial variation of the peripheral optical power 124, which thus extends the depth of focus only to a considerably smaller degree. Therefore, the blurriness and aberrations, caused by the peripheral annulus/EDOF region 120 of the blended LAL 100 is substantially less than in an EDOF-only IOL/LAL.

(3) The same reduction of the radial variation of the optical power in the blended LAL 100 causes the effective optical power, experienced by the patient, to vary less with the radius of the iris 5. This reduces another source of patient discomfort, and thus is a further medical benefit.

(4) In some blended LALs 100, the radial variation of the peripheral optical power 124 can be selected to induce a spherical aberration that compensates a spherical aberration caused by the cornea of the eye. This compensation can be partial, or an essentially complete compensation. The implantation of such spherical aberration-compensating blended LALs 100 can advantageously minimize the imaging aberrations of the entire ophthalmic system of the eye.

At least for the above reasons (1)-(4), and for further reasons articulated below, the here-described embodiments of the blended LAL 100 retain much of the medical benefits of the separate EDOF and the CNA designs, while they mitigate and minimize the undesirable side effects of these designs. These benefits also characteristically distinguish the blended LAL 100 embodiments from the mentioned preformed multifocal CNA IOLs, corneal inlays, and CNA contact lens.

Figure 14A:
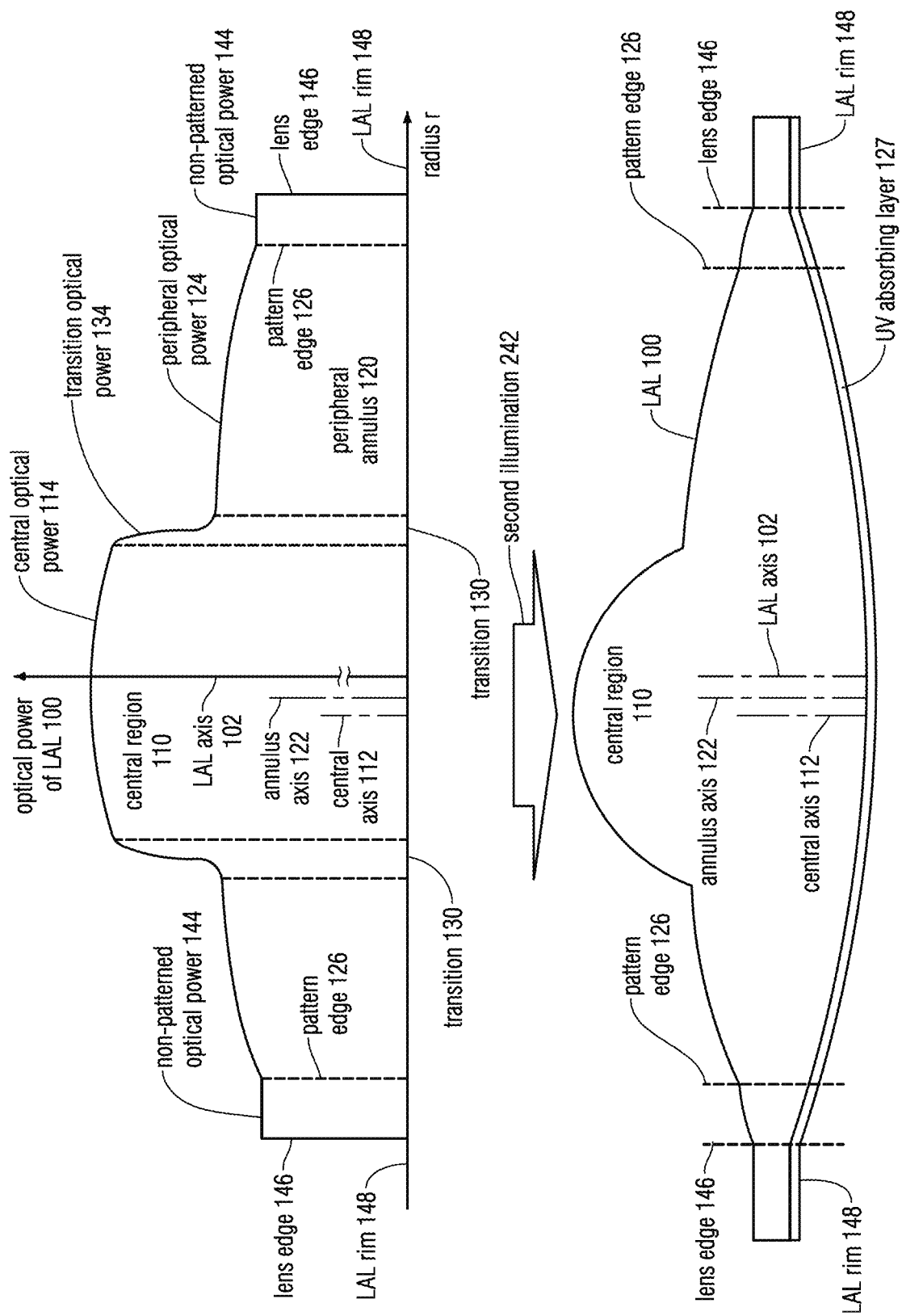
FIGS. 14A-B illustrate a Light Adjustable. Lens with position-dependent optical power and shifted axes.

With reference to FIG. 13C, the first illumination 222 can have any of the illumination patterns described in FIGS. 1-12, as applicable, used to increase the depth of focus of the implanted LAL. With reference to FIG. 13A and FIG. 14A, the lens materials and lens optical properties of the LAL 100 can have any material and property, described in relation to FIGS. 1-12, as appropriate.

In the embodiments illustrated in FIGS. 13-19, the average of the central optical power 114 is at least 0.5 diopter higher than the average of the peripheral optical power 124. In some embodiments, the central optical power 114 is at least 1.0 diopter higher than the average of the peripheral optical power 124. As such, the central region 110 is adapted to provide improved near vision, and the peripheral annulus 120 provides improved distance vision. In the embodiments of FIGS. 20A-C, the average of the central optical power 114 is at least 0.5 diopter lower than the average of the peripheral optical power 124. In some embodiments, the average of the central optical power 114 is at least 1.0 diopter lower than the average of the peripheral optical power 124. In these embodiments, the central region 110 is adapted to provide improved distance vision, and the peripheral annulus 120 provides improved near vision. Thus, the central region 110 can be called a Central Near Add (CNA) region 110 for the embodiments of FIGS. 13-19, while for the embodiments of FIGS. 20A-C, the central region 110 can be referred to as Central Distance Add (CDA), or Peripheral Near Add (PNA) region. These latter phrases are less widely used.

In all the embodiments of FIGS. 13-30, the term "average" can be defined in various suitable manners. For example, the average can refer to an area integral of the optical power. In some cases, only a portion, or fraction, of the total area of the central region 110 and the peripheral annulus 120 can be used to compute the average as an area integral. Such fractional definitions of the average can be useful to de-emphasize, or disregard non-representative deviations close to the pattern edge 126, or close to the region separating the central region 110 from the peripheral annulus 120. The fractional area can be at least 25% of the total area of either the central region 110, or the peripheral annulus 120. In other embodiments, this can fractional area can be 50%, 75%, or 90%. In other cases, the average can be defined along a representative circle, or over a band, or with a weighting function, or as a moment of a certain order of the optical power.

Figure 14B:
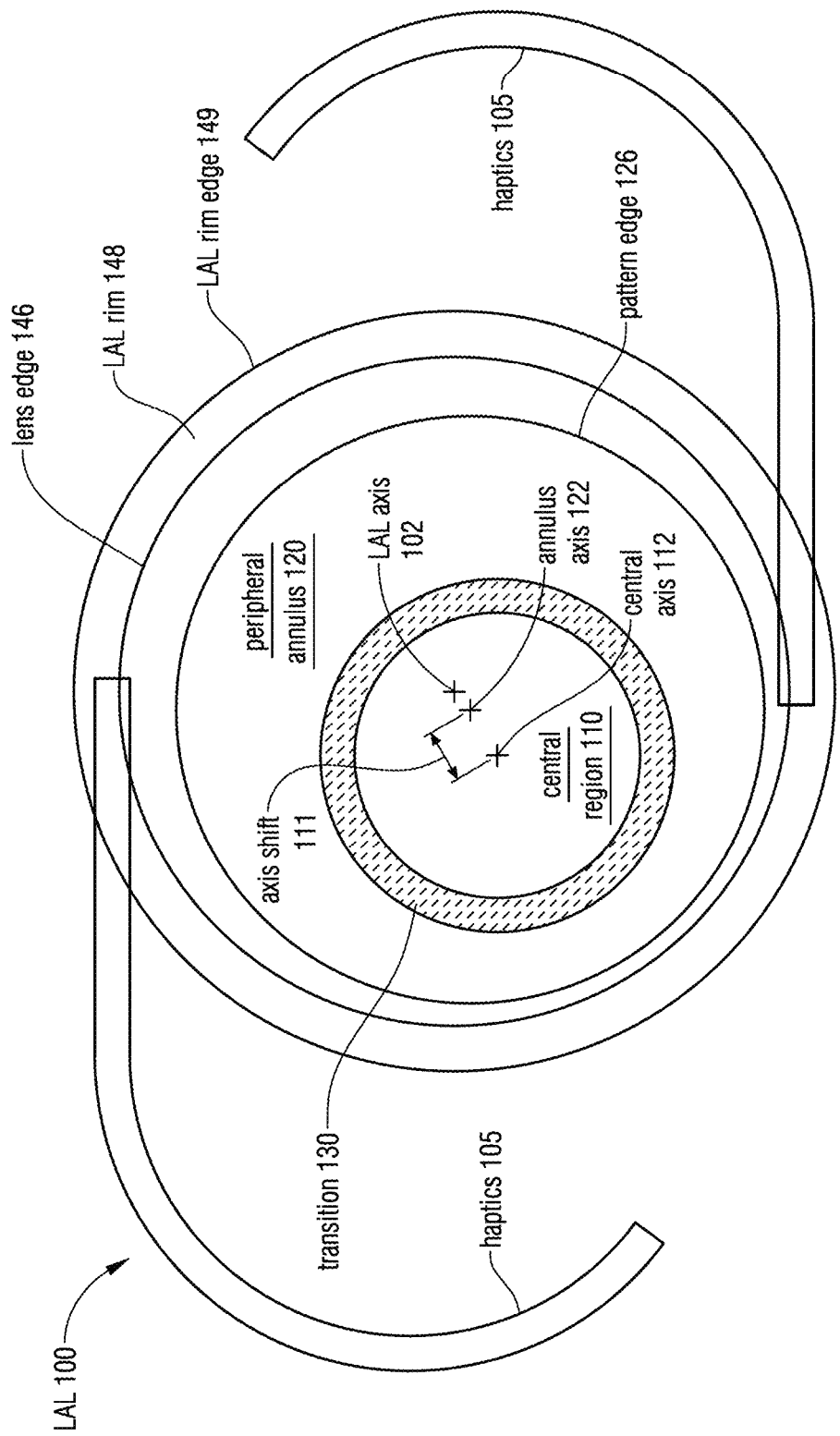

FIGS. 14A-B illustrate the position of these regions relative to the physical structure of the LAL 100. Prior to forming the peripheral annulus 120 and the central region 110 in the LAL 100 by illuminations 222/242, the front and rear surfaces of the LAL 100 typically have a single, approximately constant curvature, and, accordingly, have an optical power that is either independent of the position, or depends on it very weakly, only due to the finite thickness of the LAL 100, for example.

After the LAL 100 is formed by applying a first illumination 222 to form the peripheral annulus 120, and then by applying a second illumination 242, to form the central region 110, the central axis 112 is often shifted relative to the LAL axis 102, in order to compensate for the postsurgical shift and tilt of the LAL 100 that misaligned the LAL axis 102 with the visual axis 132 of the eye with the iris 5 in its non-dilated state. Sometime the annulus axis 122 also ends up being shifted relative to the LAL axis 102. In the shown example, the central optical power 114 and the peripheral optical power 124 meet at a sharp boundary. In other examples, a smoother transition optical power 134 of a transition 130 can be between them.

FIG. 14B shows the LAL 100 of FIG. 14A, from the perspective of the LAL axis 102, the relative positions of the central region 110 and the peripheral annulus 120, and the central axis 112 being shifted relative to the annulus axis 122 by the axis shift 111.

The physical structure of the LALs 100 includes a lens edge 146, continuing in a LAL rim 148 to a LAL rim edge 149. The haptics 105 protrude well beyond the LAL rim edge 149, to wedge and to stabilize the LAL 100 into the capsular bag emptied by the cataract surgery. The pattern edge 126 of the first illumination 222 typically does not reach all the way to the lens edge 146, it stops just before it. In some embodiments, the pattern edge 126 may coincide with the lens edge 146, or even extend to the LAL rim 148, that is initially flat and thus has no optical power. The LAL 100 typically also includes a UV (i.e. ultra-violet illumination) absorbing layer 127. The first and second illuminations 222/242 are applied from the side of the LAL 100 opposite of this UV absorbing layer 127. A role of this UV absorbing layer 127 is to reduce the transmitted portion of the illuminations to completely safe levels.

FIGS. 13A-B and FIGS. 14A-B further illustrate that the LAL 100 can also include a transition 130, between the central region 110 and the peripheral annulus 120. The transition 130 can have a transition optical power 134 that changes from the central optical power 114 to the peripheral optical power 124. The overall difference between the central optical power 114 and the peripheral optical power 124 will sometimes be referred to as an optical power change 136.

The double wavy lines indicate that the LAL 100 has an additional, "base" optical power in the 5-35 diopters range, typically within a few diopters of 20 diopters, whereas the position dependent peripheral optical power 124 may vary 0.5-2 diopters in the peripheral annulus 120; the transition optical power 134 may vary 0.5-2 diopters in the transition 130, and the central optical power 114 may vary 0.1-1 diopters in the central region 110, as an illustration. Broader ranges can be employed in some embodiments. To avoid making the curve of the position dependent optical powers 114, 124, and 134 uninformatively flat relative to the much larger base optical power of 10-30 D, this base optical power has been suppressed in the applicable Figures, and only indicated with the double wavy line. In other words, the optical power axis has been largely compressed in the relevant Figures, such as in FIG. 13A.

Figure 15A:
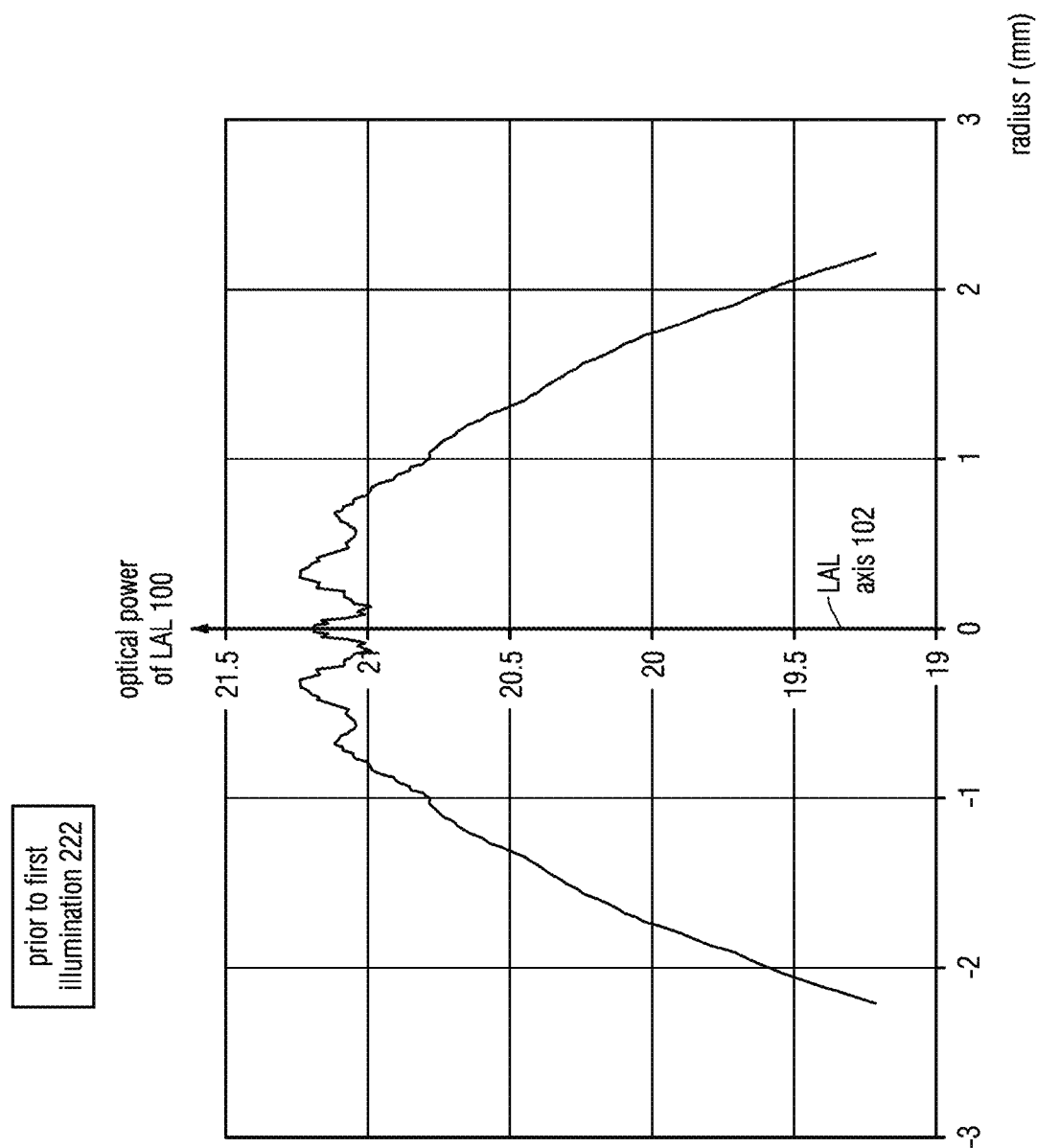
FIGS. 15A-C illustrate a position dependent optical power in a LAL.
Figure 15B:
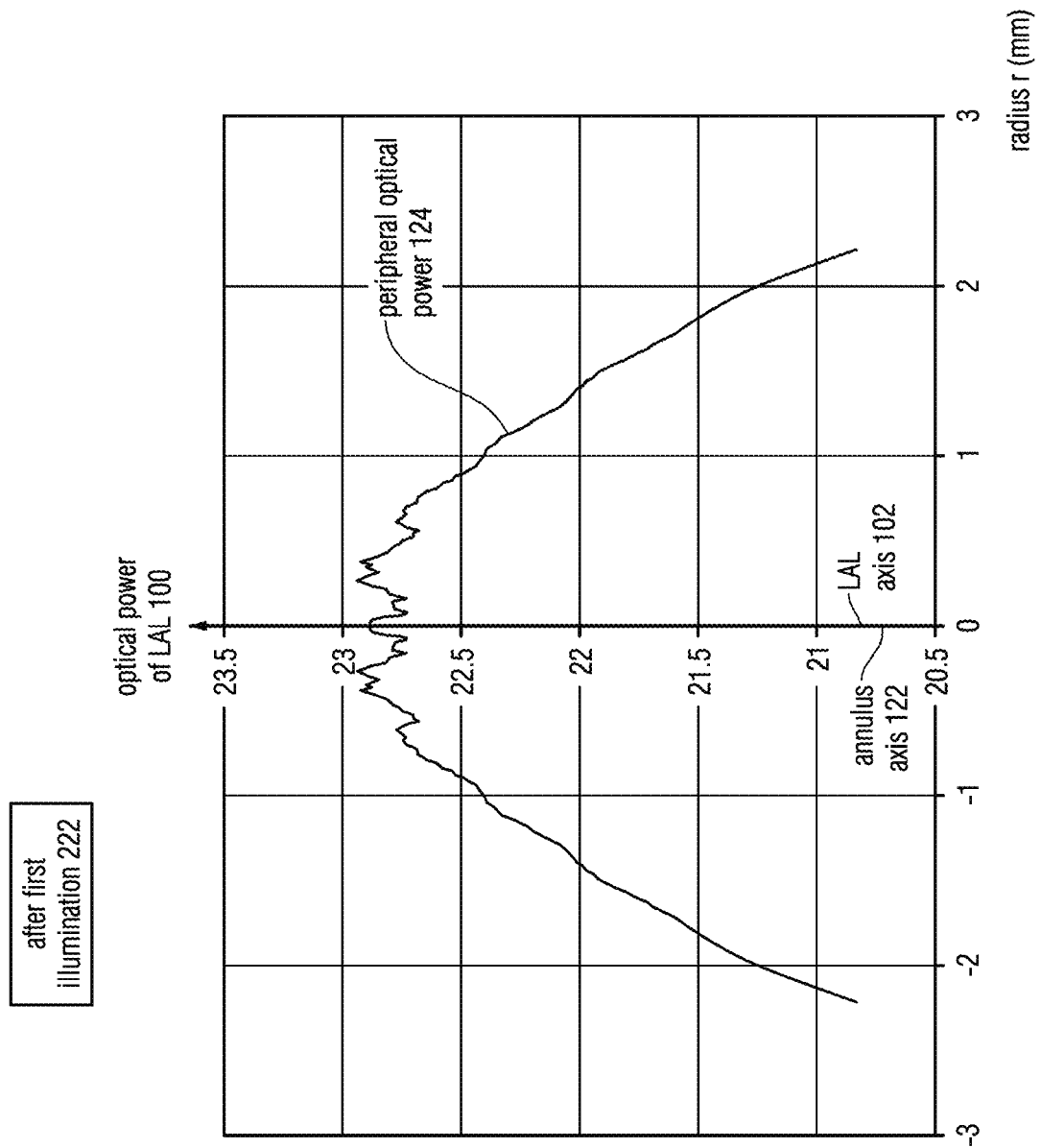
Figure 15C:
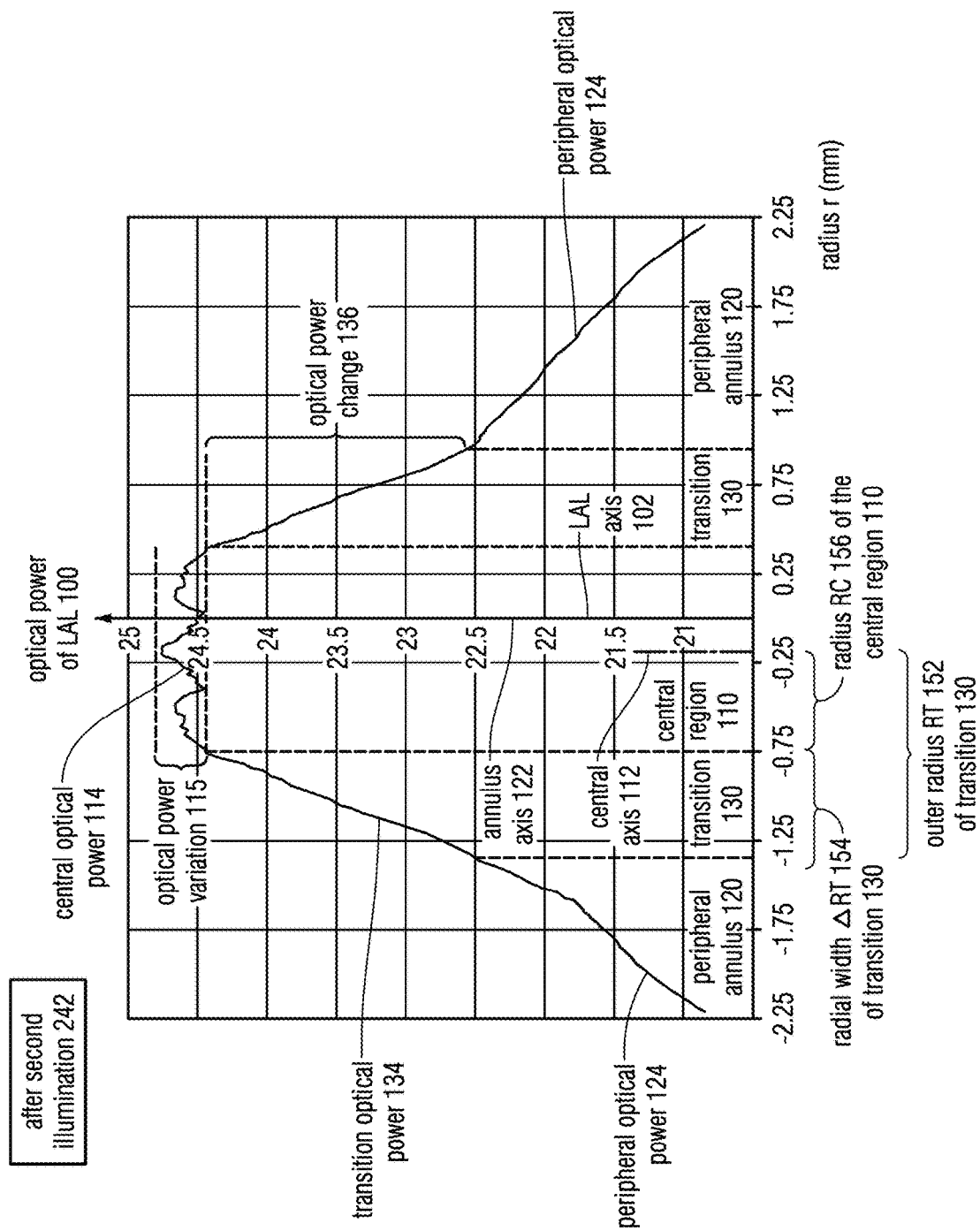

FIGS. 15A-C illustrate the results of measurements of the optical power as a function of the radial distance of the blended LAL 100 in the main stages of the formation process, as indicated in FIGS. 13C-D. Such optical power measurements can be performed by several known methods and apparatuses, such as wavefront measurement systems, and aberrometers, especially Shack-Hartmann wavefront sensors, among others.

FIG. 15A shows the radially varying optical power prior to the first illumination 222 in a LAL 100 that has a pre-molded radially varying optical power, causing a spherical aberration. The optical power OP varies from about OP=19.2 D at the lens edge 146 at around r=2.3 mm to OP=21.2 D at r=0, the LAL axis 102, yielding an about 2 D radial optical power variation: $\Delta OP = 2$ D.

FIG. 15B illustrates the result of the same optical power measurement after the first illumination 222 has been applied, centered on an annulus axis 122, which in this case was chosen to coincide with the LAL axis 102. At the lens edge 146 the OP got enhanced to 20.8 D, while at the center to 22.8 D. Thus, the first illumination 222 increased the average optical power of the LAL 100 by about 2 D, while preserved the radial optical power variation at ΔOP=2 D in this case.

FIG. 15C shows the radially varying optical power of the blended LAL 100 after the second illumination 242 has been also applied to induce a CNA in a central region 110. The second illumination 242 was centered on a central axis 112 that was shifted from the annulus axis 122, as shown. Visibly, the overall LAL optical power is a function of the radius in these blended LALs 100, and thus so is the overall focal distance. Accordingly, these blended LALs 100 can be characterized as "polyfocal IOLs", or "polyfocal LALs 100" as well.

Figure 16:
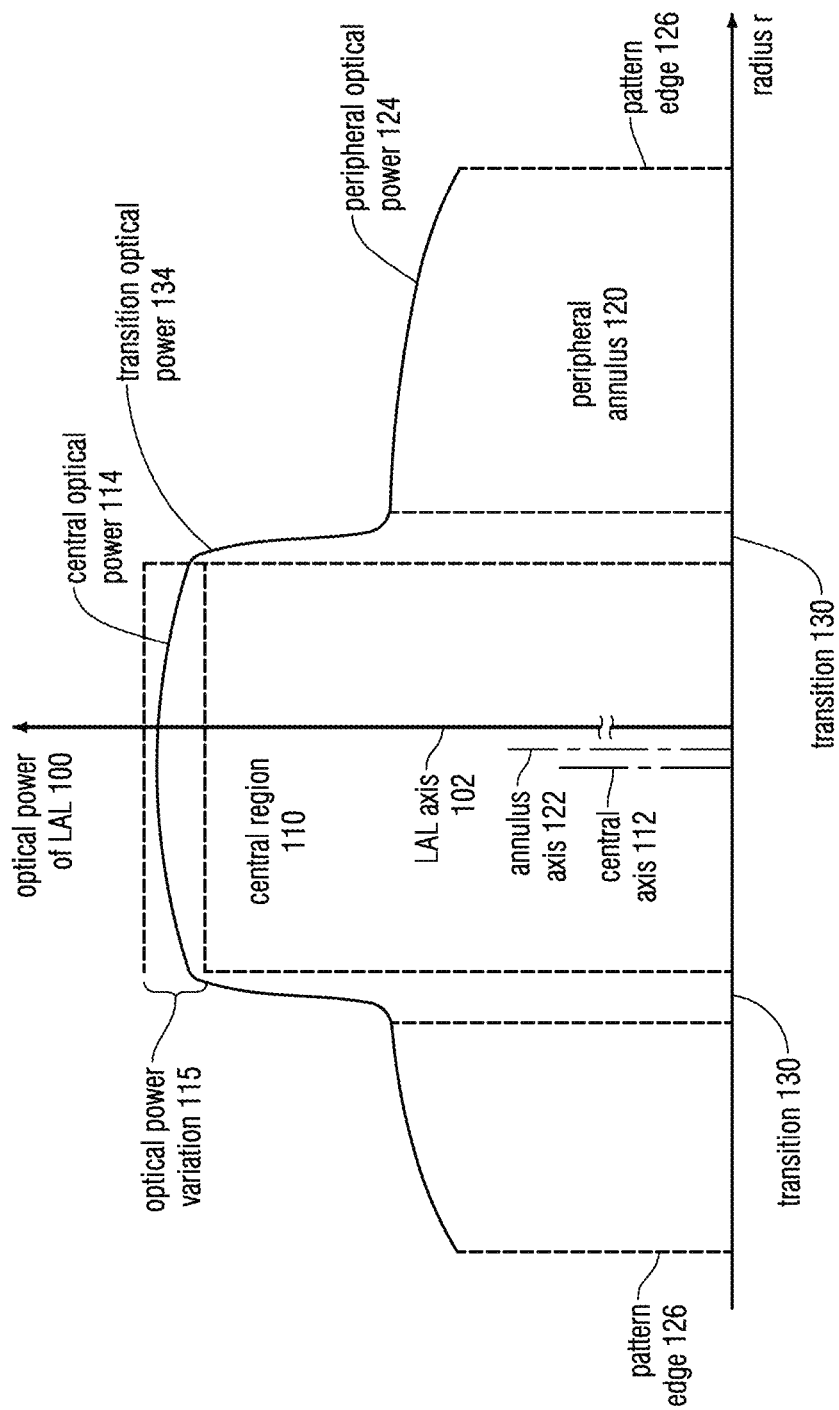
FIG. 16 illustrates a Light Adjustable Lens with position-dependent optical power.

In FIG. 15C, the central, or CNA, region 110 was formed over a diameter of 1.5 mm. Within this central region 110 the central optical power 114 is often intended to be quite smooth. FIGS. 15A-C illustrate a precision of the above numerical values and ranges, caused by natural measurement uncertainties and variations. The variations of the optical power measurements are high for small radii and decrease with increasing radius because the measurement of a region's optical power is set by the area of the region, and thus the variations are inversely proportional to this same area. The quadratically smaller area of the central region 110 compared to the peripheral annulus 120 explains that the fluctuations of the measured central optical power 114 are visibly greater than that of the peripheral optical power 124. FIG. 15C illustrates that in some embodiments, measurements of the central optical power 114 will exhibit an optical power variation 115, of 0.2 D. In other cases, the optical power variations 115 in the central optical power 114 can be up to 0.4 D. FIG. 16 illustrates that in some embodiments the central optical power 114 can have an optical power variation 115 of a few tenth of diopters that arises not from measurement-related fluctuations, but from the smooth curving central optical power 114.

In some embodiments of the LAL 100, the central region 110 can directly meet the peripheral annulus 120 at a well-defined boundary, making the transition 130 a sharp boundary, and the central region 110 and the peripheral annulus 120 can meet at this sharp boundary.

FIG. 13A, FIG. 15C and other Figures show that in some other embodiments, the transition 130 can be a smoother transition annular region between the central region 110 and the peripheral annulus 120. The smoothness of the transition 130 can be captured via ratios of relevant radii. FIG. 15C illustrates such relevant radii: a radial width of the transition 130, ΔRT 154, and an outer radius RT 152 of the transition 130. In some embodiments, the ratio ΔRT/RT can be less than 0.3. In other embodiments, ΔRT/RT can be less than 0.5, in yet others, less than 0.7. Here, a typical value for a radius RC 156 of the central region 110 can be in the range of 0.5 mm to 1.0 mm in some embodiments.

It is noted that statements and numerical ranges of the optical properties, such as the optical power and the spherical aberration, are meant within a context and a measurement protocol, since these optical properties of the LAL 100 can be measured in different ways, following different protocols that result in different values.

(1) In one protocol, the LAL 100 can be characterized in isolation, on an optical bench, where the LAL 100 is typically immersed into a saline solution to mimic its optical performance in the aqueous of the eye. Such measurements can be set up at least in the following ways. (1a) Starting with a LAL 100 that has not been light adjusted yet; then performing a light adjustment illumination protocol as defined by the LAL manufacturer, and then measuring the optical characteristics of the light-adjusted LAL 100 on the optical bench. (1b) Implanting the LAL 100 into a patient's eye; then performing the light adjustment illumination protocol in the eye; then explanting the light-adjusted LAL 100 from the patient's eye; and finally, measuring the optical characteristics of the explanted LAL 100 again on the optical bench.

(2) In another protocol, the LAL 100 can be characterized "In situ", as part of the overall ophthalmic optical system that includes the LAL 100 and the cornea that has its own optical power and own spherical aberration, the two lenses separated by a space filled by the aqueous of the anterior chamber of the eye. Defining such an "in situ" protocol can be particularly useful if the optical power of an implanted LAL needs to be determined without explanting the LAL from the patient's eye. Here we also describe two related optical measurement approaches.

(2a) In the in situ protocol, the optical power of the cornea 15, $P_c$, and the optical power of the LAL, $P_{LAL}$, combine into the overall ophthalmic power $P_o$, according to the known formulae of two lens (telescopic) systems:

$$P_o = P_c + P_{LAL} - d \cdot P_c \cdot P_{LAL} = P_c + (1 - d \cdot P_c) \cdot P_{LAL} \quad (3)$$

where d is the separation between the cornea 15 and the LAL 100. Using typical values of $P_c$ about 40-45 D and d about 7 mm, a 1 D change in the optical power $P_{LAL}$ in the LAL plane approximately translates to an about 0.7 D change in the overall optical power $P_o$ in the corneal plane, defined approximately as a plane at the vertex of the cornea 15.

Eq. (3) establishes a translation scheme between the different types of optical power measurements. For example, if the LAL optical power $P_{LAL}$ is adjusted by 1 D on the optical bench, the adjusted LAL can be expected to cause an about 0.7 D change of the ophthalmic optical power $P_o$, when implanted in the eye. And in reverse, if a light adjustment procedure is carried out on an implanted LAL that is measured to cause a 1 D change of the ophthalmic optical power $P_o$ in the corneal plane, and then the LAL is explanted, the explanted LAL optical power $P_{LAL}$ can be expected to show a power change of about 1 D/0.7=1.43 D in the LAL plane.

(2b) Eq. (4) below shows that the optical power of the entire eye ophthalmic optical system can be also calculated with an analysis that includes more parameters and details, such as additionally capturing beam propagation from the cornea to the separately located spectacle plane. Eq. (4) below shows the change in power of the implanted LAL, $\Delta P_{LAL}$, necessary to achieve a specific refractive correction of the eye at the spectacle plane, $R_x$, determined as the refractive correction needed after the LAL 100 has been implanted into the eye. With the notation of protocol (2a), $R_x = \Delta P_o$:

$$\Delta P_{LAL} = n_{Aq} \left( \frac{1}{\frac{n_{Aq}}{\frac{1}{\frac{1}{R_x} d_v} + P_c} - d_{ELP}} - \frac{P_c}{n_{Aq} P_c d_{ELP}} \right) \quad (4)$$

Here, $n_{Aq}$ is the refractive index of the human aqueous, $P_c$ is the corneal optical power, $d_{ELP}$ is the distance from the apex of the cornea to the back principal plane of the implanted LAL 100, and $d_v$ is the vertex distance, i.e. distance from the cornea to the spectacle plane. Typical values in Eq. (4) include a corneal power P=45 D, $d_{ELP}$=4.5×10$^{-3}$ m, and $n_{Aq}$=1.336. With these parameters, a desired refractive correction $R_x$=+0.5 D translates to a change in LAL power of $\Delta P_{LAL}$+2.14 D. Taking the ratio of the desired spectacle plane refractive correction Rdx+1.5 D, to the required change in LAL power, $\Delta P_{LAL}$=+2.14 D, results in a translation ratio of 0.70. This ratio essentially agrees with the 0.7 translation ratio determined from Eq. (3). Patient-to-patient variations of the above parameters can lead to a plus-minus 3% variation of this translation factor of 0.7. In other embodiments, to a plus-minus 5% variation, or plus minus 10% variation.

Translation factors can be derived for the other optical characteristics as well. For example, the spherical aberration, SA, depends notably on the measurement diameter, aperture, or pupil. (1) For isolated LALs, a natural definition of this pupil is in the plane of the LAL. (2) However, for implanted LALs, the SA cannot be directly measured at the LAL plane, and therefore a natural definition of the pupil is in the corneal plane. From this, the LAL-plane SA can be derived. A conversion, or translation factor can be established between these two measurement positions based on recalling the followings.

(2.1) The SA scales with the fourth power of the diameter, and (2.2) a beam that is collimated at the cornea is focused down by the corneal optical power $P_c$ to a decreasing diameter as it propagates toward the implanted LAL. Using a representative corneal power of $P_c$=45 D, a diameter of a collimated beam incident on the corneal plane gets reduced by about a factor of 0.85 by the time it reaches the LAL plane. Equivalently, a diameter of a beam propagating from the LAL out to the cornea increases by a factor of 1/0.85. Thus, e.g., a corneal beam diameter of 6 mm gets focused down to a 5.1 mm LAL-plane beam diameter, and a corneal beam diameter of 4.7 mm gets focused down to a 4.0 mm LAL-plane beam diameter. It is customary to characterize the SA values of contact lenses, positioned on the cornea, at a d=6 mm diameter. It is also customary to characterize IOL SA values at a diameter of 4 mm, which is, however, less than the diameter of a down-focused 6 mm beam. Therefore, translating the d=6 mm corneal SA values into d=4 mm IOL SA values involves two conversion steps: the down-focus factor of 0.85, and the ratio of diameters to the fourth power. Thus, a LAL/IOL plane SA value, measured at 4 mm diameter is to be converted to the diameter of 5.1 mm that corresponds to the 6 mm corneal diameter by the down-focusing factor of 0.85. As a relevant example, since (5.1 mm/4 mm)$^4$=2.6, a SA value of SA=0.1 μm at a 4 mm LAL-plane diameter corresponds to a SA=0.26 μm at a 6 mm corneal-plane diameter. For patient corneas with different corneal optical power, this correspondence factor can fall within a range around 2.6, such as in the range of 22-3.0, in other cases, 2.4-2.8.

(3) The above SA values characterize the light adjusted region. With reference to FIGS. 13A-B, 14A-B, this light adjusted region extends to the pattern edge 126, typically inside the LAL rim edge 149. Since the shape of the LAL 100 continues to change outside the pattern edge 126, SA values that are measured with diameters past the pattern edge 126 are impacted by the LAL rim 148, and tend to be different from SA values measured at diameters inside the pattern edge 126. In some cases, the SA can even change sign when measured with the rim included.

In some blended LAL 100s, it can be medically beneficial for the central optical power 114 to have only a limited spatial variation, and a corresponding approximately flat position-dependence, since limiting spatial variations limits the aberration of the imaging, and thus improves the visual acuity. In these "flat top" embodiments, the central region 110 can have an optical power variation less than 0.2 diopters over 50% of the central region 110, resulting in high visual acuity. In other embodiments of blended LALs 100, the central optical power 114 can be a function of a radius from the central axis 112, having an optical power variation 115 greater than 0.2 diopters over 50% of the central region 110. These embodiments may be emphasizing the presbyopia mitigation benefit.

Analogously, in some embodiments of the LAL 100, the peripheral optical power 124 can have an approximately flat position-dependence, having an optical power variation less than 0.2 diopters over 50% of the peripheral annulus. In related embodiments, the peripheral optical power 124 can be a function of a radius from the annulus axis 122, having an optical power variation greater than 0.2 diopters over 50% of the peripheral annulus.

Figure 17A:
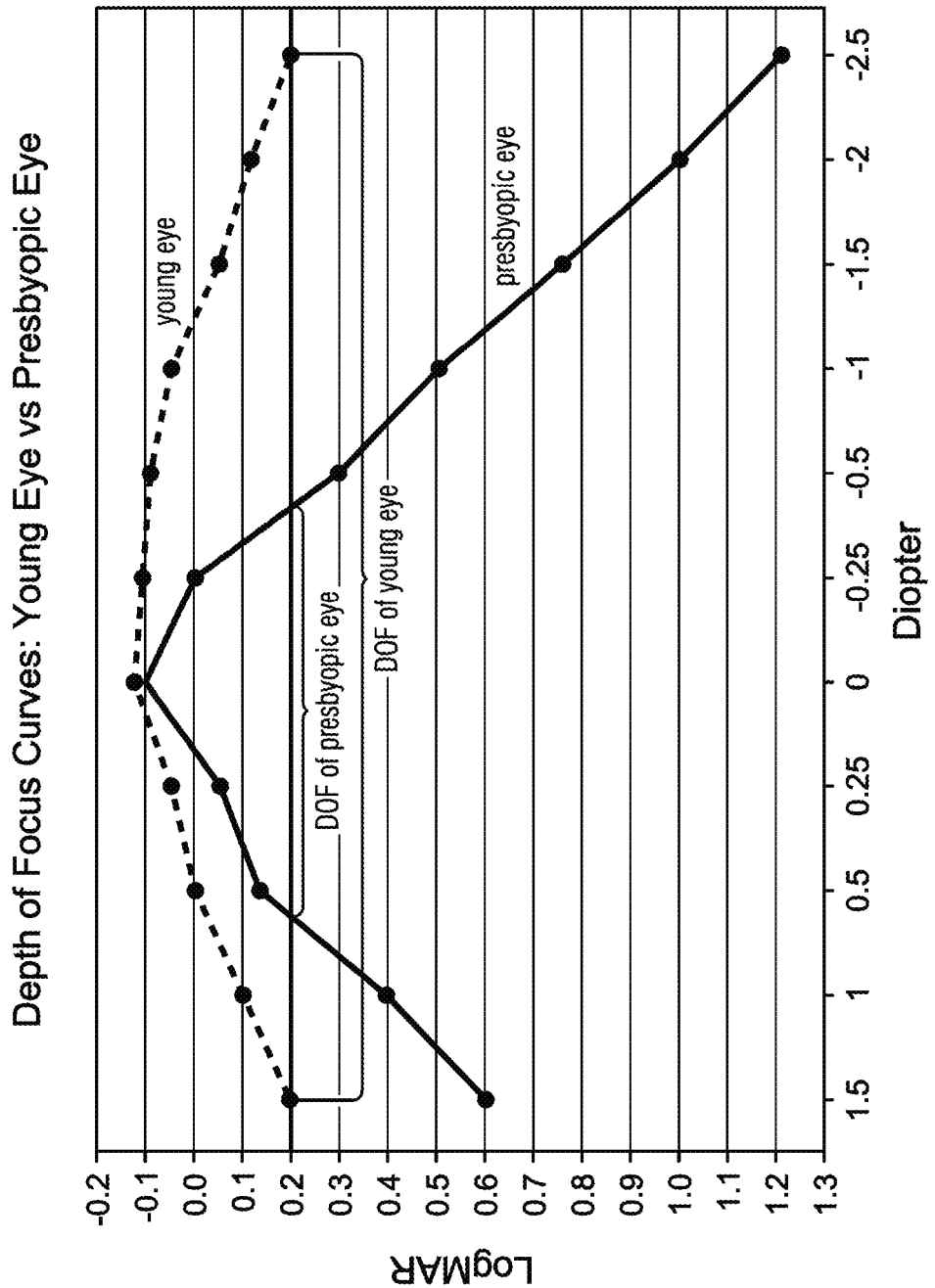
FIGS. 17A-B illustrate the visual acuity of presbyopic eyes, with implanted EDOF or CNA LALs.
Figure 17B:
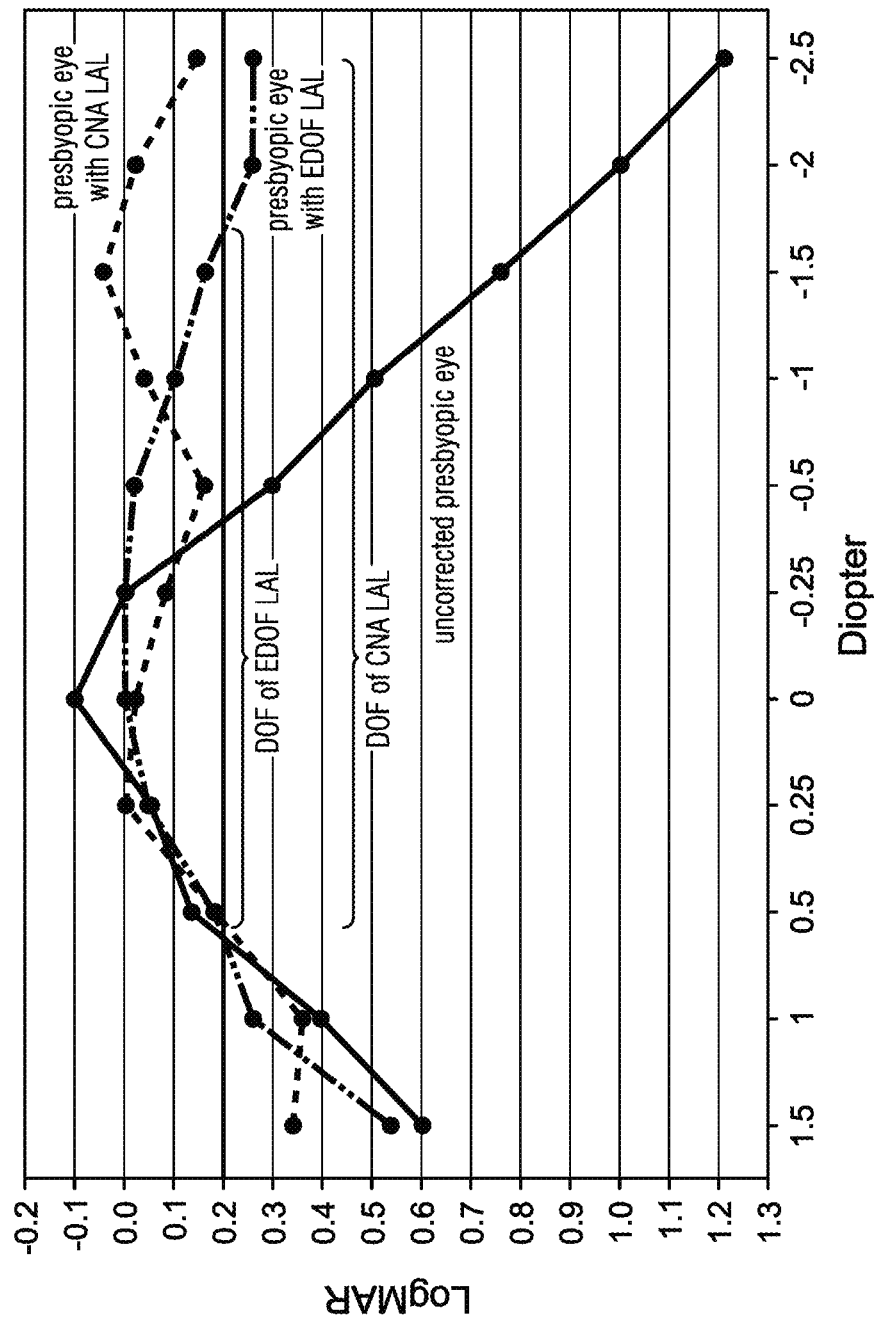
Figure 18:
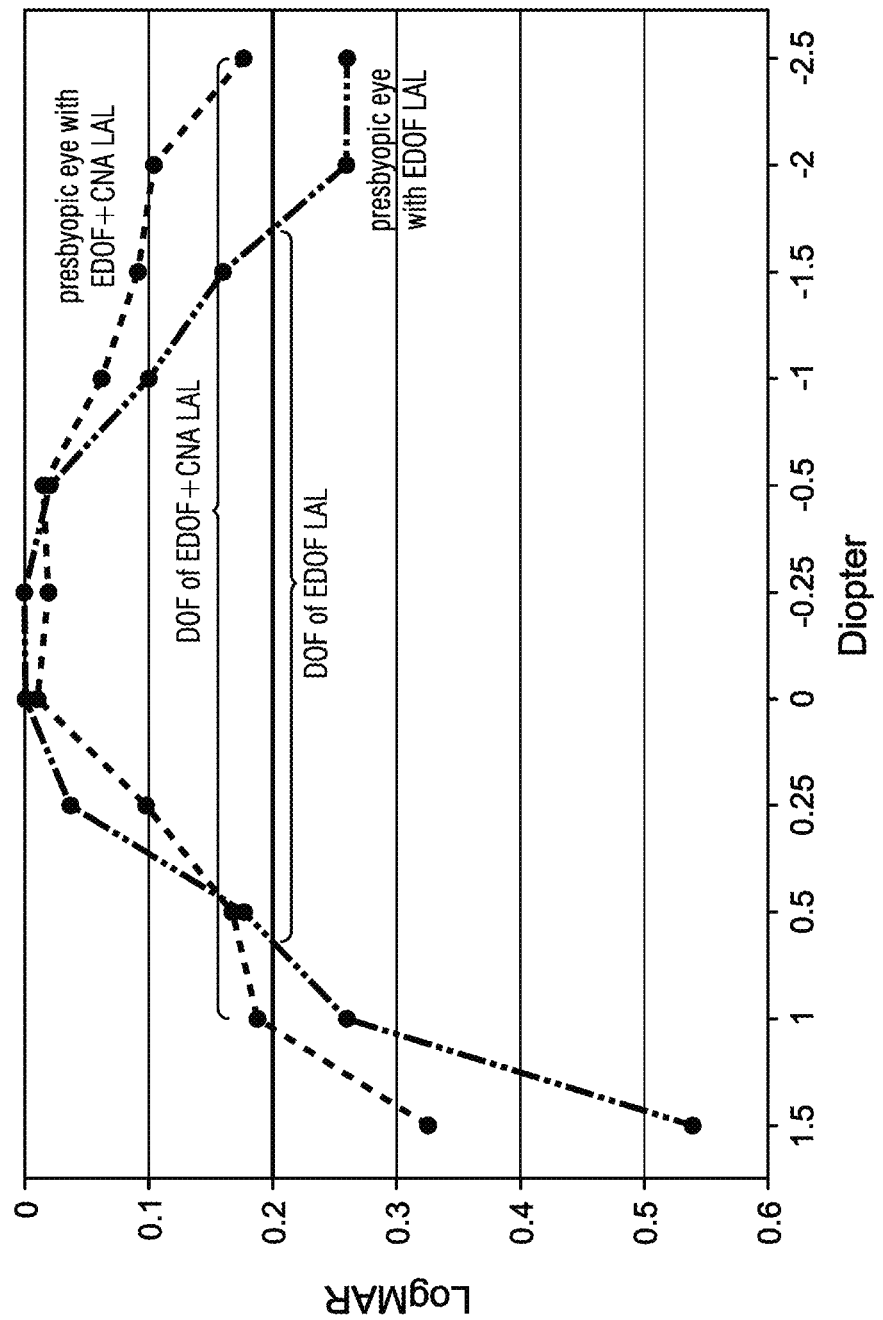
FIG. 18 illustrates the visual acuity of presbyopic eyes, with implanted EDOF+CNA LALs.

FIGS. 17A-B and 18 illustrate how the LAL 100 with the above characteristics mitigates the presbyopic medical needs, described earlier. One of the most widely used measure of a patient's vision is the Visual Acuity (VA), which records the ratio of a distance a patient has to stand from an eye chart to achieve the same visual clarity as a person with normal eyes achieves from 20 feet. There are closely related conventions to determine this VA value, such as the Snellen VA and the Early Treatment Diabetic Retinopathy Study (ETDRS) VA. Another measure is the log MAR, where "MAR" abbreviates "Minimal Angle Resolved", and "log" references that the logarithm of this angle is taken for this measure. These measures are determined based on the subjective feedback of the patient, typically by asking the patient to report which letters in which lines he/she can see clearly on the eye chart, from different distances. In practice, changing the viewing distance is often simulated by inserting lenses of varying diopters in front of the patient, using a phoropter. Typically, these tests are reported after incorporating a correction to infinite viewing distances. Thus, in FIGS. 17A-B and FIG. 18, 1D corresponds to a viewing distance of 1 m, etc. These two measures can be translated to each other, as shown in Table 8:

TABLE 8

| VA | logMAR |
| --- | --- |
| 20/40 | 0.3 |
| 20/32 | 0.2 |
| 20/25 | 0.1 |
| 20/20 | 0.0 |
| 20/16 | −0.1 |
| 20/12.5 | −0.2 |
| 20/10 | −0.3 |

It is customary to accept log MAR values smaller than 0.2 (i.e. VA values better than 20/32), as indications of good, or satisfactory visual acuity. (Following convention, the negative log MAR values are at the top of the axis, and they grow to positive lorMAR values at the bottom of the axis. Therefore, log MAR values "smaller than 0.2" are in fact above the log MAR=0.2 line in FIGS. 17-18.) With this preparation, FIGS. 17A-B and 18 demonstrate the problem of presbyopia and the improved visual acuity delivered by the blended LALs 100. A young eye has an easily deformable crystalline lens, and therefore can accommodate to a wide range of viewing distances. This is seen in FIG. 17A by the base of the log MAR curve, i.e. the range of diopters with log MAR values smaller than 0.2, covering the wide range from +1.5 D to −2.5 D. In viewing distances, this translates to good visual acuity from (1/2.5 D)=40 cm out to infinity, and beyond, to virtual targets. In terms of a depth of focus, or DOF, this young eye exhibits a DOF(young)=+1.5 D−(−2.5 D)=−4D.

An older, presbyopic eye is gradually losing its ability to accommodate to different viewing distances. Presbyopia is, in fact, Greek for "old eyes", or "old sight". E.g., the DOF of the shown presbyopic eye decreased to DOF(presbyopic)=+0.5 D−(−0.5 D)=1D, approximately.

FIG. 17B illustrates the two presbyopia solutions, discussed earlier. (1) IOLs with an Extended Depth of Focus, or EDOF IOLs are formed with a radially varying optical power that extends the focal point into an elongated focal region. The adaptiveness of the human vision enables the patient's brain to extract images created with this elongated focal region, to see targets in a wider range. This adaptiveness smoothly broadens the log MAR curve, extending the DOF to DOF(EDOF)=+0.5 D−(−1.5 D)=2 D.

(2) IOLs with a Central Near Add (CNA) introduce a more distinctly defined second focal region, and thus broaden the log MAR curve unevenly by introducing a second maximum. The illustrated CNA IOL has a DOF (CNA)=+0.5 D−(−2.5 D)=3D, approximately. While both of these presbyopic techniques extend the DOF and thus mitigate presbyopia by improving visual acuity over an extend range of target distances, they do so by introducing drawbacks, as was discussed earlier. The log MAR curve articulates these drawbacks further. EDOF IOLs extend the DOF to a medium degree. CNA IOLs extend the DOF better than EDOF IOLs, DOF(CNA)>DOF(EDOF). However, they do so at the expense of a noticeable reduction of the midrange visual acuity, as shown by the pronounced log MAR minimum around −0.5 D.

FIG. 18 illustrates the log MAR curve of the blended LALs 100, which blend the EDOF and the CNA techniques. (1) Visibly, the blended LALs 100 extend the medium DOF of the EDOF IOLs from DOF(EDOF)=2 D to the longer DOF of the CNA IOLs: DOF(EDOF+CNA)=3-3.5 D. (2) Importantly, the blended EDOF+CNA LALs 100 also largely eliminate the midrange log MAR minimum of the CNA IOLs. To sum, the blended EDOF+CNA LALs 100 deliver the longer DOFs of the CNA IOLs, as well as the no-midrange-minimum smoothness of the EDOF IOLs. In other words, blended LALs 100 deliver the positives of the two existing presbyopia IOLs, while eliminating their drawbacks.

FIGS. 13-18 illustrated blended LALs 100, where (1) the central optical power 114 was higher than the peripheral optical power 124, at least in an average sense. Also, the optical power was a decreasing function of the radius (2) in the central region 110, and (3) in the peripheral annulus 120, shown by the downward curvatures of the optical power curves in both of these regions. These three design factors (1)-(3) can be combined in $2^3$=8 different ways, defining 8 possible embodiments of the blended LALs 100. All 8 combinations can offer advantages for visual challenges.

Figure 19:
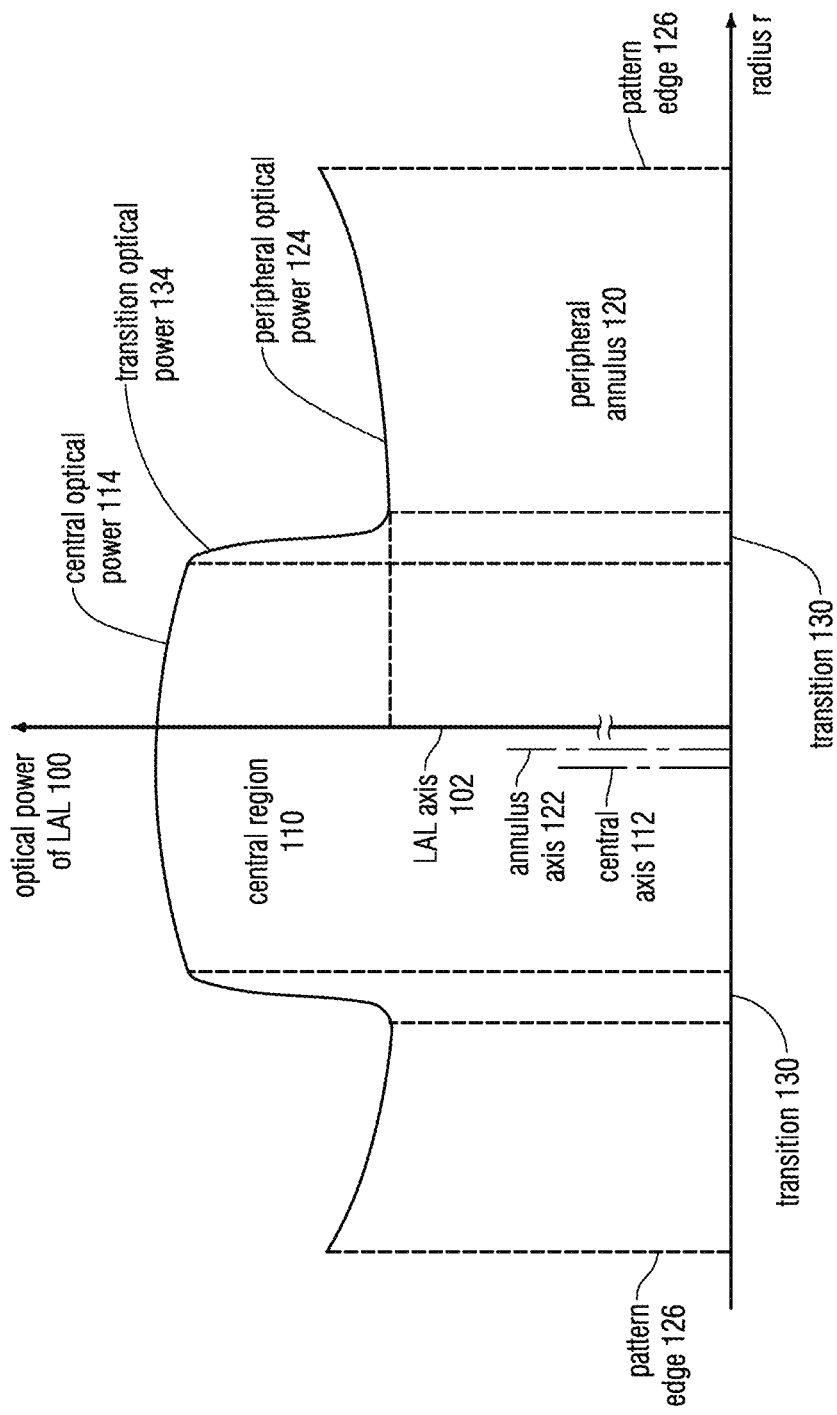
FIG. 19 illustrates a Light Adjustable Lens with a peripheral optical power of differently-curved radial dependence compared to FIG. 1.
Figure 20A:
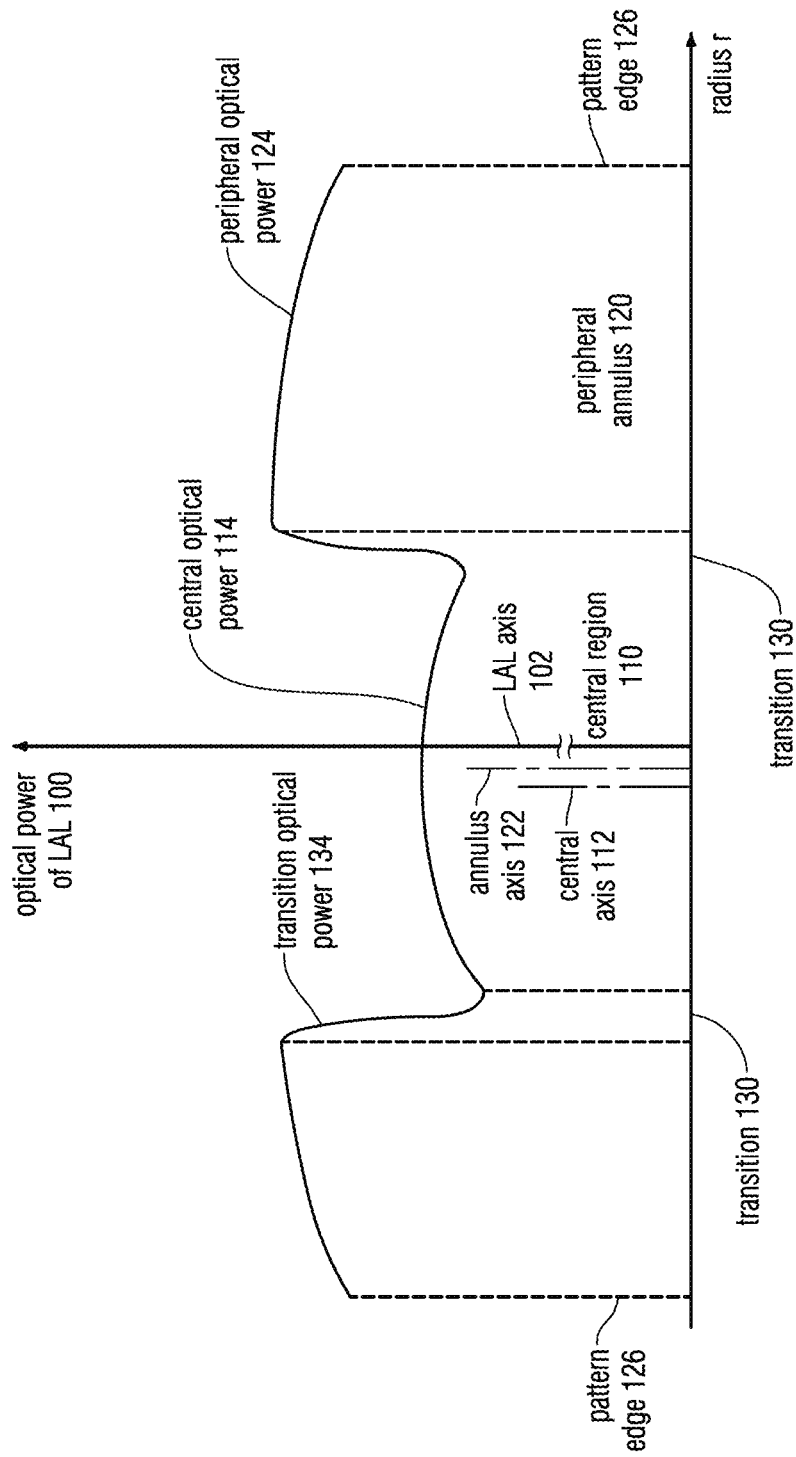
FIGS. 20A-C illustrate Light Adjustable Lenses with an average central optical power less than an average peripheral optical power, with various radial dependence curvatures.
Figure 20B:
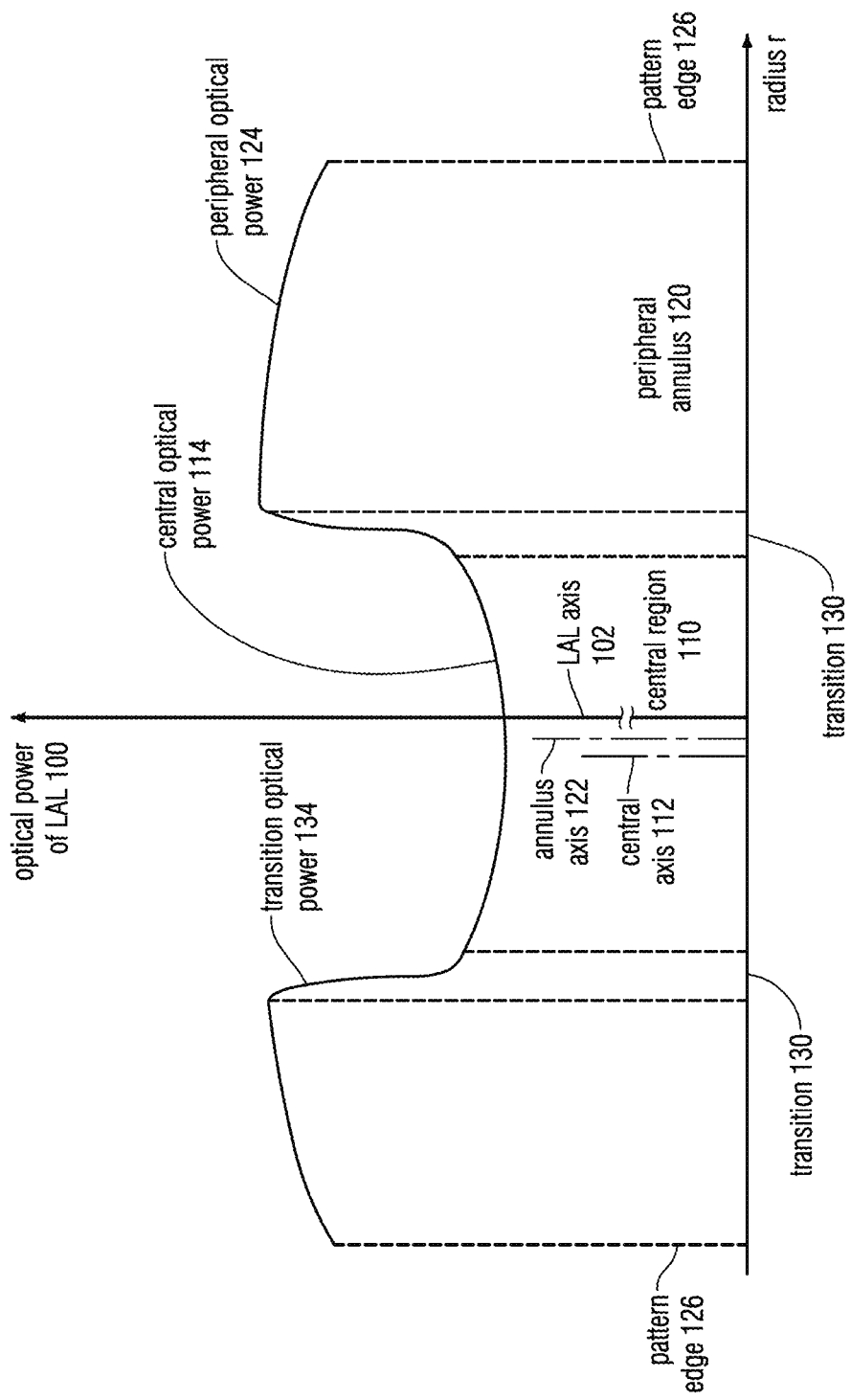
Figure 20C:
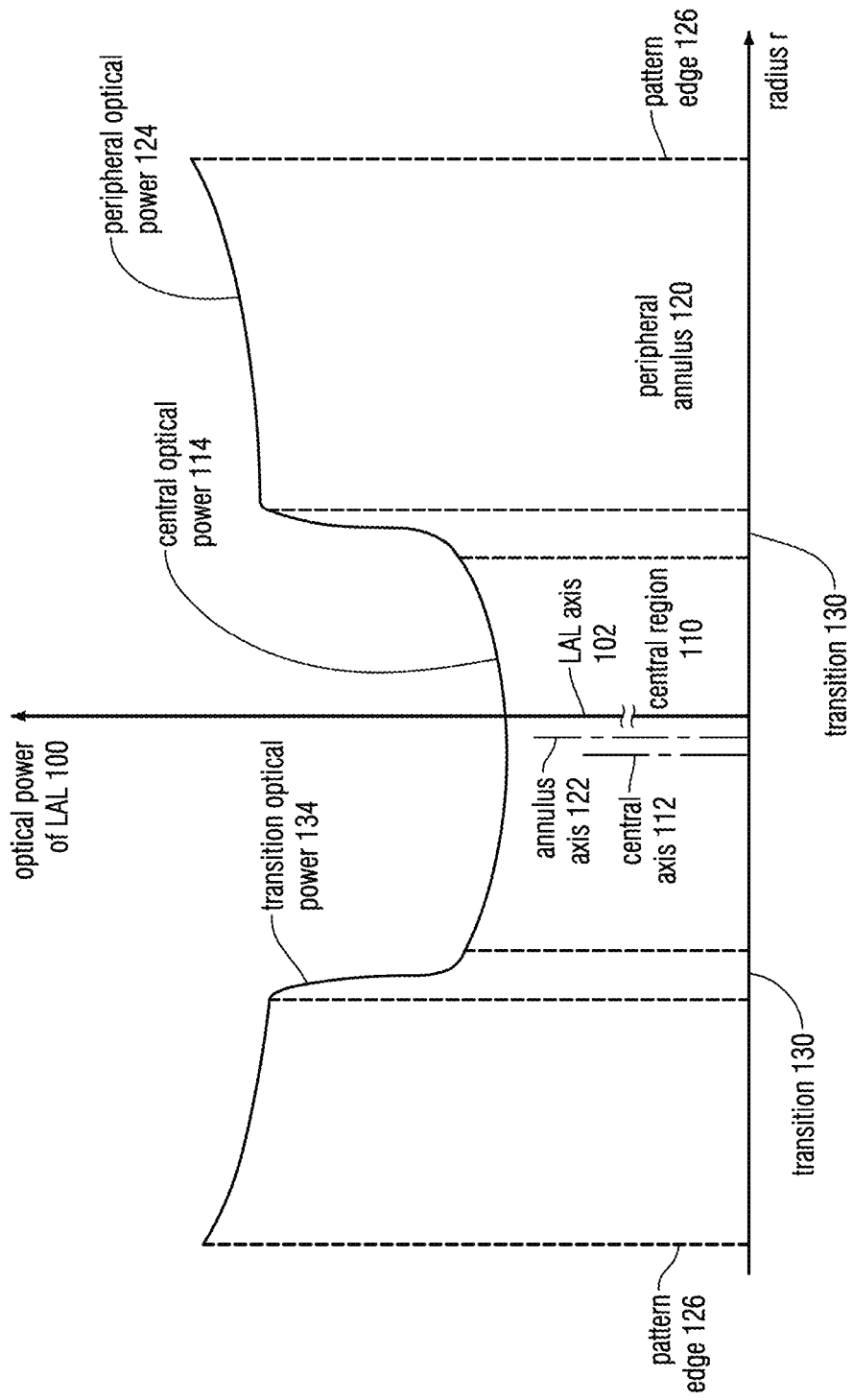

FIGS. 19 and 20A-C illustrate four of these eight possible combinations of the design factors. In FIG. 19, the central optical power 114 is still greater than the peripheral optical power 124, and the central optical power 114 still has a downward curvature. However, the peripheral optical power 124 has an upward curvature. Such optical designs also have an extended depth of focus, but the geometric relation between light rays from larger radii and smaller radii is reversed. In this design, the peripheral annulus 120 does not extend the depth of focus beyond the DOF extension induced by the central region 110. Instead, an advantage of the design of FIG. 19 is that it "fills in" the midrange log MAR minimum even more efficiently than previously described designs, thereby delivering an improved overall visual acuity.

FIGS. 20A-C show three embodiments, where the central optical power 114 is less than the peripheral optical power 124, at least in the above defined average sense. In these LALs 100, the central region 110 is providing good distance vision and the peripheral annulus 120 provides good near vision. In this sense, these embodiments and designs can be called Central Distance Add (CDA) LALs, or Peripheral Near Add (PND) LALs. These are less frequently used terms, as mentioned before.

In FIG. 20A, the central optical power 114 and the peripheral optical power 124 are both decreasing functions of the radius. In FIG. 20B, the central optical power 114 increases with the radius, while the peripheral optical power 124 decreases with the radius. In FIG. 20C, the central optical power 114 and the peripheral optical power 124 are both increasing functions of the radius.

In any of the above embodiments of the blended LAL 100, the central optical power 114 can be a quadratic function of the radius from the central axis 112 over the central region 110, optionally having a small correction term, or can have a quadratic component. In some of the cases, the peripheral optical power 124 can be a quadratic function of the radius from the annulus axis 122 over the annular region 120, optionally with a small correction term, or can have a quadratic component. To characterize these embodiments, it is recalled that the radius dependent optical power P(r) is related to the wavefront W(r) as:

$$P(r) = \frac{1}{r}\frac{dW(r)}{dr} \qquad (5)$$

Therefore, the above-described quadratic functions or components of the optical power P(r) correspond to a wavefront aberration proportional to the fourth power of the radius. The simplest fourth order aberration is the angle independent spherical aberration, or SA, its coefficient often denoted by Z(4,0), or Z12 in Zernike notation. Thus, embodiments of the blended LAL 100, where the position dependence of the optical power P(r) has a quadratic function or component, can be also characterized by a corresponding spherical aberration. Below, ranges of the spherical aberrations SA of some blended LALs 100 will be characterized. The described SA values can be induced by the peripheral optical power 124 alone, or by a combination of the central optical power 114, the peripheral optical power 124, and the transition optical power 134 of the blended LAL 100. An example of the former case is a pre-molded LAL 100, where a spherical aberration has been molded into the LAL 100, including into its peripheral annulus 120, measured before the central region 110 has been formed. An example of the latter case is a LAL 100, where the central region 110 has been already formed, typically after implantation.

In some blended LALs 100, the spherical aberration with one of the above definitions can be in the −0.05 μm to −1 μm range at a diameter of 4 mm in a plane of the LAL. In some embodiments, the spherical aberration can be in the −0.05

μm to −0.35 μm range at a diameter of 4 mm in a plane of the LAL. In yet other embodiments, the spherical aberration can be in the −0.10 μm to −0.25 μm range at a diameter of 4 mm in a plane of the LAL.

As noted above, these LAL-plane SA values translate to SA values measured at a 6 mm diameter at the corneal plane approximately by a scale factor of about 2.6, or in a range around 2.6, such as the range of 2.4-2.8, or 2.2-3.0. Since the translation factor can vary over these narrow, but finite ranges, corneal plane SA values will be expressly described next. This translation of the SA values can be particularly useful if the SA of an implanted LAL 100 needs to be determined without explanting the LAL 100 from the patient's eye. For example, the −0.05 μm to −1 μm SA range at a diameter of 4 mm at the LAL plane can translate to an approximately −0.13 μm to −2.6 μm SA range at a diameter of 6 mm in the corneal plane. In other embodiments of the blended LAL 100 implanted in an eye, the SA, measured at a 6 mm diameter at the corneal plane, can be in the range of −0.05 μm to −2 μm; in yet other embodiments, in the range of −0.1 μm to −0.6 μm, or in the range of −0.2 μm to −0.4 μm.

As described next, when the spherical aberration is measured in an eye with an implanted LAL 100, the measurement results will be impacted by the spherical aberration of the eye before the implantation. Therefore, the SA attributed to the implanted LAL 100 alone is to be extracted from the SA values measured for the entire eye.

In the context of measuring the SA of an eye with an implanted LAL 100, it is recalled that the cornea has its own spherical aberration SA(cornea). Over a large patient population this corneal SA(cornea) has a distribution. An average, or mean, of this distribution is described in some studies to be around SA(cornea)=+0.26 μm, with a standard deviation of about ±0.13 μm at the corneal plane with a 6 mm diameter. Other studies report mean values between +0.20 μm and +0.30 μm, with correspondingly varying standard deviation. The SA of the combined ophthalmic optical system of the cornea 15 and the implanted LAL 100 will have an SA(combined)=SA(LAL)+SA(cornea), with both SA values measured at the same plane and radius. For example, if the LAL 100 is known to have a SA in the range of −0.10 μm to −0.25 μm at a 4 mm diameter in the LAL plane, then first this SA is to be translated to a SA at a 6 mm diameter in the corneal plane. Using the translational factor of 2.6, corresponding to the average corneal power, the SA(LAL, d=4 mm, LAL plane)=−0.10 μm to −0.25 μm range translates to a SA(LAL, d=6 mm, corneal plane)=−0.26 μm to −0.65 μm range. Second, the SA of the combined ophthalmic optical system of the cornea 15 and the implanted LAL 100 can be determined by combining this SA(LAL, d=6 mm, corneal plane) with the SA(cornea) of the corneal at the same 6 mm diameter in the same corneal plane: SA(combined)=SA(LAL, d=6 mm, corneal plane)+SA(cornea). With the above values, SA(combined) at the 6 mm diameter in the corneal plane in embodiments can be in the range of 0 μm to −0.39 μm in case of an eye with an average SA(cornea). In other embodiments, again measured at d=6 mm at the corneal plane, the combined spherical aberration of an eye with an implanted LAL 100, the SA(combined) can fall within the −0.05 μm to −0.5 μm range. In yet other embodiments, SA(combined) can fall in the −0.1 μm to −0.2 μm range.

The same consideration can be used in reverse to determine the SA(LAL, d=6 mm, corneal plane) of a LAL 100 implanted into the eye of a particular patient, by measuring the SA(combined) of the patient's eye, and then subtracting from it the patient's specific corneal SA(cornea). From the so-determined SA(LAL, d=6 mm, corneal plane), the SA(LAL, d=4 mm, LAL plane) can then be determined by the above translation factor, as needed.

Another calculus can be useful to reconstruct SA(pre-mold), the pre-molded portion of the SA for an implanted LAL 100, where the CNA, or central region 110 has been already formed. This SA(pre-mold) can be related to the entire LAL 100, or to the peripheral annulus 120. After the implantation of the LAL 100, the SA(pre-mold) is shifted with a ΔSA(CNA) by the formation of the CNA, or central region 110. Therefore, the SA(pre-mold) can be reconstructed by measuring the SA of the entire implanted LAL 100, and then subtracting appropriate ΔSA(CNA) values. In some embodiments, at d=6 mm in the corneal plane, ΔSA(CNA) can take values in the −0.01 μm to −0.4 μm range, in others in the −0.05 μm to −0.2 μm range. The formation of the CAN, or central region 110 often shifts the SA(LAL) value relatively little because the diameter of the CAN, or central region 110 is often small, in the range of 0.5 mm to 1.5 mm, and the value of the spherical aberration SA scales with the fourth power of the diameter.

In some embodiments of the blended LAL 100, a spherical aberration caused by the position-dependence of the central optical power 114, the peripheral optical power 124, or their combination, can be selected to approximately compensate a spherical aberration of the cornea 15 of the eye. In such embodiments, the optical aberrations of the combined optical system of the cornea 15 and the LAL 100 are minimized.

For completeness, it is mentioned that once the central region 110 and the transition 130 have been formed, the latter with its fast-changing transition optical power 134, the optical powers 114/124/134 often deviate substantially from a quadratic function of the radius, and thus induce higher order aberrations beyond the Z(12) spherical aberration.

Another type of aberration, a coma is induced when an IOL with a pre-molded spherical aberration (an SA IOL) is shifted off the optical axis. In Zernike notation, the coma is represented by the Zernike coefficient Z8, and the spherical aberration by 212. A Δx off-axis shift of an SA IOL induces a coma given by Eq. (6):

$$Z8 = \frac{2\sqrt{10}\,\Delta x\,Z12}{r}, \qquad (6)$$

Embodiments of the LAL 100 can mitigate this coma aberration, even if the LAL 100 is shifted off-axis. Using embodiments of the LAL 100 where the peripheral annulus 120 is formed only after the LAL 100 settled can preempt this problem entirely, as the peripheral annulus 120 can be formed with an annulus axis 122 that is centered on the visual axis 132. In some cases, this can be achieved by shifting the annulus axis 122 with a shift that is equal and opposite to the Δx off-axis shift of the LAL 100. The peripheral annulus 120 can be centered on the visual axis 132, e.g., by registering the visual axis 132 prior to dilating the iris 5.

In some embodiments of the blended LAL 100, further aberrations of the patient's vision can be mitigated. A notable example is that in some LALs 100 the position-dependent central optical power 114 can involve a cylinder angular dependence. In some LALs 100 the position-dependent peripheral optical power 124 can involve a cylinder angular dependence. Forming a cylinder in either the central region 110 or in the peripheral annulus 120 can mitigate an existing cylinder in the patient's eye.

Figure 21A:
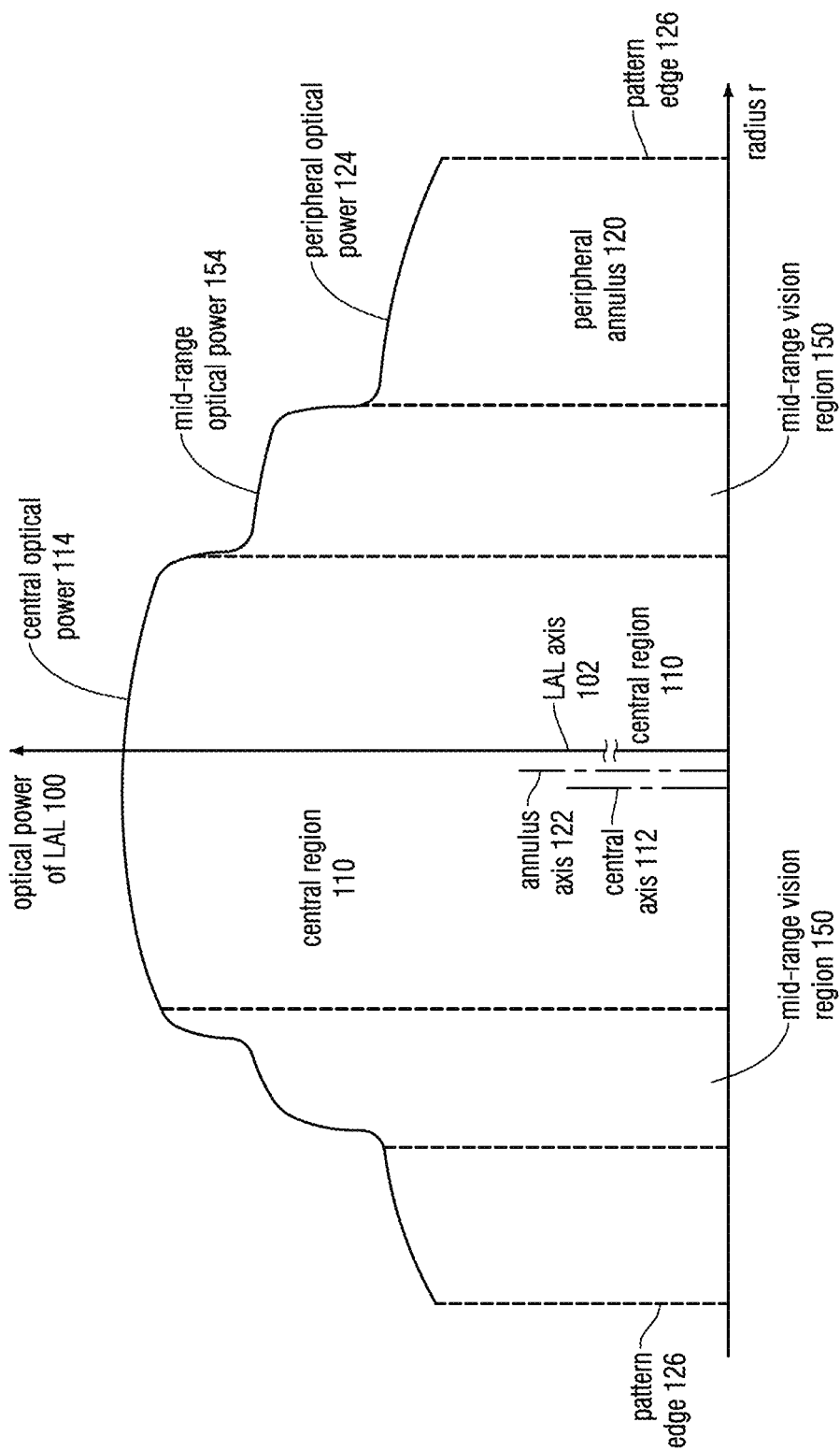
FIGS. 21A-B illustrate a LAL with a mid-range vision region.
Figure 21B:
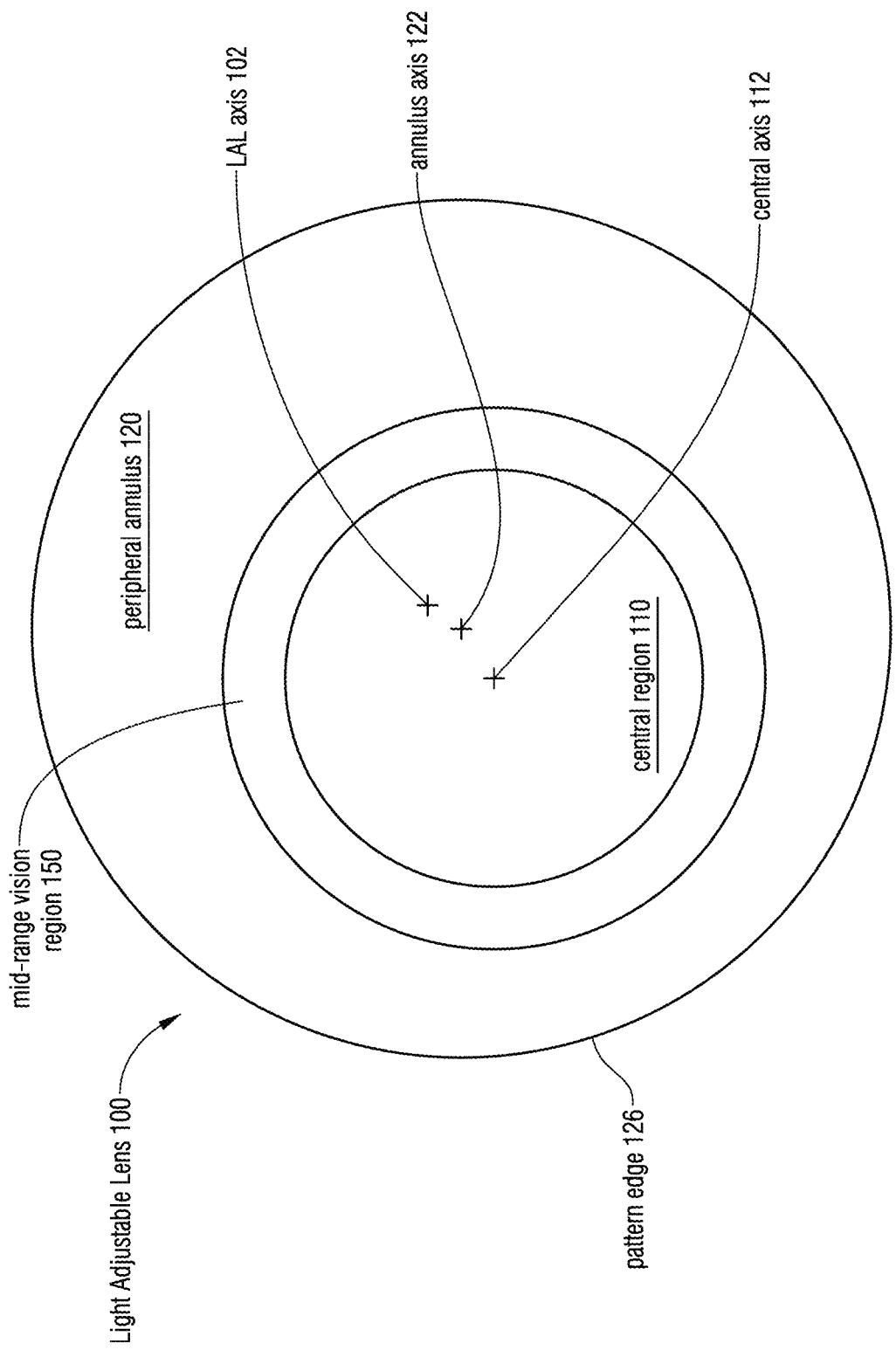

FIGS. 21A-B illustrate that some embodiments of the blended LALs 100 can include an annular mid-range vision region 150, positioned between the central region 110 and the peripheral annulus 120. The mid-range optical power 154 of this mid-range vision region can be selected to improve vision at medium ranges, such as at distance around 1 meter. An axis of the mid-range vision region 150 can coincide with the LAL axis 102, the central axis 112, or the annulus axis 122. In some aspects, the mid-range vision region 150 may be viewed as part of the transition 130.

In some embodiments of the LAL 100, the first illumination 222 induces the position-dependent peripheral optical power 124, and the second illumination 242 induces the position-dependent central optical power 114 primarily by inducing a shape change of the LAL 100 via activating a photopolymerization process. In other embodiments, the same illuminations 222 and 242 induce the optical powers 114 and 124 primarily by changing an index of refraction of the LAL 100, in effect transforming the LAL 100 into a Gradient Index of Refraction, or Graded Index of Refraction, (GRIN) lens. In yet other embodiments, the illuminations 222 and 242 induce the optical powers 114 and 124 by a combination of shape change and index of refraction change.

Figure 22:
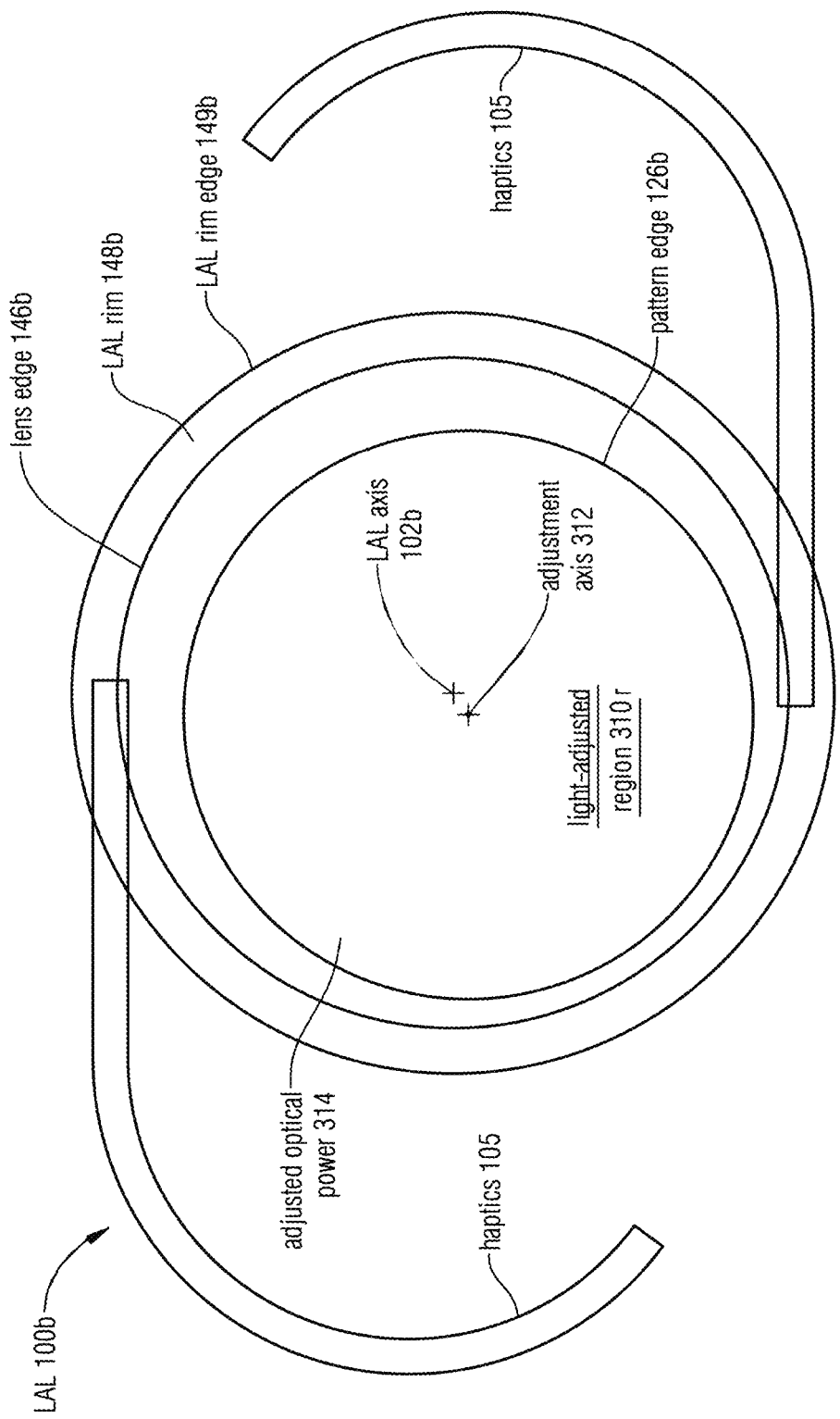
FIG. 22 illustrates a LAL with a light-adjusted region, with a shifted adjustment axis.

FIG. 22 illustrates a unifying aspect of the LALs 100b depicted in FIGS. 13-21. In broader terms, a Light Adjustable Lens (LAL) 100b can have a LAL axis 102b, and include a light-adjusted region 310r, centered on an adjustment axis 312, with a position-dependent adjusted optical power 314; wherein the adjustment axis 312 can be laterally shifted relative to the LAL axis 102b. The embodiments of FIGS. 13-21 are specific embodiments of this general LAL 100b design, where, e.g. the adjusted optical power 314 includes the central optical power 114, the peripheral optical power 124, or both. A unifying aspect of these embodiments is that, because they have an adjusted optical power 314 that was formed by adjusting the implanted LAL 100 after it settled and often shifted from its intended position in the capsular bag, the adjustment axis 312 is laterally shifted relative to the LAL axis 102b.

To relate the light-adjusted region 310r to the physical structure of the LAL 100b, beyond a pattern edge 126b, these LALs 100b can include a lens edge 146b, a LAL rim 148b, and a LAL rim edge 149b, as in FIGS. 14A-B.

Figure 23:
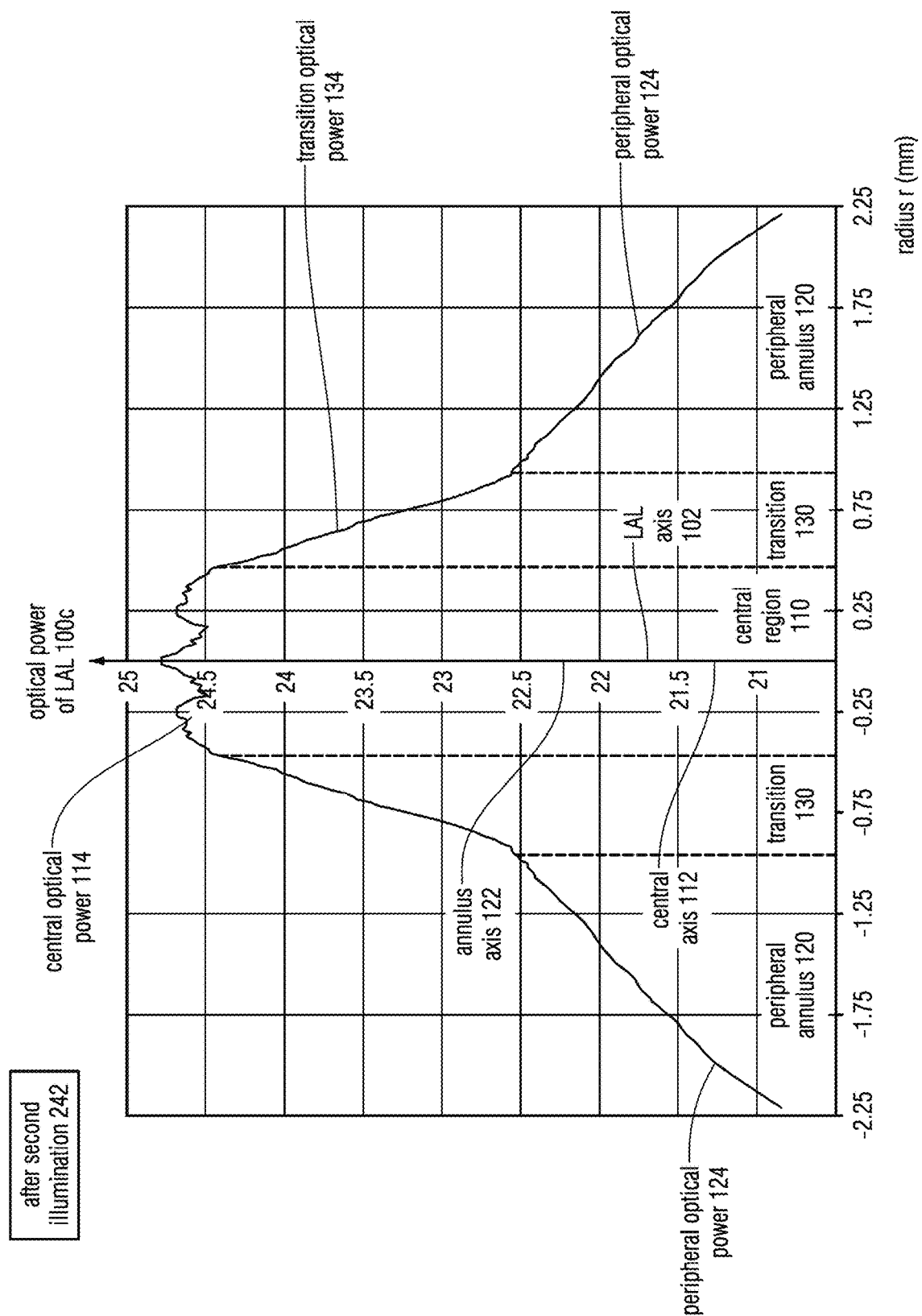
FIG. 23 illustrates the position dependent optical power of a LAL.

FIG. 23 illustrates a distinct case of a LAL 100c, where the central axis 112 is not shifted relative to the annulus axis 122; instead it coincides with it. In the shown embodiment of LAL 100, the central axis 112, the annulus axis 122 and the LAL axis 102 all coincide. This embodiment may emerge in multiple ways. One of them is that the visual axis 132 is determined after the iris 5 approximately returned into its non-dilated state, for example, during a subsequent office visit, and the surgeon found that none of the misalignment mechanisms (1)-(4) shifted the LAL axis 102 from the visual axis 132, and thus the central region 110 can be formed centered on the shared central axis 112/LAL axis 102. Another possibility is that for some reason, such as to reduce the number of office visits, the surgeon decides to form the CNA/central region 110 while the iris 5 is still dilated, in which case it is reasonable to form the CNA/central region 110 with a central axis 112 that coincides with the annulus axis 122. All aspects, details and descriptions related to the embodiments of FIGS. 13-22 can be combined with the blended LAL 100c of FIG. 23.

Figure 24:
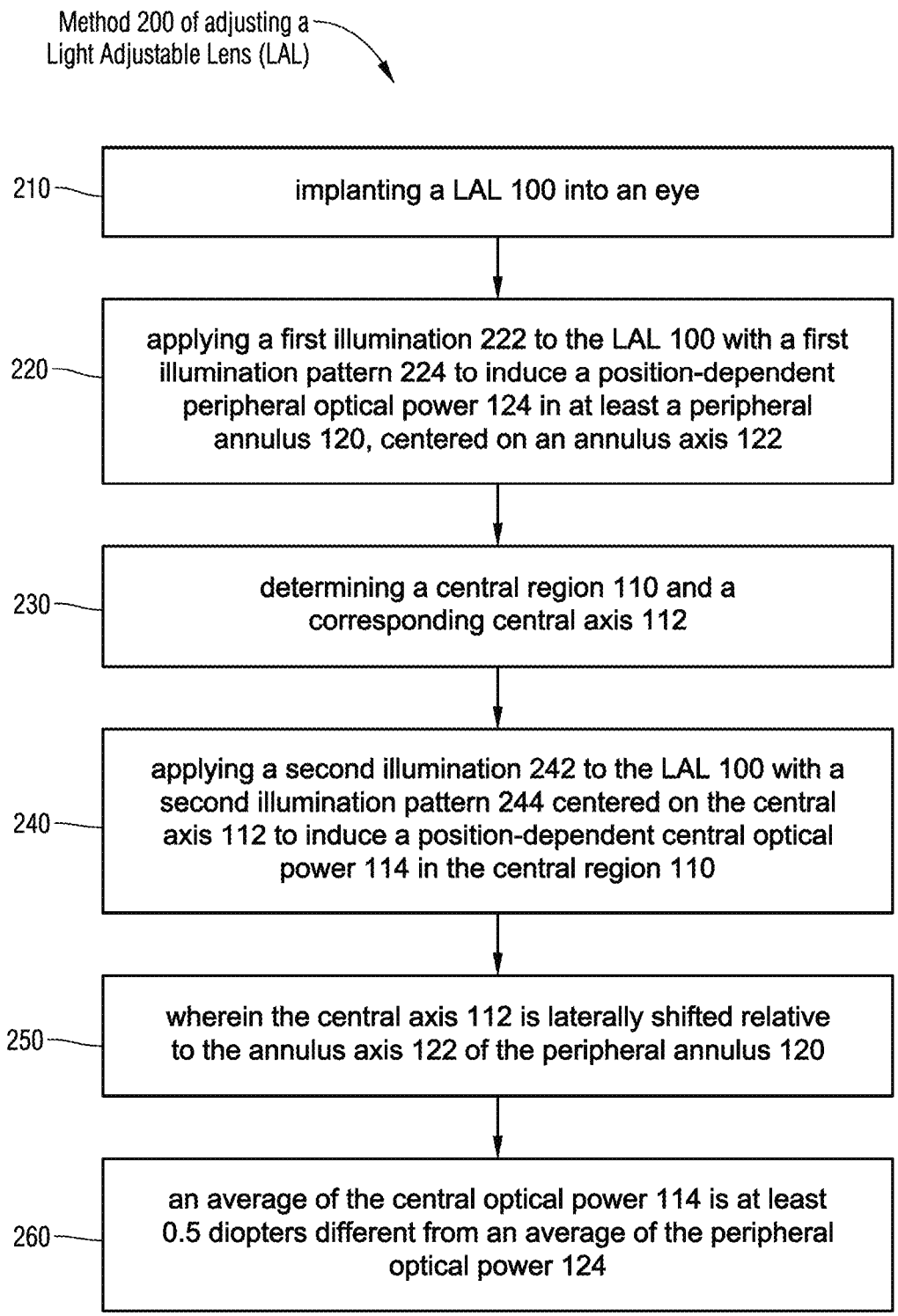
FIG. 24 illustrates a method of adjusting the LAL.

FIGS. 24-30 describe methods of light adjustment of the blended LALs 100. FIG. 24 shows that a method 200 of adjusting a Light Adjustable Lens (LAL) 100 can include the following steps.

Implanting 210 a LAL 100 into an eye;

Applying 220 a first illumination 222 to the LAL 100 with a first illumination pattern 224 to induce a position-dependent peripheral optical power 124 in at least a peripheral annulus 120, centered on an annulus axis 122;

Determining 230 a central region 110 and a corresponding central axis 112 of the LAL; and Applying 240 a second illumination 242 to the LAL 100 with a second illumination pattern 244 to induce a position-dependent central optical power 114 in the central region 110 of the LAL 100; wherein (250) the central axis 112 is laterally shifted relative to the annulus axis 122 of the peripheral annulus 120, and (260) an average of the central optical power 114 is at least 0.5 diopters different from an average of the peripheral optical power 124.

In embodiments of the method 200, the average of the central optical power 114 can be at least 1.0 diopter different from the average of the peripheral optical power 124.

In some embodiments, the average of the central optical power 114 can be at least 0.5 diopters higher than an average of the peripheral optical power 124. The LALs 100 formed with such embodiments can be called Central Near Add, or CNA LALs. In other embodiments, the average of the central optical power 114 can be at least 0.5 diopters lower than an average of the peripheral optical power 124. The LALs 100 formed with such embodiments can be called Central Distance Add (CDA), or Peripheral Near Add (PNA) LALs.

In some embodiments of the method 200, the applying 220 of the first illumination 222 can include applying the first illumination 222 with a first illumination pattern 224 to induce the position-dependent peripheral optical power 124 in a light-adjusted region that includes the peripheral annulus 120 and the central region 110. In other embodiments, the first illumination pattern 224 is concentrated mostly on the peripheral annulus 120, and an amplitude of the first illumination pattern 224 can be greatly reduced in the central region 110.

As described in relation to FIGS. 13-23, an advantage of the design of the blended LAL 100 is that its central axis 112 can be aligned with the eye's visual axis 132. Accordingly, in embodiments of the method 200, the determining 230 of the central axis 112 can include identifying the visual axis 132 of the eye as the central axis 112.

Figure 25A:
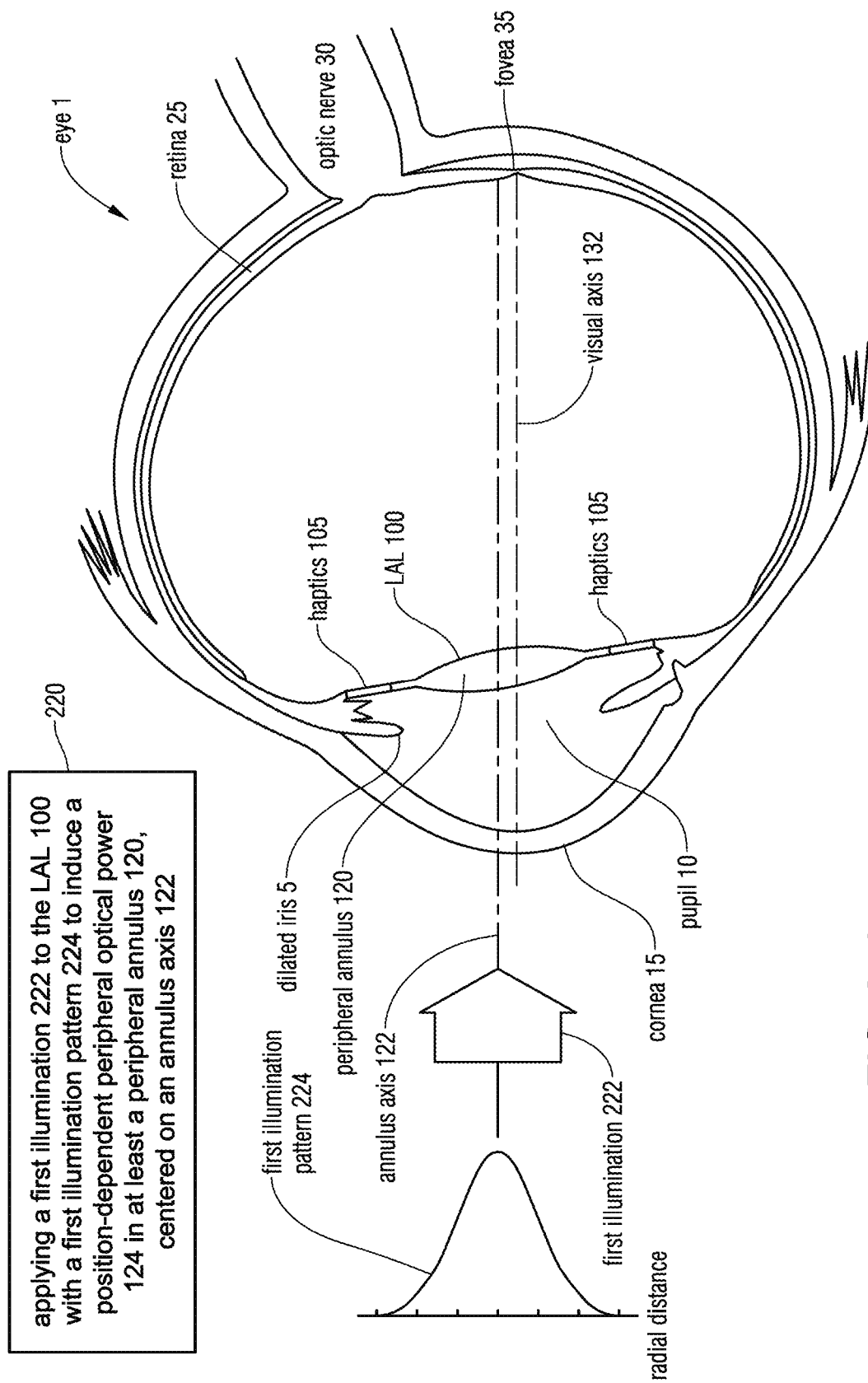
FIGS. 25A-B illustrate applying the first illumination and the second illumination to the LAL within the method.
Figure 25B:
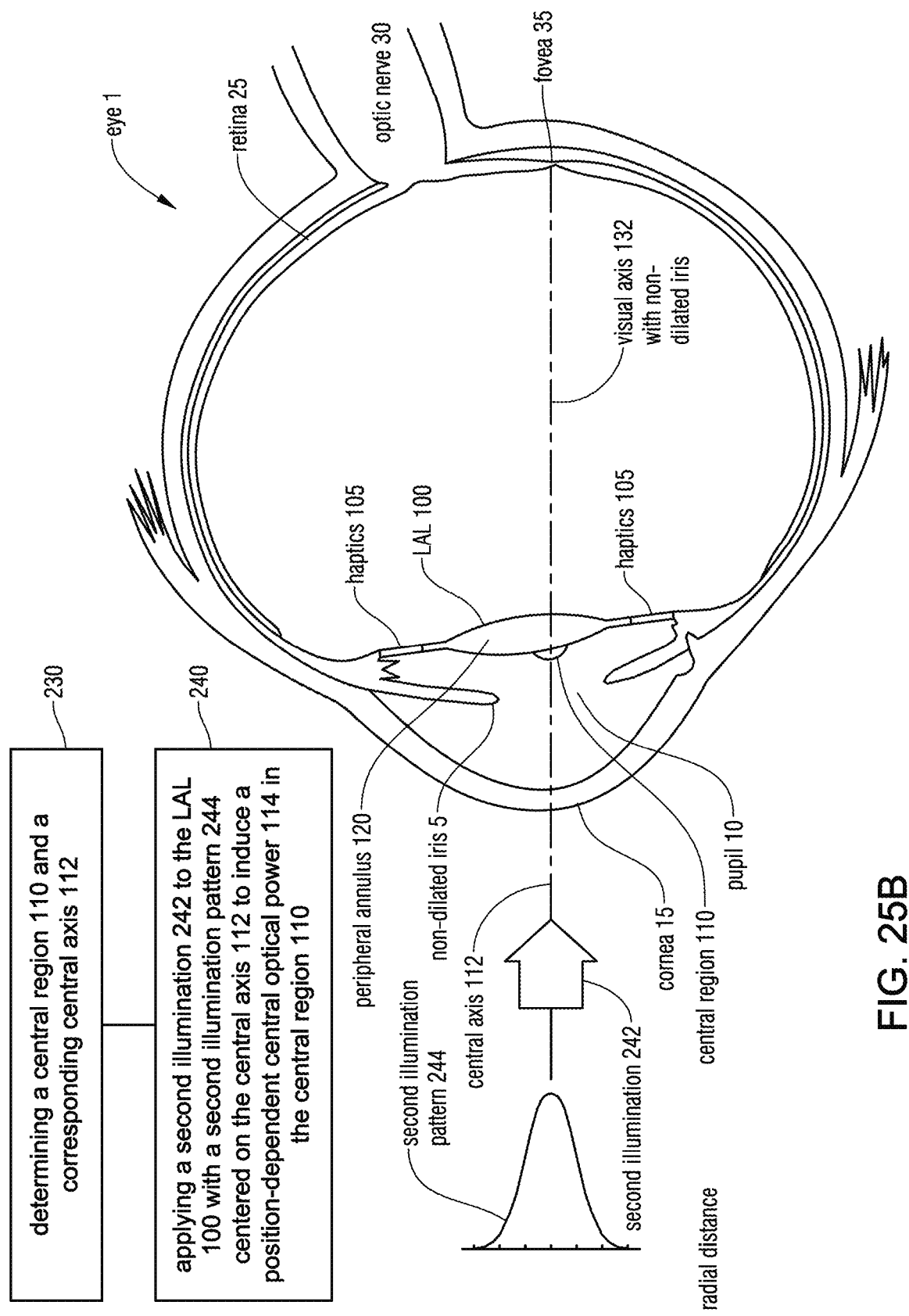

FIGS. 25A-B illustrate that, since the iris 5 can return to its non-dilated state in an asymmetric manner, this determining step 230 of the central axis 112 can be performed with an iris 5 of the eye being in, or returned to, a non-dilated state in order to achieve a good alignment with the visual axis 132. In related embodiments, the eye does not need to fully return to its non-dilated state. In these embodiments, the determining 230 of the central axis 112 can include determining the central axis 112 with the iris 5 of the eye being dilated to an iris-radius no more than 30% greater than a non-dilated iris-radius. In other words, to perform the determining 230 when the iris is only in the process of returning to its non-dilated state, but the return is only partial and the iris did not reach the non-dilated state fully.

In some other embodiments of the method 200, the determining 230 of the central axis 112 can include determining the central axis 112 before the iris 5 of the eye is dilated and registering the determined central axis 112 with a feature of the eye. In these embodiments the determined and registered central axis 112 can be reconstructed after the iris is dilated, but before the applying 240 of the second illumination 242. In some cases, the registration of the determined central axis 112 can be carried out with respect to retinal features, in other cases, with respect to features of the iris, limbus, or sclera of the eye. The determining of the central axis 112 can involve determining the visual axis 132 of the eye with the iris 5 being non-dilated, and then simply defining the central axis 112 as the determined visual axis 132. An advantage of this approach is that the doctor does not have to wait during the surgery for the iris 5 to slowly return to its largely non-dilated state; or, does not have to schedule a separate subsequent procedure to apply the second illumination 242.

In this embodiment of the method 200, the sequence of the applying 220 of the first illumination 222 and the applying 240 of the second illumination 242 can be interchanged, since the availability of the registered central axis 112 eliminates the need to wait for the iris 5 to relax after the applying 220. The sequence of the applying step 220 and the applying step 240 can be also interchanged in embodiments of the method 200 where the iris 5 is dilated not at the beginning of the procedure, but only after the firstly-performed applying 240 of the second illumination 242 has been completed. Finally, in some embodiments, the applying 240 of the second illumination 242 can be performed before the applying 220 of the first illumination 222, both with the iris dilated. In these embodiments, it may be somewhat challenging to align the central axis 112 with the visual axis 132.

As shown in FIGS. 13-23, the applying 220 of the first illumination 222 and the applying 240 of the second illumination 242 can induce a transition 130 between the central region 110 and the peripheral annulus 120, having a transition optical power 134 that changes from the central optical power 114 to the peripheral optical power 124.

FIG. 16 illustrates that the method 200 can be performed to create "flat top" blended LALs 100. In these LALs 100 the central optical power 114 can have an approximately flat position-dependence, having an optical power variation less than 0.2 diopters over a central 50% of the central region 110. In some other embodiments, the central optical power can have an optical power variation greater than 0.2 diopters over the central 50% of the central region 110.

As before, the central optical power 114 can be a quadratic function of the radius from the central axis 112 over a quadratic central region, optionally having a small correction term. As described in relation to Eq. (5), such a quadratic radius dependence of the optical power induces a fourth order spherical aberration, discussed further below.

Also, in some embodiments, the peripheral optical power 124 can have an approximately flat position-dependence, having an optical power variation less than 0.2 diopters over 50% of the peripheral annulus 120. In other embodiments, the peripheral optical power 124 can be a function of a radius from the annulus axis 122, having an optical power variation greater than 0.2 diopters over 50% of the peripheral annulus 120. The peripheral optical power 124 can be a quadratic function of the radius from the annulus axis 122 over a quadratic annular region, optionally with a small correction term.

The mentioned quadratic radius dependence of the peripheral optical power 124 can also induce, or cause, a spherical aberration (SA) in the −0.05 µm to −1 µm range at a diameter of 4 mm in a plane of the LAL 100. In some embodiments, the spherical aberration caused by the position-dependence of the peripheral optical power 124 can be in the −0.10 µm to −0.25 µm range at a diameter of 4 mm in a plane of the LAL 100. These LAL-plane, d=4 mm diameter SA values can be translated into corneal plane, d=6 mm SA values with a translation factor, which in a wide class of cases is about 0.26, as calculated earlier.

In some embodiments of the method 200, at least one of the central optical power 114 and the peripheral optical power 124 can be selected such that a spherical aberration caused by the position-dependence of the selected central optical power 114 or peripheral optical power 124 approximately compensates a spherical aberration of the cornea 15 of the eye. As described before, such a selection can minimize, or even eliminate, the inducing of aberrations in the eye's optical system, by a postsurgical shift of the LAL 100.

In embodiments of the method 200, the applying 220 of the first illumination 222, or the applying 240 of the second illumination 242 can further include inducing the position-dependent central optical power 114 with a cylinder angular dependence, or inducing the position-dependent peripheral optical power 124 with a cylinder angular dependence. These embodiments of the method 200 can mitigate not only presbyopia, but also cylinder aberrations of the eye. The inducing of a cylinder in the central region 110 or in the peripheral annulus 120 can be performed before, simultaneously, or after the applying steps 220 or 240. The numerous sequences and combinations of the (1) applying 220 of the first illumination 222; (2) applying 240 of the second illumination; and (3) inducing the cylinder, can all be embodiments of the method 200.

In some embodiments of the method 200, the applying 220 of the first illumination 222 and the applying 240 of the second illumination 242 can be separated by less than 48 hours. In some embodiments, these two applying steps 220 and 240 can even be performed as part of a single, integrated procedure, separated by only a short time, thus reducing the demands on the surgeon and the patient.

Also, once all the light adjusting steps of the method 200 have been performed, a lock-in illumination can be applied to the LAL 100, in order to lock in the induced peripheral optical power 124 and the induced central optical power 114 in the LAL 100. This step can be necessary to lock in the specific shape of the LAL 100 by de-activating all remaining photopolymerizable macromers still in the LAL 100, as described, e.g., in the incorporated U.S. Pat. No. 6,905,641, to Platt et al, and in U.S. Pat. No. 7,281,795, to Sandstedt et al., among others.

Figure 26:
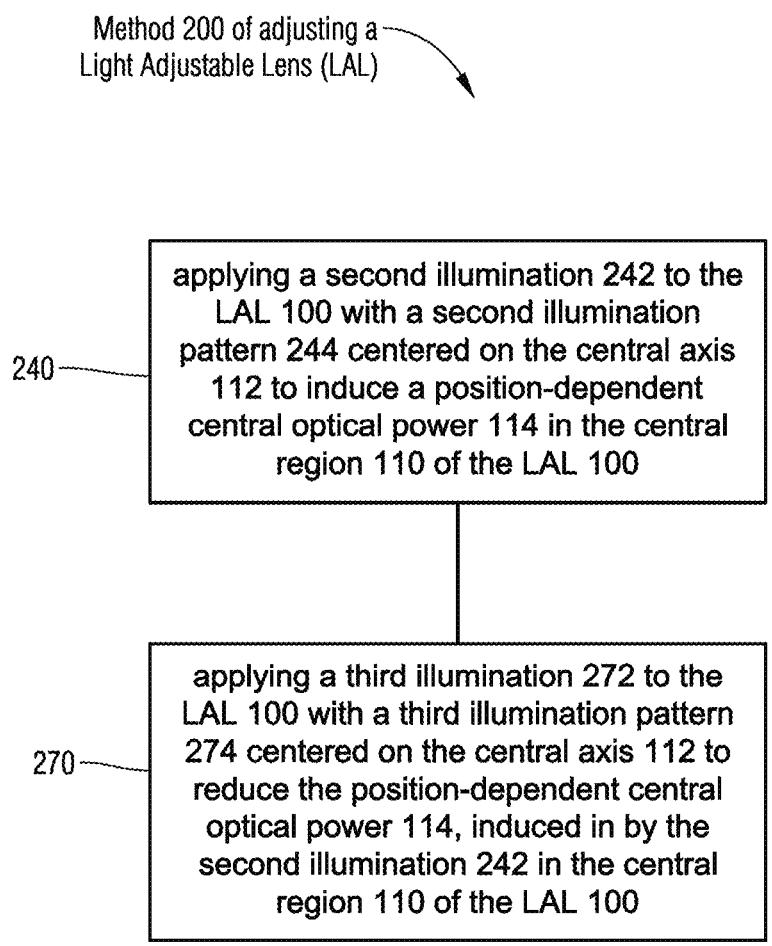
FIG. 26 illustrates applying a third illumination to the LAL.
Figure 27A:
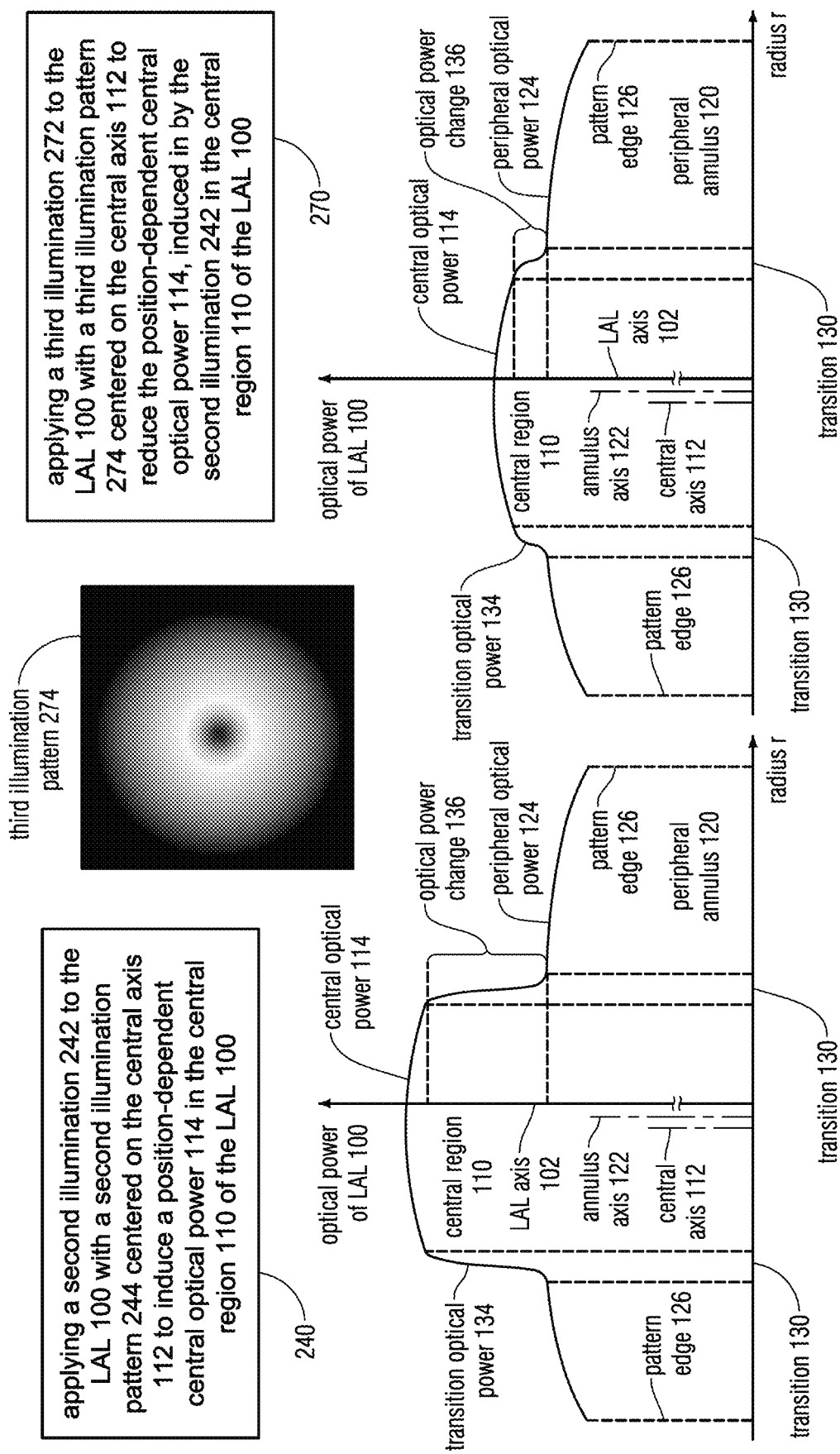
FIGS. 27A-B illustrate applying the second and third illumination to the LAL.
Figure 27B:
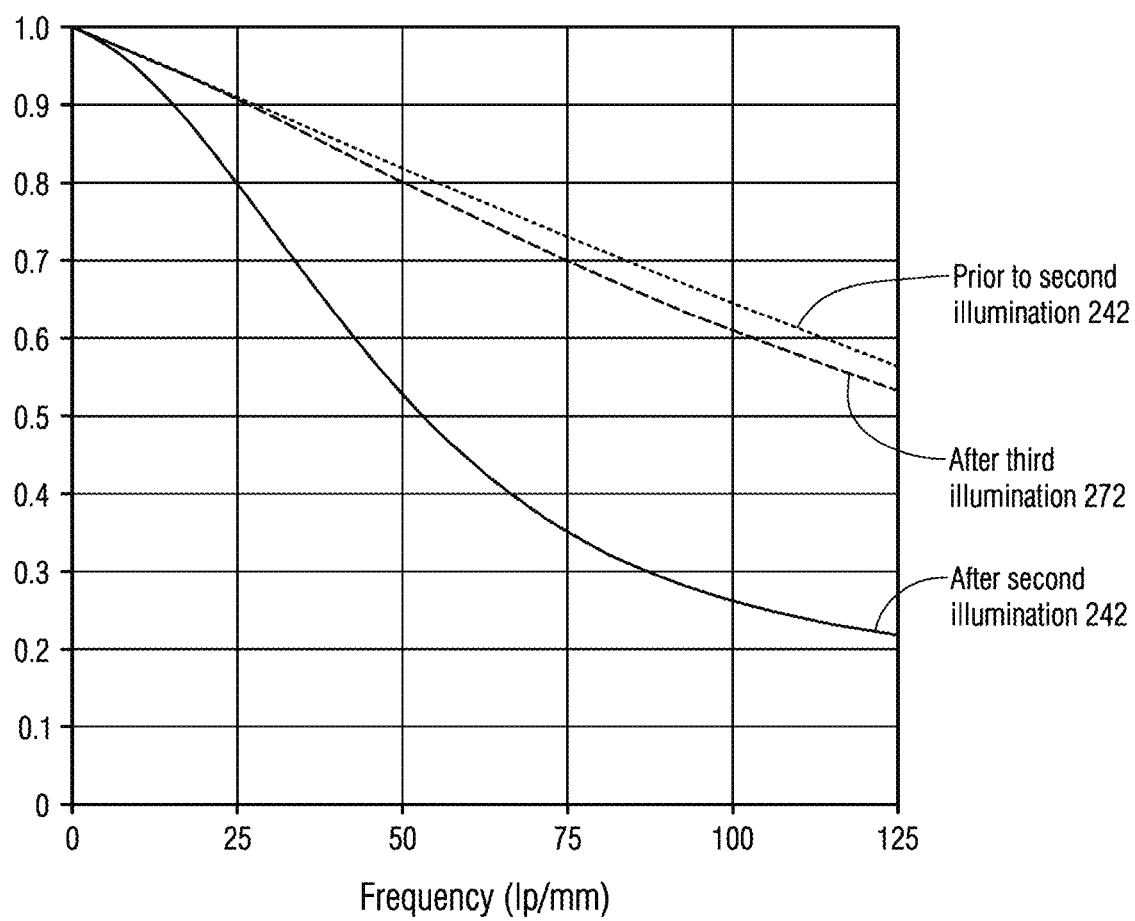

FIG. 26 and FIGS. 27A-B illustrate an additional advantage of the method 200. In some cases, the patient may ask the surgeon to form the CNA central region 110 in the implanted LAL 100, but after the procedure may be dissatisfied with the outcome and demand a corrective procedure. This can happen if the CNA central region 110 caused undesired or disorienting blurriness, or halos, or both. Had the surgeon implanted a non-light-adjustable CNA IOL, such a patient demand would be impossible to satisfy. In contrast, having implanted a blended LAL 100 enables the surgeon to perform a "CNA erasure" process. The surgeon may perform an applying 270 of a third illumination 272 to the LAL 100 with a third illumination pattern 274 centered on the central axis 112 to reduce the position-dependent central optical power 114, induced in by the second illumination 242 in the central region 110 of the LAL 100. FIG. 27A, left panel re-describes the LAL 100 as formed by the steps 210-260 of the method 200. FIG. 27A, right panel illustrates that performing of the additional applying step 270 of the third illumination 272 to reduce the central optical power 114. This reduction is captured, e.g., in that the optical power change 136 between the central optical power 114 and the peripheral optical power 124 is visibly reduced by the applying 270 of the third illumination 272. FIG. 27A, central panel shows a third illumination pattern 274 that is intense in the peripheral annulus 120 but has low intensity in the central region 110, and therefore can be suitable for the applying 270 of the third illumination 272.

FIG. 27B illustrates that the applying the third illumination 272 can largely restore the patient's visual acuity. The plot shows an often-used measure of visual acuity, the Modulation Transfer Function, or MTF, as a function of its natural variable, the frequency, measured in line pairs per mm, or lp/mm. Visibly, the MTF gets reduced from its value prior to the second illumination 242 that formed the CNA central region 110 to lower values after the second illumination 242, since the CNA central region 110, while it improves the patient's near vision, it also enhances optical various aberrations. The reduction is more pronounced at higher frequencies. Importantly, the plot demonstrates that the MTF can be restored to essentially the pre-second-illumination levels by applying of the third illumination 272.

In some embodiments, after the second illumination 242 the patient may be dissatisfied with the outcome and demand a corrective procedure, but with an opposite goal. The patient may report to the doctor no visual acuity problems caused by the CNA central region 110, but instead may find that not enough power was added. In such cases, the third illumination 272 may be used with a third illumination pattern 274 to enhance the central optical power 114 in the central region 110.

Figure 28:
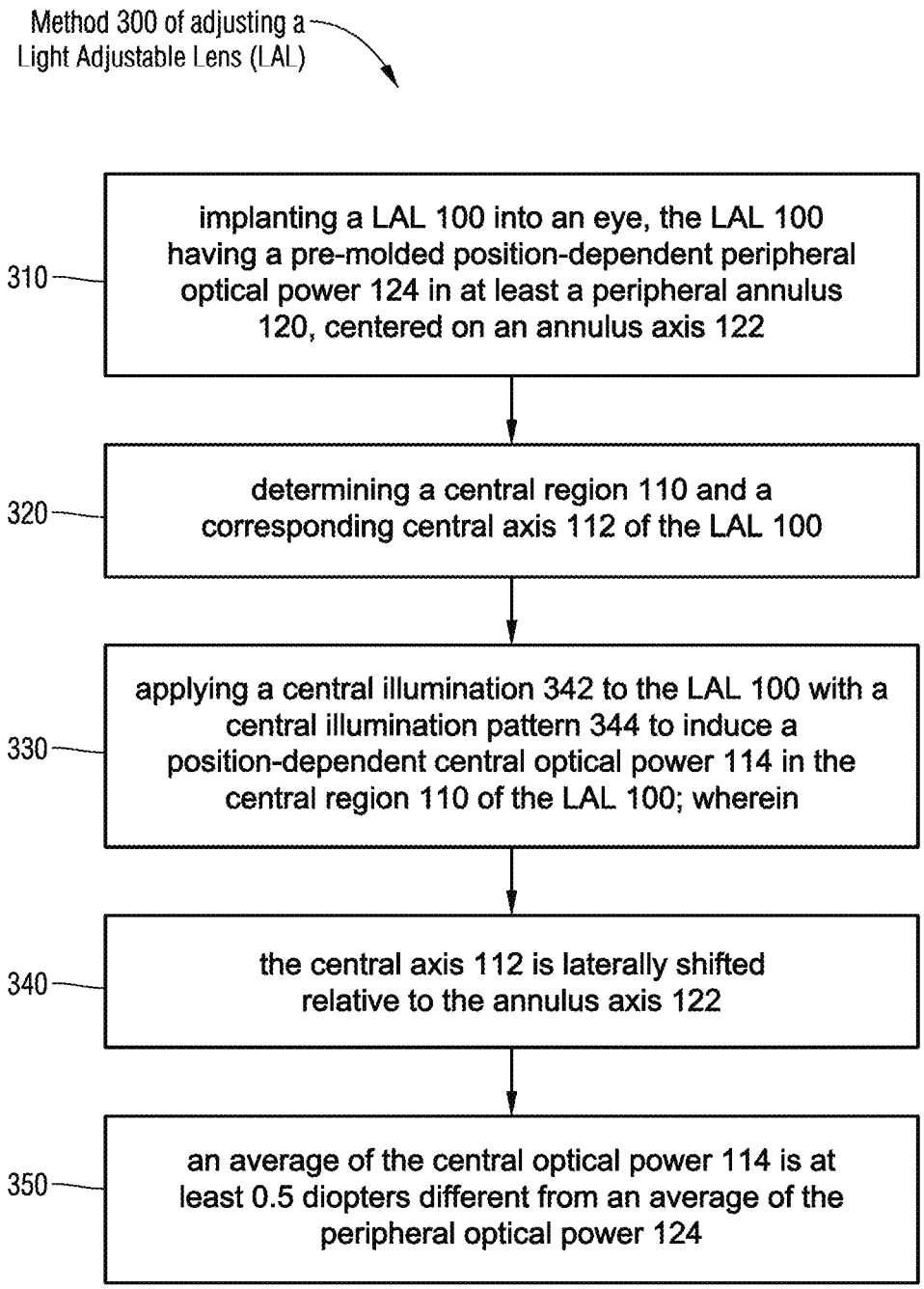
FIG. 28 illustrates a method of adjusting the LAL with a pre-molded LAL.

FIG. 28 illustrates a method 300 of adjusting the Light Adjustable Lens (LAL) 100, related to the method 200. The method 300 can comprise the following steps.

Implanting 310 a LAL 100 into an eye, the LAL 100 having a pre-molded position-dependent peripheral optical power 124 in at least a peripheral annulus 120, centered on an annulus axis 122;

Determining 320 a central region 110 and a corresponding central axis 112 of the LAL 100; and Applying 330 a central illumination 342 to the LAL 100 with a central illumination pattern 344 to induce a position-dependent central optical power 114 in the central region 110 of the LAL 100, wherein (340) The central axis 112 is laterally shifted relative to the annulus axis 122, and (350) An average of the central optical power 114 is at least 0.5 diopters different from than an average of the peripheral optical power 124.

A difference between the method 200 and this method 300 is the manner in which the position dependent peripheral optical power 124 is formed. In the method 200, the peripheral optical power 124 is formed by the applying 220 of the first illumination 222 to the already implanted LAL 100. In contrast, in the method 300, this same peripheral optical power 124 is pre-formed, prior to the implantation of the LAL 100, during the molding process of the manufacture of the LAL 100. A benefit of the method 200 is that the positioning and the magnitude of the peripheral annulus 120 can be adjusted based on a measurement of the postsurgical shifts of the LAL 100. Another benefit is that the magnitude and position dependence of the peripheral optical power 124 can be customized to the individual need of the specific patient. A drawback can be that doing so may require an additional procedure, with the necessary scheduling and organization and an extra trip for the patient. (It is noted that this demand can be reduced in some cases by performing the applying step 220 and the applying step 240 during a single visit by the patient. This may require accelerating the iris 5 returning to its non-dilated state by pharmacological means.)

In contrast, benefits of the method 300 include that it starts with a LAL 100 that already has a pre-molded position-dependent peripheral optical power 124. In a sense, this method 300 starts with an EDOF LAL, and the method concentrates on adding a CNA to this EDOF LAL. Therefore, the method 300 does not require the applying 220 of the first illumination 222, and thus has one less procedure step. This beneficially reduces the number of office visits for the patient. Potential drawbacks include that the positioning of the peripheral annulus 120 and the magnitude of the peripheral optical power 124 may not be adjusted in response to a measurement of the postsurgical shift of the LAL 100.

However, simple geometric considerations suggest that the total optical power accommodation necessary to mitigate presbyopia, i.e. to cover the range from near targets (d=0.4-0.5 m, i.e. 2-2.5 D) to distance targets (approx. 0 D) is about 2-2.5 D. This is to be delivered by the combination of the higher central optical power 114 of the CNA central region 110 and the position-dependent variation of the EDOF peripheral optical power 124. Therefore, embodiments of the LAL 100 that combine a pre-molded optical power 124 with a radial variation of 0.5-1 D with a customized addition of 1-2 D of central optical power 114 post-implantation, may be able to deliver all the benefits of the blended CNA+EDOF LAL designs, even without customizing the peripheral optical power 124 by applying 220 the first illumination 222 post-implantation. Moreover, surgeons may be provided with a series of LALs with different amounts of radial peripheral optical power variations, and thus different SAs, pre-molded into them. This may enable the surgeon to select a LAL with the pre-molded SA and position dependent peripheral optical power 124 that is most suitable for the patient's individual need. All in all, both the method 200 and the method 300 have advantages and drawbacks, and the surgeon may decide between them based on the needs of the individual patient.

Regarding the physical realization of the pre-molded EDOF LALs, the position dependence of the peripheral optical power 124 can be pre-molded on the front of the LAL 100, on its back, or in combination both in the front and in the back.

All aspects of the blended LALs 100 shown in FIGS. 13-23, and all aspects of the method 200 shown in FIGS. 24-27, can be combined with embodiments of the method 300. One aspect is mentioned specifically: not only the position variation of the peripheral optical power 124 can be pre-molded, but potentially a cylinder can be also pre-molded into the LAL 100.

Figure 29:
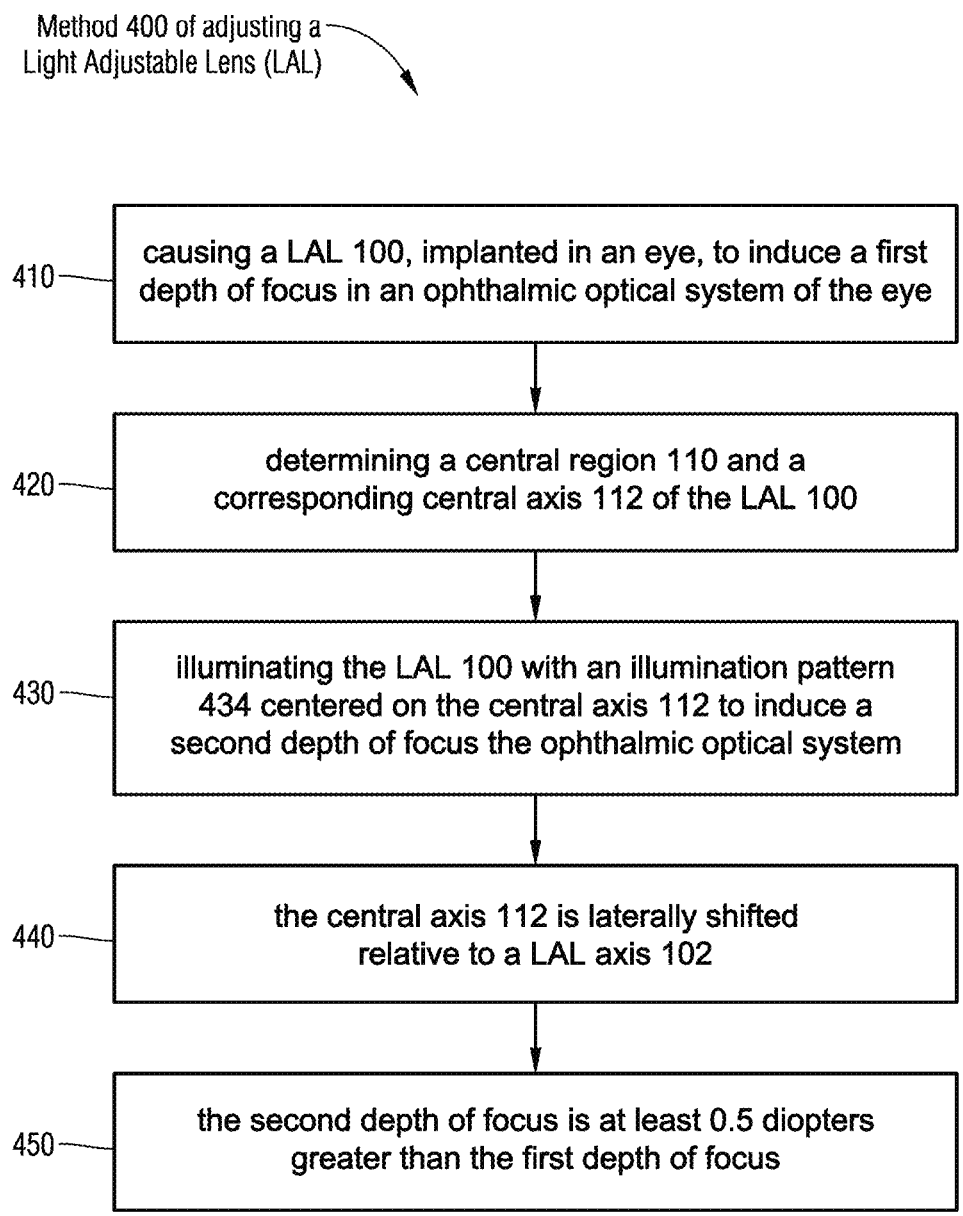
FIG. 29 illustrates a generalized method of adjusting the LAL.

FIG. 29 illustrates that the above two methods, method 200 and method 300 can be thought of as subcases of a more generally articulated method 400 of adjusting the Light Adjustable Lens (LAL) 100. The generalized method 400 can comprise the following steps.

Causing 410 an LAL 100, implanted into an eye, to induce a first depth of focus in an ophthalmic optical system, i.e. the optical system of the eye with its cornea and the implanted LAL 100;

Determining 420 a central region 110 and a corresponding central axis 112 of the LAL 100; and Illuminating 430 the LAL 100 with an illumination pattern 434 centered on the central axis 112 to induce a second depth of focus the ophthalmic optical system; wherein (440) the central axis 112 is laterally shifted relative to a LAL axis 102, and (450) the second depth of focus is at least 0.5 diopters greater than the first depth of focus.

Steps 420-450 can be analogous to the steps 230-260 of the method 200, with appropriate modifications in the last step. In addition, in some embodiments, the causing step 410 can include the applying 220 of the first illumination 222 to the LAL 100, in analogy to step 220 of the method 200. In other embodiments, the causing step 410 can include providing a LAL 100 with a pre-molded depth of focus, in analogy to step 310 of method 300. The pre-molded depth of focus can be induced by a position-dependent peripheral optical power 124 in the peripheral annulus 120, centered on the annulus axis 122. Finally, in some embodiments the causing step 410 may involve a combination of the steps 220 and 310.

As before, all aspects of the blended LALs 100 shown in FIGS. 13-23, all aspects of the method 200 shown in FIGS. 24-27, and all aspects of the method 300 shown in FIG. 28 can be combined with embodiments of the method 400.

Figure 30:
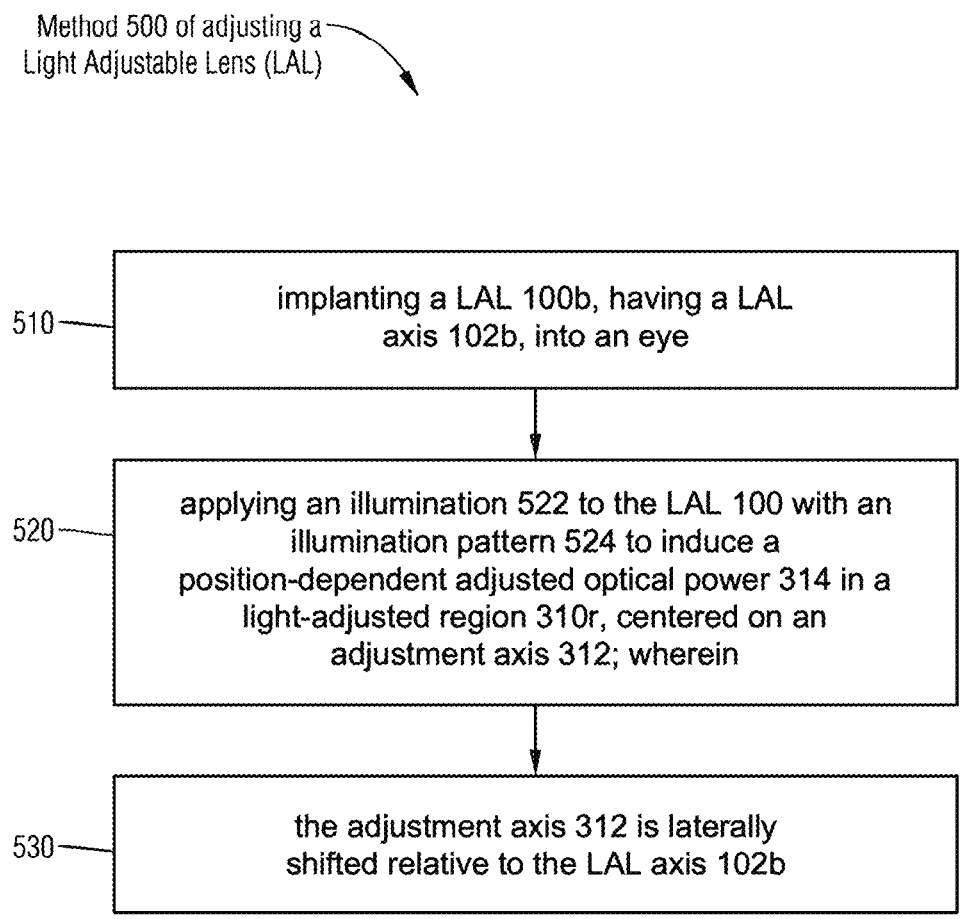
FIG. 30 illustrates a method of adjusting the LAL.

FIG. 30 illustrates a method 500 of adjusting the Light Adjustable Lens (LAL) 100, primarily as shown in FIG. 22. The method 500 can include the following steps.

Implanting 510 a LAL 100b, having a LAL axis 102b, into an eye; and

Applying 520 an illumination 522 to the LAL 100b with an illumination pattern 524 to induce a position-dependent adjusted optical power 314 in a light-adjusted region 310r, centered on an adjustment axis 312; wherein (530) the adjustment axis 312 is laterally shifted relative to the LAL axis 102b.

As before, all aspects of the blended LALs 100 shown in FIGS. 13-23, all aspects of the methods 200/300/400 shown in FIGS. 24-29 can be combined with embodiments of the method 500.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Patents

U.S. Pat. No. 4,260,725.
U.S. Pat. No. 5,225,858.
U.S. Pat. No. 5,236,970.
U.S. Pat. No. 5,278,258.
U.S. Pat. No. 5,376,694.
U.S. Pat. No. 5,444,106.

PUBLICATIONS

Camellin M, Calossi A. A new formula for intraocular lens power calculation after refractive corneal surgery. J Refract Surg. 2006; 22(2):187-99.

Chokshi A R, Latkany R A, Speaker M G, Yu G. Intraocular lens calculations after hyperopic refractive surgery. Ophthalmology. 2007; 104(11):2044-9.

Ciuffreda; Accommodation, the Pupil, and Presbyopia, Chapter 4 in Borisch's Clinical Refraction pp. 77-120, W.B. Saunders Company (1998).

E. J. Fernández, S. Manzanera, P. Piers, P. Artal; Adaptive Optics Visual Simulator", J. Refract. Surg., 2002; 18: S634-S638.

Ellingson, F. T.; Explanation of 3M Diffractive Intraocular Lenses, J. Cataract and Refractive Surgery, 1990; 16: 697-701.

Fam H B, Lim K L. A comparative analysis of intraocular lens power calculation methods after myopic excimer laser surgery. J Refract Surg. 2008; 24:355-360.

Feiz V, Moshirfar M, Mannis M J, Reilly C D, Garcia-Ferrer F, Caspar J J, Lim M C. Nomogram-based intraocular lens power adjustment after myopic photorefractive keratectomy and LASIK. Ophthalmology 2005; 112:1381-1387.

Hansen, T. E., Corydon, L., Krag, S., and Thim, K., New Multifocal Intraocular Lens Design, J. Cataract and Refractive Surgery, 1990; 16:38-41.

Helmholtz, H., Treatise on Physiological Optics (translated by Sohthall J P C), New York: Dover. (1969).

Jin G C, Crandall A S, Jones J J. Intraocular lens exchange due to incorrect lens power. Ophthalmology. 2007; 114: 417-424.

Latkany R A, Chokshi A R, Speaker M G, Abramson J, Soloway B D, Yu G. Intraocular lens calculations after refractive surgery. J Cataract Refract Surg. 2005; 31:562-570.

Mackool R J, Ko W, Mackool R. Intraocular lens power calculation after laser in situ keratomileusis: aphakic refraction technique. J Cataract Refract Surg. 2006; 32:435-437.

Mamalis N, Brubaker J, David D, Espandar L, Werner L. Complications of foldable intraocular lenses requiring explantation or secondary intervention-2007 survey update. J Cataract Refract Surg. 2008; 34:1584-1591.

Murphy C, Tuft S J, Minassian D C. Refractive error and visual outcome after cataract extraction. J Cataract Refract Surg. 2002; 28(1):62-66.

Narvaez J, Zimmerman G, Stulting R D, Chang D H. Accuracy of intraocular lens power prediction using the Hoffer Q, Holladay 1, Holladay 2, and SRK/T formulas. J Cataract Refract Surg. 2006; 32:2050-2053.

Olsen T. Sources of error in intraocular-lens power calculation. J Cataract Refract Surg. 1992; 18:125-129.

Packer M, Brown L K, Hoffman R S, Fine I H. Intraocular lens power calculation after incisional and thermal keratorefractive surgery. J Cataract Refract Surg. 2004; 30:1430-1434.

Packer, M.; Fine, I. H.; Hoffman, R. S., Refractive Lens Exchange with the Array Multifocal Intraocular Lens, H., J. Cataract and Refract Surgery, 2002; 28:421-424.

Preussner P R, Wahl J, Weitzel D, Berthold S, Kriechbaum K, Findl O. Predicting postoperative intraocular lens position and refraction. J. Cataract Refract Surg. 2004; 30:2077-2083.

Steiner, R. F., Aler, B L., Trentacost, D J., Smith, P. J., Taratino, N. A., A Prospective Comparative Study of the AMO Array zonal-progressive multifocal silicone intraocular lens and a monofocal intraocular lens, Opthalmology, 1999; 106(7): 1243-1255.

Sun, X. Y.; Vicary, D.; Montgomery, P.; Griffiths, M. Toric intraocular lenses for correcting astigmatism in 130 eyes. Ophthalmology, 2000; 107(9); 1776-81.

Thibos, L. N.; Hong, X.; Bradley, A.; Applegate, R. A, Accuracy and Precision of Objective Refraction from Wavefront Aberrations, Journal of Vision, 2004; 4: 329-351.

Wang L, Booth M A, Koch D D. Comparison of intraocular lens power calculation methods in eyes that have undergone LASIK. Ophthalmology 2004; 111:1825-1831.

The invention claimed is:

1. A method of adjusting a Light Adjustable Lens (LAL), the method comprising the steps of:
implanting a LAL into an eye;
applying a first illumination to the LAL with a first illumination pattern to induce a position-dependent peripheral optical power in at least a peripheral annulus, centered on an annulus axis;
determining a central region and a corresponding central axis of the LAL; and
applying a second illumination to the LAL with a second illumination pattern to induce a position-dependent central optical power in the central region of the LAL; wherein
the central axis is laterally shifted relative to the annulus axis,
an average of the central optical power is at least 0.5 diopters different from an average of the peripheral optical power, and
the position dependences of the central optical power and the peripheral optical power generate a logarithm of a Minimal Angle Resolved as a function of diopters that correspond to viewing distances, that lacks a midrange minimum in a diopter range that corresponds to a viewing distance range of 50 cm-2 m.

2. The method of claim 1, wherein:
the average of the central optical power is at least 1.0 diopter different from the average of the peripheral optical power.

3. The method of claim 1, wherein:
the average of the central optical power is at least 0.5 diopters higher than an average of the peripheral optical power.

4. The method of claim 1, wherein:
the average of the central optical power is at least 0.5 diopters lower than an average of the peripheral optical power.

5. The method of claim 1, the applying the first illumination comprising:
applying the first illumination with a first illumination pattern to induce the position-dependent peripheral optical power in a light-adjusted region that includes the peripheral annulus and the central region.

6. The method of claim 1, the determining a central axis comprising:
identifying a visual axis of the eye as the central axis; and
applying the second illumination in the central region of the LAL with the visual axis as the corresponding central axis.

7. The method of claim 1, the determining a central axis comprising:
determining the central axis with an iris of the eye being in a non-dilated state; and
applying the second illumination in the central region of the LAL with the so-determined corresponding central axis.

8. The method of claim 1, the determining a central axis comprising:
determining the central axis with an iris of the eye being dilated to an iris-radius no more than 30% greater than a non-dilated iris-radius; and
applying the second illumination in the central region of the LAL with the so-determined corresponding central axis.

9. The method of claim 1, the determining a central axis comprising:
determining the central axis before an iris of the eye is dilated;
registering the determined central axis with a feature of the eye; and
reconstructing the determined and registered central axis after the iris is dilated, before the applying of the second illumination.

10. The method of claim 1, wherein:
the applying the first illumination and the applying the second illumination induces a transition between the central region and the peripheral annulus, having a transition optical power that changes from the central optical power to the peripheral optical power.

11. The method of claim 1, wherein:
the central optical power has an approximately flat position-dependence, having an optical power variation less than 0.2 diopters over a central 50% of the central region.

12. The method of claim 1, wherein:
a spherical aberration caused by the position-dependence of one of the peripheral optical power, and a combination of the central optical power, the peripheral optical power, and a transition optical power, is in a range of −0.05 µm to −1 µm at a diameter of 4 mm in a plane of the LAL.

13. The method of claim 1, wherein:
a spherical aberration caused by the position-dependence of one of the peripheral optical power, and a combination of the central optical power, the peripheral optical power, and a transition optical power, is in a range of −0.05 μm to −2 μm at a diameter of 6 mm in a corneal plane of an eye upon an implantation of the LAL in the eye.

14. The method of claim 1, wherein:
at least on the central optical power and the peripheral optical power is selected such that a spherical aberration caused by the position-dependence of at least one of the central optical power and the peripheral optical power approximately compensates a spherical aberration of a cornea of the eye.

15. The method of claim 1, wherein:
at least one of
the position-dependent central optical power involves a cylinder angular dependence; and
the position-dependent peripheral optical power involves a cylinder angular dependence.

16. The method of claim 1, wherein:
the applying the first illumination and the applying the second illumination is separated by less than 48 hours.

17. The method of claim 1, comprising:
applying a lock-in illumination, to lock in the induced peripheral optical power and the induced central optical power in the LAL.

18. The method of claim 1, further comprising:
applying a third illumination to the LAL with a third illumination pattern centered on the central axis to reduce the position-dependent central optical power, induced in by the second illumination in the central region of the LAL.

19. A method of adjusting a Light Adjustable Lens (LAL), the method comprising the steps of:
implanting a LAL into an eye, the LAL having a pre-molded position-dependent peripheral optical power in at least a peripheral annulus, centered on an annulus axis;
determining a central region and a corresponding central axis of the LAL; and
applying a central illumination to the LAL with a central illumination pattern to induce a position-dependent central optical power in the central region of the LAL;
wherein
the central axis is laterally shifted relative to the annulus axis,
an average of the central optical power is at least 0.5 diopters different from an average of the peripheral optical power, and
the position dependences of the central optical power and the peripheral optical power generate a logarithm of a Minimal Angle Resolved as a function of diopters that correspond to viewing distances, that lacks a midrange minimum in a diopter range that corresponds to a viewing distance range of 50 cm-2 m.

20. A method of adjusting a Light Adjustable Lens (LAL), the method comprising the steps of:
implanting a LAL, having a LAL axis, into an eye; and
applying an illumination to the LAL with an illumination pattern to induce a position-dependent optical power in a light-adjusted region, centered on an adjustment axis;
wherein
the adjustment axis is laterally shifted relative to the LAL axis, and
the position dependence of the optical power generates a logarithm of a Minimal Angle Resolved as a function of diopters that correspond to viewing distances, that lacks a midrange minimum in a diopter range that corresponds to a viewing distance range of 50 cm-2 m.

* * * * *